US011865125B2

(12) United States Patent
Farese et al.

(10) Patent No.: US 11,865,125 B2
(45) Date of Patent: Jan. 9, 2024

(54) APKC INHIBITORS AND METHODS OF TREATING A NEURODEGENERATIVE DISEASE OR DISORDER

(71) Applicants: UNIVERSITY OF SOUTH FLORIDA, Tampa, FL (US); UNITED STATES DEPARTMENT OF VETERANS AFFAIRS, Washington, DC (US)

(72) Inventors: Robert Vito Farese, St. Petersburg, FL (US); Mini Paliyath Sajan, Wesley Chapel, FL (US); Margaret Genevieve Higgs, St. Petersburg, FL (US)

(73) Assignees: UNIVERSITY OF SOUTH FLORIDA, Tampa, FL (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 17/554,924

(22) Filed: Dec. 17, 2021

(65) Prior Publication Data
US 2022/0175804 A1    Jun. 9, 2022

Related U.S. Application Data

(62) Division of application No. 16/088,356, filed as application No. PCT/US2017/024090 on Mar. 24, 2017, now abandoned.

(60) Provisional application No. 62/362,282, filed on Jul. 14, 2016, provisional application No. 62/313,227, filed on Mar. 25, 2016.

(51) Int. Cl.
| | |
|---|---|
| *A61K 31/675* | (2006.01) |
| *A61P 25/28* | (2006.01) |
| *A61K 33/242* | (2019.01) |
| *A61K 31/122* | (2006.01) |

(52) U.S. Cl.
CPC .......... *A61K 31/675* (2013.01); *A61K 31/122* (2013.01); *A61K 33/242* (2019.01); *A61P 25/28* (2018.01); *C12Y 304/23046* (2013.01)

(58) Field of Classification Search
CPC ...... A61K 33/242; A61K 31/194; A61P 25/28
See application file for complete search history.

(56) References Cited

U.S. PATENT DOCUMENTS

| | | |
|---|---|---|
| 2006/0185026 A1 | 8/2006 | Sacktor et al. |
| 2008/0025962 A1 | 1/2008 | Hayashi et al. |
| 2012/0232037 A1 | 9/2012 | Farese |

FOREIGN PATENT DOCUMENTS

| | | |
|---|---|---|
| WO | 2015017549 A1 | 2/2015 |

OTHER PUBLICATIONS

PCT International Search Report and Written Opinion, PCT/US2017/024090, dated Jun. 16, 2017, 12 pages.

*Primary Examiner* — Sahar Javanmard
(74) *Attorney, Agent, or Firm* — Quarles & Brady LLP

(57) ABSTRACT

Provided herein are formulations effective for and methods of treating or preventing a neurodegenerative disorder in a subject in need thereof that can include administering an amount of an aPKC inhibitor to a subject in need thereof.

18 Claims, 57 Drawing Sheets

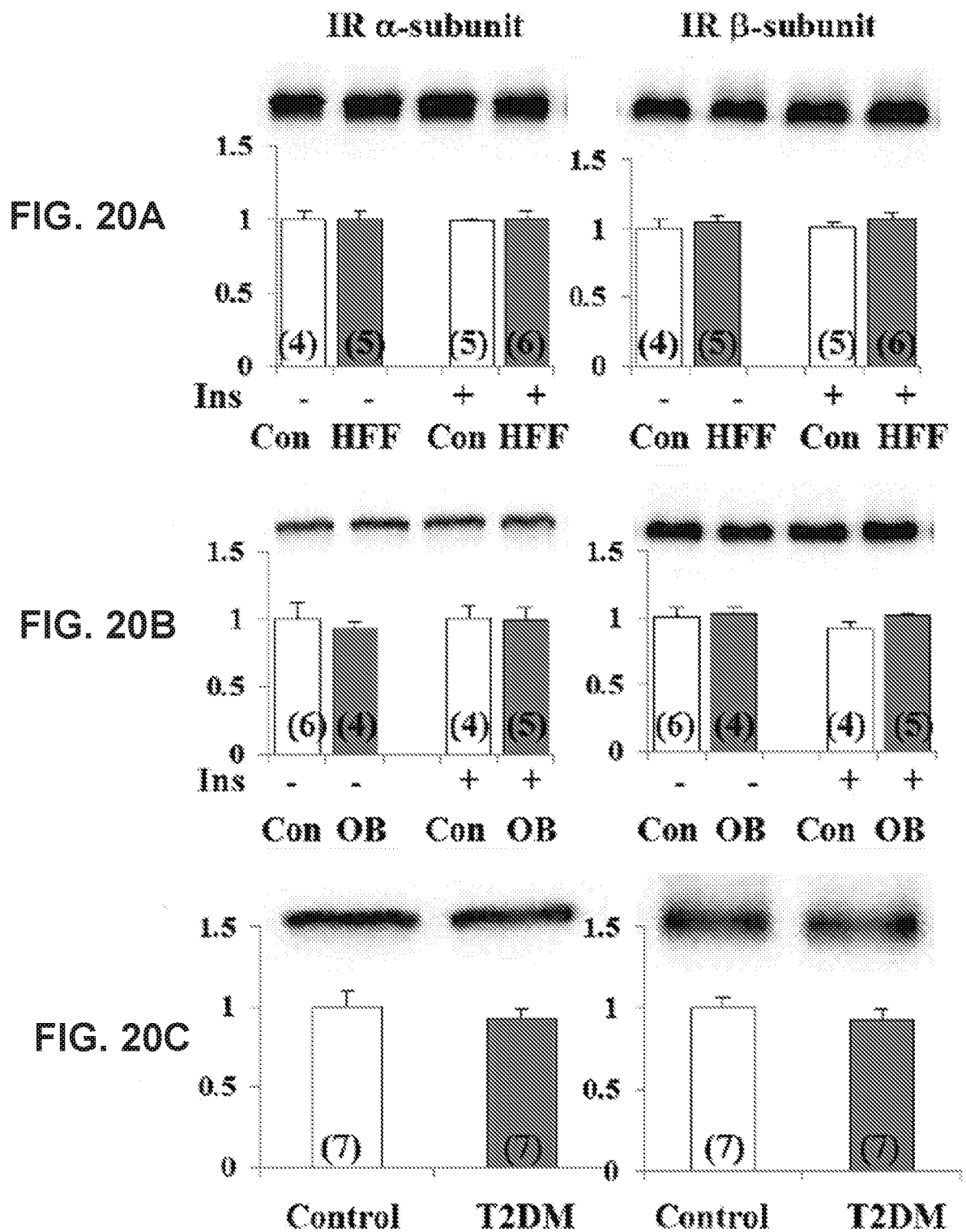

APKC INHIBITORS AND METHODS OF TREATING A NEURODEGENERATIVE DISEASE OR DISORDER

CROSS-REFERENCE TO RELATED APPLICATIONS

This application is a division of U.S. patent application Ser. No. 16/088,356, filed Sep. 25, 2018, which is a national stage filing under 35 U.S.C. § 371 of International Application No. PCT/US2017/024090, filed Mar. 24, 2017, which claims priority to U.S. Provisional Application No. 62/313,227, filed on Mar. 25, 2016, and U.S. Provisional Application No. 62/362,282, filed on Jul. 14, 2016, all of which are herein incorporated by reference in full.

STATEMENT REGARDING FEDERALLY SPONSORED RESEARCH OR DEVELOPMENT

This invention was made with government support under grant numbers 7RO1DK-065969-09 and DK300136 awarded by the National Institutes of Health. The government has certain rights in the invention.

BACKGROUND

Alzheimer's disease (AD) is a neurodegenerative disorder that effects over 5.5 million people in the U.S. alone and over 25 million world-wide. AD and other neurodegenerative disorders are a significant public health problem with very limited therapies and no viable cures. As such, there exists an urgent and unmet need for improved therapies and/or preventatives for neurodegenerative diseases, including AD.

SUMMARY

In some aspects, described herein are methods of treating or preventing a neurodegenerative disorder in a subject in need thereof that can include the step of administering an amount of an aPKC inhibitor capable of crossing the blood brain barrier to the subject in need thereof. The aPKC inhibitor can be ICAPP. The aPKC inhibitor can be ACPD. The amount of the aPKC inhibitor can be an amount effective to decrease phosphorylation of Akt. The amount of the aPKC inhibitor can be an amount effective to decrease activity of aPKC. The amount of the aPKC inhibitor can be an amount effective decrease activity of β-secretase. The amount of the aPKC inhibitor can be an amount effective decrease the amount of $A\beta_{1-40/42}$. The amount of the aPKC inhibitor can be an amount effective decrease the amount of thr-231-phospho-tau. The amount of the aPKC inhibitor can be an amount effective decrease the activity of 70 kDa PKC-λ/ι. The amount of the aPKC inhibitor can be an amount effective to increase the activity of FoxO1, FoxO3a, or FoxO1 and FoxO3a. The amount of the aPKC inhibitor can be an amount effective to increase activity, levels, or activity and levels of PGC-1α. The subject in need thereof can be hyperinsulinemic. The subject in need thereof can be hyperinsulinemic in the central nervous system. The subject in need thereof can be diabetic. The subject can be metabolic syndrome. The subject can be obese. The neurodegenerative disorder can be Alzheimer's disease or a symptom thereof. The amount of the aPKC inhibitor can be administered to the subject in need thereof once daily. The amount of the aPKC inhibitor can be administered to the subject in need thereof once every other day. The amount of the aPKC inhibitor administered can range from about 10 mg/kg to about 20 mg/kg. The amount of the aPKC inhibitor can be administered systemically. The amount of the aPKC inhibitor can be administered intravenously or subcutaneously.

In some aspects, described herein are methods of treating or preventing a neurodegenerative disorder in a subject in need thereof that can include the step of administering systemically an amount of an aPKC inhibitor that is not capable of crossing the blood brain barrier to the subject in need thereof. The aPKC inhibitor can be aurothiomalate (ATM). The amount of the aPKC inhibitor can be an amount effective to decrease phosphorylation of Akt. The amount of the aPKC inhibitor can be an amount effective to decrease activity of aPKC. The amount of the aPKC inhibitor can be an amount effective decrease activity of β-secretase. The amount of the aPKC inhibitor can be an amount effective decrease the amount of $A\beta_{1-40/42}$. The amount of the aPKC inhibitor can be an amount effective decrease the amount of thr-231-phospho-tau. The aPKC inhibitor can an amount effective decrease the activity of 70 kDa PKC-λ/ι. The amount of the aPKC inhibitor can be an amount effective to increase the activity of FoxO1, FoxO3a, or FoxO1 and FoxO3a. The amount of the aPKC inhibitor can be an amount effective to increase activity, levels, or activity and levels of PGC-1α. The subject in need thereof can be hyperinsulinemic. The subject in need thereof can be hyperinsulinemic in the central nervous system. The subject in need thereof can be diabetic. The subject can have metabolic syndrome. The subject in need thereof can be obese. The neurodegenerative disorder can be Alzheimer's disease or a symptom thereof. The amount of the aPKC inhibitor can be administered to the subject in need thereof once daily. The amount of the aPKC inhibitor can be administered to the subject in need thereof once every other day. The amount of the aPKC inhibitor administered can range from about 50 mg/kg to about 70 mg/kg. The amount of the aPKC inhibitor can be administered intravenously or subcutaneously.

BRIEF DESCRIPTION OF THE DRAWINGS

Further aspects of the present disclosure will be readily appreciated upon review of the detailed description of its various embodiments, described below, when taken in conjunction with the accompanying drawings.

(FIGS. 14A-14C), ×10 magnification, anterocortical sagittal sections; (FIGS. 14D-14F), ×60 magnification, anterocortical neurons; and (FIGS. 14G-14I), ×10 magnification, hippocampus. Portrayed values are mean±SEM of (N) mice and reflect relative staining of p-Ser-473-Akt per standard area of anterior cortex (FIG. 14J) and hippocampus (FIG. 14K). *$P<0.05$, $P<0.01$, and *$P<0.001$ for HFF or ob/ob vs. Con mice (ANOVA).

FIGS. 20A-20C show graphs and images of representative blots that can demonstrate a lack of alteration in levels of insulin receptor subunits, α and β, in high-fat fed mice, ob/ob mice, and type 2 diabetic (T2DM) monkeys. Relative values are mean±SEM of (N) animals.

DETAILED DESCRIPTION

Figure 1:
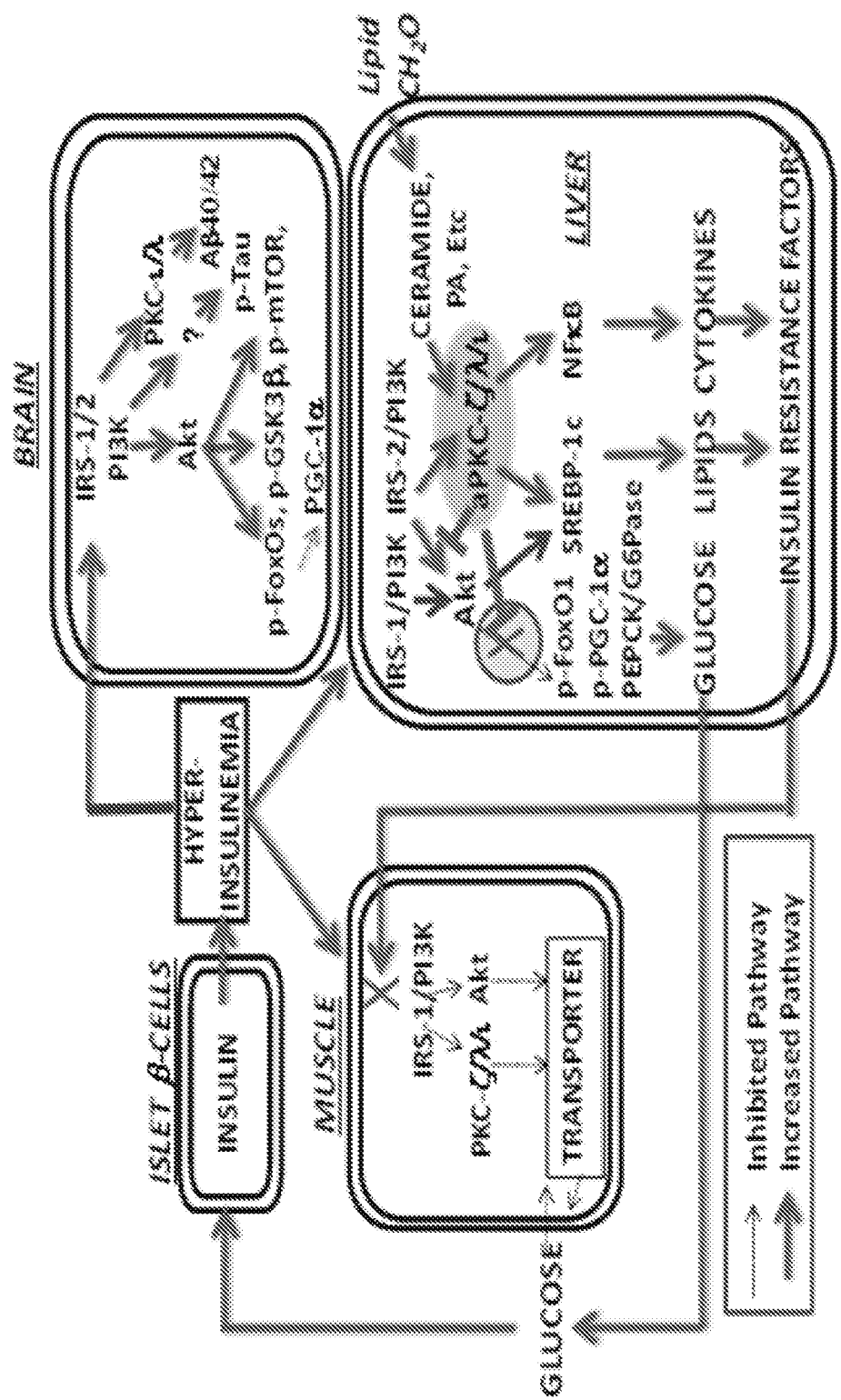
FIG. 1 depicts hyperinsulinization of the brain and activation of Akt and PKC-ι/λ, and subsequent increases in phosphorylation and inactivation of FoxO1/3a/4/6 and PGC-1α, and increases in levels of phosphor-tau and $A\beta_{1-40/42}$ in insulin-resistant disorders. Note that increased aPKC in liver first inhibits phosphorylation of FoxO1 and PGC-1α, and later inhibits Akt activation by IRS-1/IRS-1/PI3K.
Figure 2A:
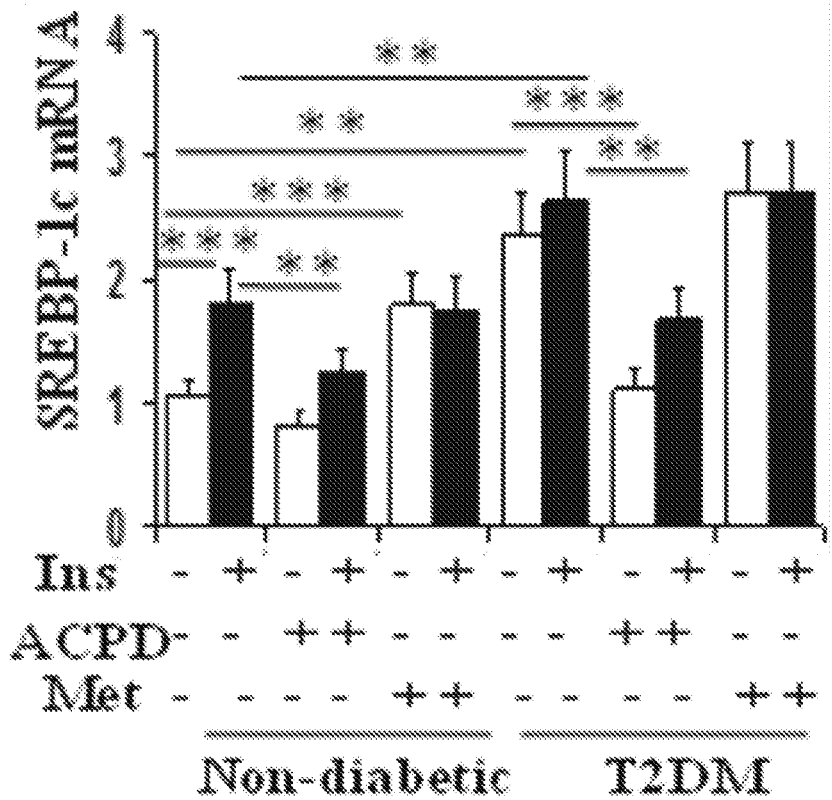
FIGS. 2A-2F depict effects of 24-hr Rx with 200 nM insulin, 100 μM metformin, and aPKC inhibitor, 1 μM ACPD on expression of SREBP-1c, FAS, ACC, PEPCK, G6Pase, and PGC-1α in hepatocytes of lean non-diabetic and T2D humans. Relative values are Mean±SEM (N=4-8). Asterisks: *, P<0.05; , P<0.01; *, P<0.001. ANOVA.
Figure 2B:
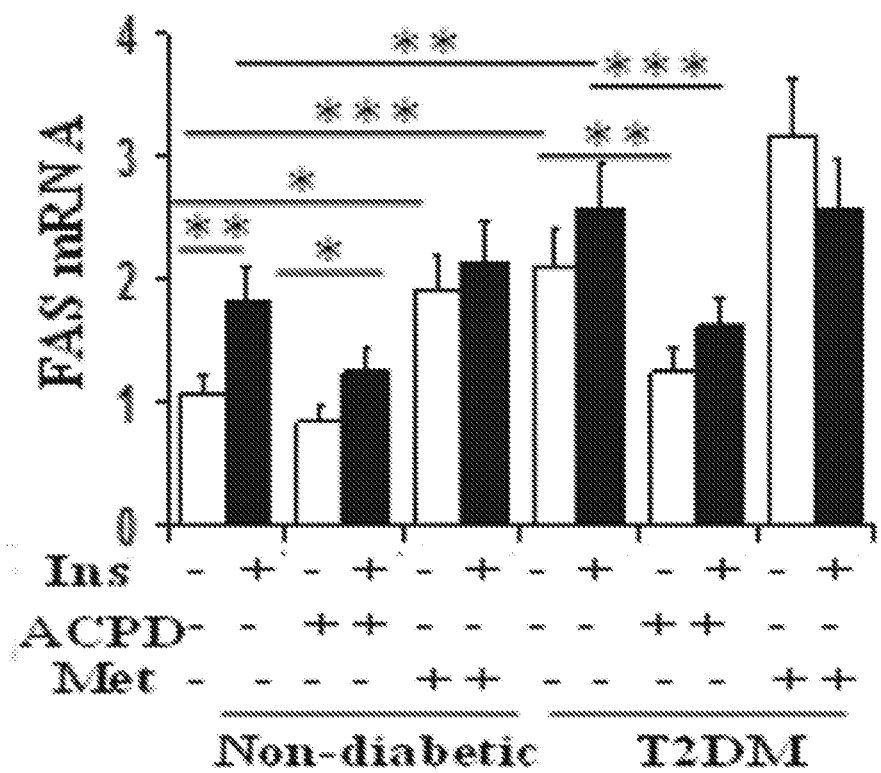
Figure 2C:
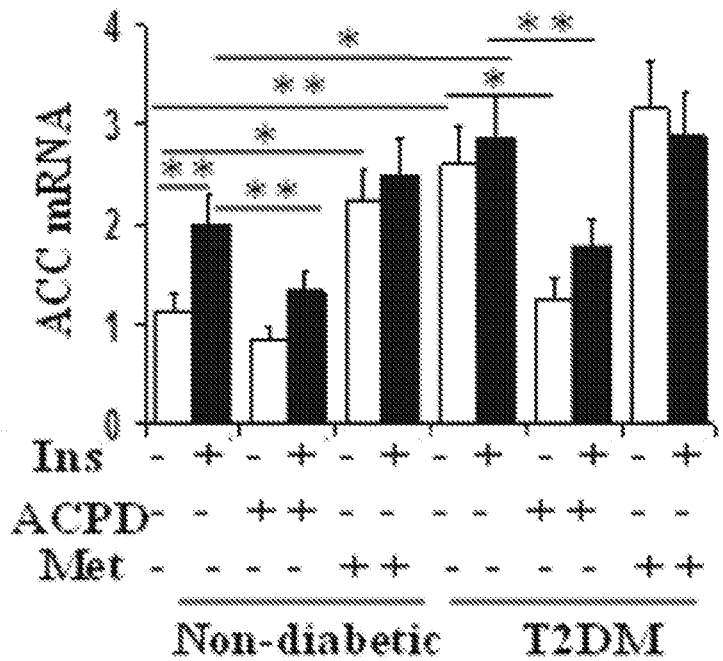
Figure 2D:
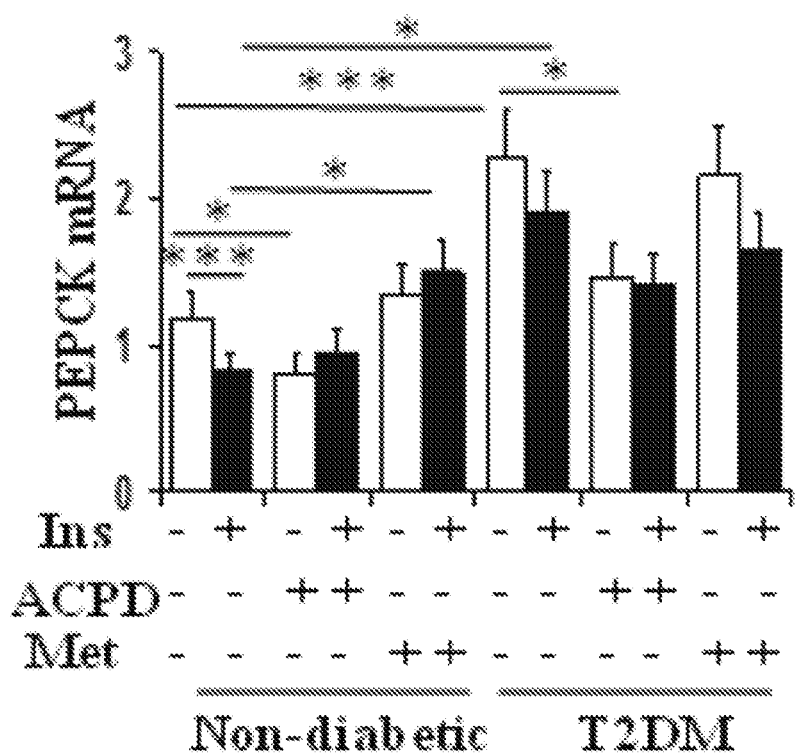
Figure 2E:
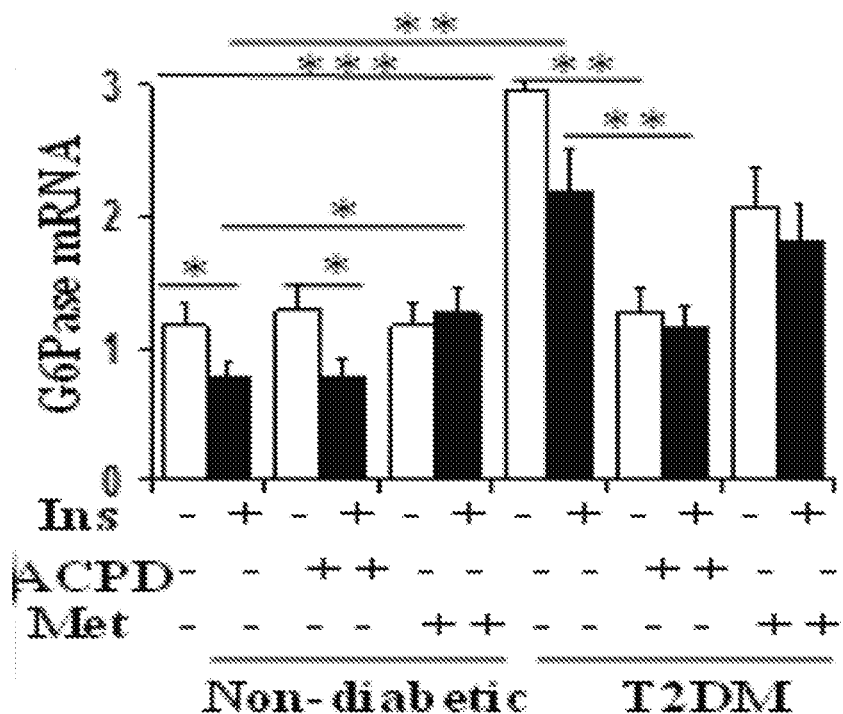
Figure 2F:
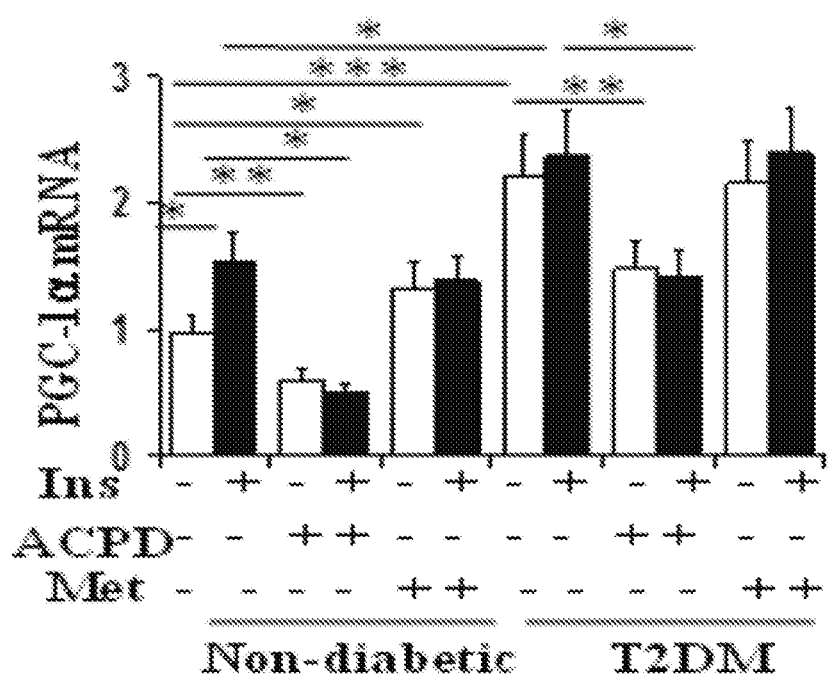
Figure 3A:
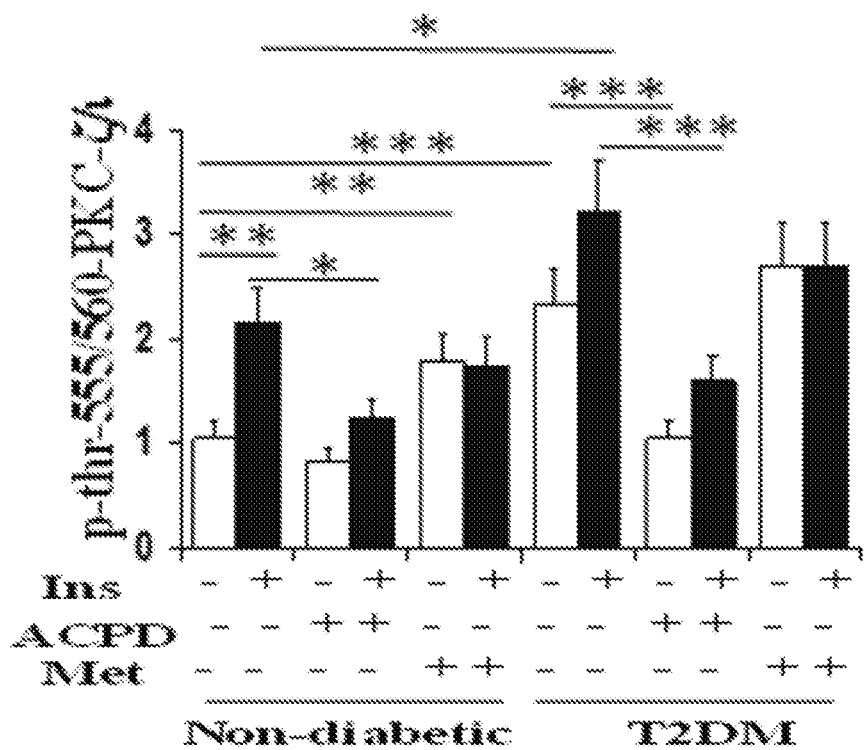
FIG. 3A-3D depict effects of 24-hr Rx with 200 nM insulin, 100 μM metformin, and aPKC inhibitor, 1 μM ACPD on activity of aPKC (a) and Akt (b), FoxO1 phosphorylation (c), and PGC-1α protein levels (d) in hepatocytes of lean non-diabetic and T2D humans. Relative values. Mean±SEM (N=4-8). Asterisks: *, P<0.05; , P<0.01; *, P<0.001.
Figure 3B:
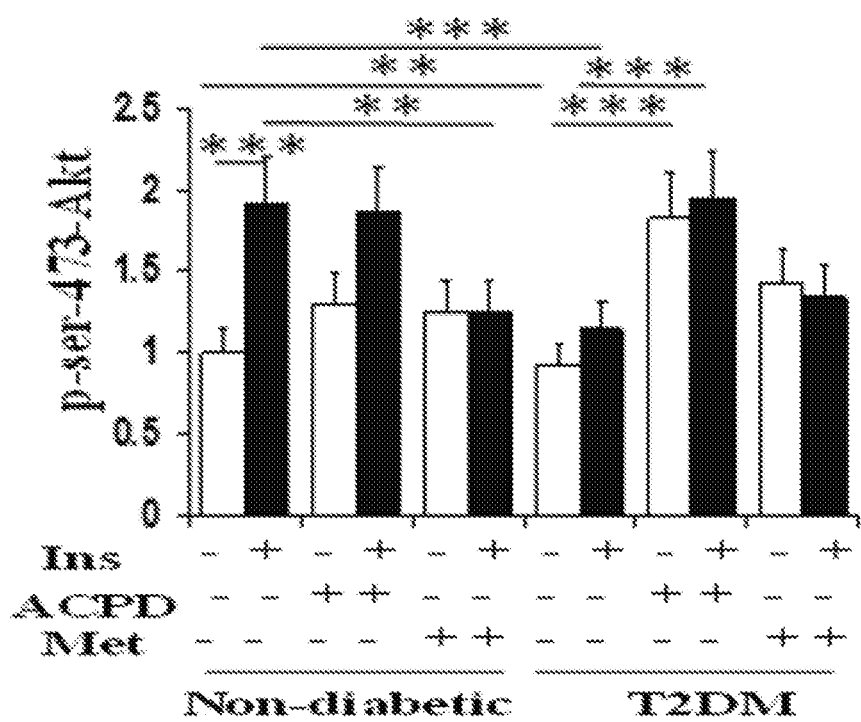
Figure 3C:
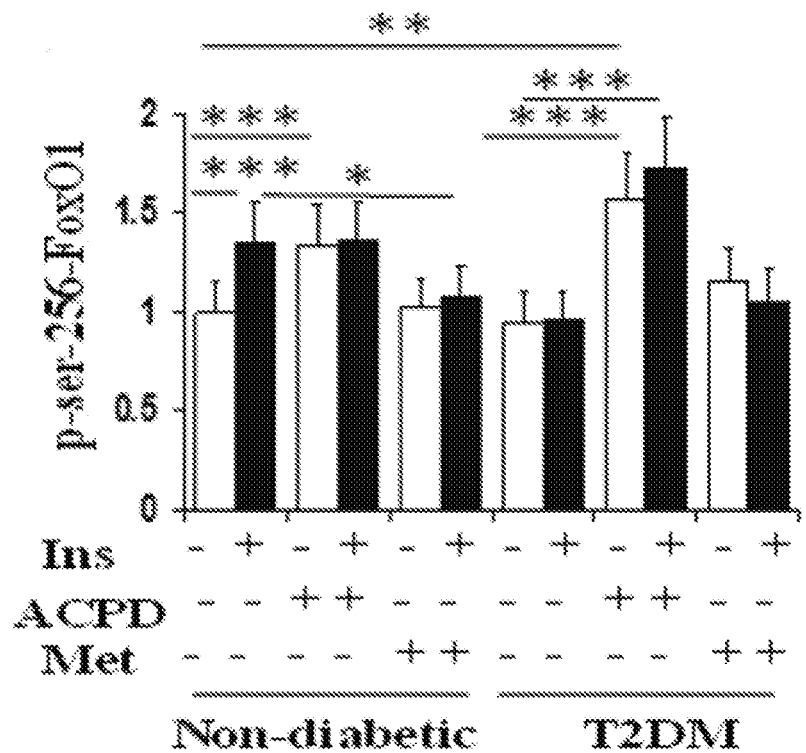
Figure 3D:
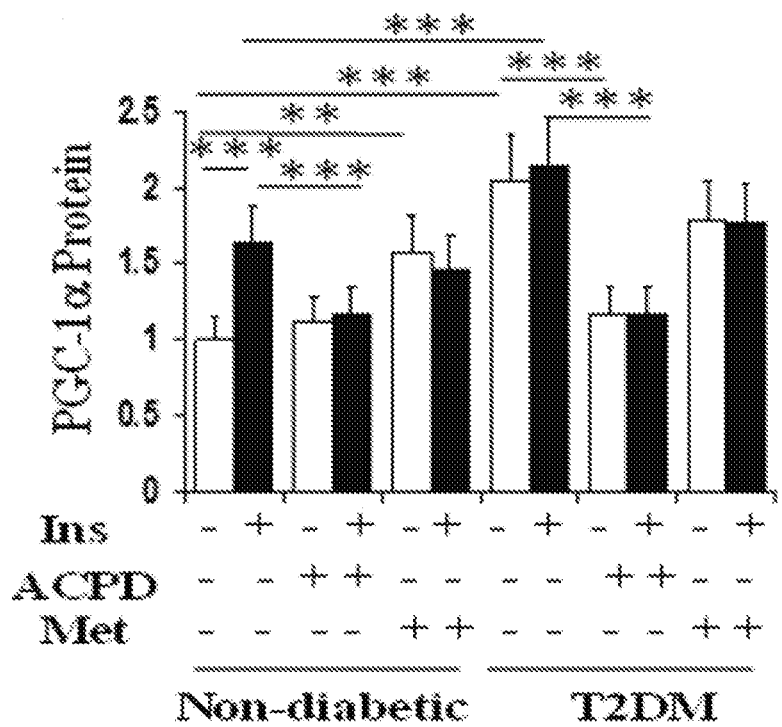

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, endocrinology, physiology, and the like, which are within the skill of the art. Such techniques are explained fully in the literature.

Definitions

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques.

As used herein, "active agent" or "active ingredient" refers to a component or components of a composition to which the whole or part of the effect of the composition is attributed.

As used herein, "anti-infectives" can include, but are not limited to, antibiotics, antibacterials, antifungals, antivirals, and antiprotozoals.

As used herein, an "aPKC inhibitor" can refer to a compound that can reduce the amount of and/or activity of an aPKC. The aPKC inhibitor can be a specific aPKC inhibitor, which can refer to an aPKC inhibitor that acts on an aPKC and does not have any measurable or significant action on other PKCs.

As used herein, "control" is an alternative subject or sample used in an experiment for comparison purposes and included to minimize or distinguish the effect of variables other than an independent variable. A control can be positive or negative. One of ordinary skill in there art will appreciate suitable controls.

As used herein, "dose," "unit dose," or "dosage" refers to physically discrete units suitable for use in a subject, each unit containing a predetermined quantity of the nanoparticle composition or formulation calculated to produce the desired response or responses in association with its administration.

As used herein, "effective amount" or "amount effective", as used interchangeably herein, can refer to the amount of a composition or pharmaceutical formulation described herein that will elicit a desired biological or medical response of a tissue, system, animal, plant, protozoan, bacteria, yeast or human that is being sought by the researcher, veterinarian, medical doctor or other clinician. The effective amount will vary depending on the exact chemical structure of the composition or pharmaceutical formulation, the causative agent and/or severity of the infection, disease, disorder, syndrome, or symptom thereof being treated or prevented, the route of administration, the time of administration, the rate of excretion, the drug combination, the judgment of the treating physician, the dosage form, and the age, weight, general health, sex and/or diet of the subject to be treated. "Effective amount" can refer to an amount of a composition or pharmaceutical formulation described herein that can to reduce blood glucose level, reduce hyperinsulinemia in the periphery and/or CNS, decrease phosphorylation an/or activity of Akt, such as in the CNS, directly and/or indirectly decrease activity of aPKC in the CNS, decrease activity of β-secretase in the CNS, decrease the amount of $A\beta_{1-40/42}$ in the CNS, decrease the amount of thr-231-phospho-tau in the CNS, decrease the activity of aPKC isoform PKC-10 in the CNS, decrease p-FoxOs in the CNS, decrease pGSK3β in the CNS, decrease p-mTOR in the CNS, increase the activity of FoxO1, FoxO3a, or FoxO1 and FoxO3a, and/or increase PGC-1α in the CNS. The "effective amount" can refer to the amount of an aPKC inhibitor or formulation thereof described herein that can treat and/or prevent a neurodegenerative disorder or a symptom thereof. Such neurodegenerative disorders can be, without limitation, AD.

As used herein "immunomodulator," refers to an agent, such as a therapeutic agent, which is capable of modulating or regulating one or more immune function or response.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

The terms "treat," "treating," "treatment," and grammatical variations thereof as used herein include partially or completely delaying, alleviating, mitigating or reducing the intensity of one or more attendant symptoms of a disorder or condition such as neurodegenerative disorder and/or alleviating, mitigating or impeding one or more causes of a disorder or condition such as a neurodegenerative disorder. Treatments according to the embodiments disclosed herein may be applied preventively, prophylactically, palliatively, or remedially, which are collectively referred to herein as "preventing". In some instances, the terms "treat," "treating," "treatment," and grammatical variations thereof include partially or completely reducing a condition or symptom associated with a neurodegenerative disorder prior to treatment of the subject or as compared with the incidence of such condition or symptom in a general or study population.

Discussion

Neurodegenerative disorders, such as AD, are a significant public health issue directly affecting over 25 million people worldwide. The pathologies of some neurodegenerative disorders are poorly understood. Additionally, there are limited treatment options for neurodegenerative disorders, which mainly focus on management of the disorder and maintaining quality of life as opposed to treating the underlying pathology. Moreover, what treatments are available that directly combat the disorder often come with harsh side effects due to their non-specificity.

It has been observed that some neurodegenerative disorders, such as AD, occurs at a higher rate in patients with other diseases or disorders, such as diabetes or metabolic syndrome. Although it was previously thought that this was a side effect of the brain being insulin resistant, this does not appear to be the case in at least some instances. As shown in FIG. 1, atypical PKC (aPKC), can be hyperactivated in the liver and the brain by hyperinsulinemia, which can directly or indirectly lead to aberrant signaling in the brain. Aberrant signaling in the brain can contribute to the development of neurodegenerative disorders.

With that said, described herein are aPKC inhibitors and formulations thereof that can directly or indirectly decrease aPKC in the brain and methods of treating a neurodegenerative disorder, such as AD, in a subject in need thereof by administering an aPKC inhibitor or formulation thereof to the subject in need thereof. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

aPKC Inhibitors and Pharmaceutical Formulations Thereof

Insulin can result in an increase in atypical PCK (aPKC) activity in the liver, muscle, and brain. Increased and hyperactivity of aPKC can negatively impact signaling the periphery and central nervous system (CNS), which can cause and/or potentiating disorders such as metabolic syndrome, diabetes, and insulin resistance in the periphery and aberrant signaling in the CNS. Inhibition of aPKC directly in the CNS can reduce hyperinsulinemia and/or the effects thereof and restore signaling in the CNS. Inhibition of aPKC and/or Akt activity in the periphery (e.g. liver and/or muscle) can indirectly reduce the effects of hyperinsulinemia in the brain as a result of restoring insulin levels to normal in the periphery and CNS, which can result in a restoration of signaling to normal in the CNS. Provided herein are aPKC inhibitors and pharmaceutical formulations thereof that can be used for treatment and/or prevention of a neurodegenerative disorder, such as Alzheimer's disease (AD), in a subject in need thereof. The aPKC inhibitor can be capable of crossing the blood brain barrier and thus directly inhibit aPKC in the CNS of the subject. In some aspects, the aPKC inhibitor that can be capable of crossing the blood brain barrier can be [1H-imidazole-4-carboxamide,5-amino]-[2,3-dihydroxy-4-[(phosphono-oxy)methyl]cyclopentane-[1R-(1a,2b,3b,4a)] (ICAPP) or 2-acetyl-cyclopentane-1,3-dione (ACPD). In other aspects, the aPKC inhibitor cannot cross the blood brain barrier, and thus when administered systemically can indirectly inhibit aPKC activity and/or amount in the CNS by altering (such as decreasing) circulating, and thus CNS, insulin levels which can decrease the activity of CNS aPKC. The aPKC inhibitor that cannot cross the blood brain barrier can be aurothiomalate (ATM).

Pharmaceutical Formulations

Also provided herein are pharmaceutical formulations that can include an amount of an aPKC inhibitor described herein and a pharmaceutical carrier appropriate for administration to an individual in need thereof. The individual in need thereof can have or can be suspected of having a neurodegenerative disorder or symptom thereof. The subject in need thereof can also have hyperinsulinemia in the periphery and/or CNS, type one diabetes, type 2 diabetes, obesity, metabolic syndrome, and/or a symptom thereof. The pharmaceutical formulations described herein can include an amount of an aPKC inhibitor described herein that can be an amount effective to treat and/or prevent a neurodegenerative disorder or a symptom thereof. In some aspects the neurodegenerative disorder is AD. The aPKC inhibitor, in some aspects, can be included in the manufacture of a medicament for treatment of a neurodegenerative disorder or a symptom there, including, but not limited to, AD.

The formulations provided herein can be administered via any suitable administration route. For example, the formulations (and/or compositions) can be administered to the subject in need thereof orally, intravenously, intramuscularly, intravaginally, intraperitoneally, rectally, parenterally, topically, intranasally, or subcutaneously. Other suitable routes are described herein. In some embodiments, the aPKC inhibitor contained in the pharmaceutical formulation can have a formula according to Formula 1.

Parenteral Formulations

The aPKC inhibitor can be formulated for parenteral delivery, such as injection or infusion, in the form of a solution or suspension. The aPKC inhibitor contained in the pharmaceutical formulation can be capable of crossing the blood brain barrier when administered systemically. In some aspects, the aPKC inhibitor or amount thereof that is capable of crossing the blood brain barrier can be effective to reduce the activity and/or amount of periphery (e.g. liver and muscle) and/or CNS (e.g. neuronal and brain) aPKC. The aPKC inhibitor that can be capable of crossing the blood brain barrier can be ICAPP or ACPD or a pharmaceutical salt. In other aspects, the aPKC inhibitor is not capable of crossing the blood brain barrier. Thus, in some aspects, the aPKC inhibitor that is not capable of crossing the blood brain barrier can be ATM or a pharmaceutical salt thereof. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the aPKC inhibitor as described herein can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-8-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of aPKC inhibitor.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the aPKC inhibitor in the needed amount in the appropriate solvent or dispersion medium with one or more of the excipients listed above, as required, followed by filtered sterilization. Dispersions can be prepared by incorporating the various sterilized aPKC inhibitor into a sterile vehicle which contains the basic dispersion medium and the required other ingredients from those listed above. Sterile powders for the preparation of sterile injectable solutions can be prepared by vacuum-drying and freeze-drying techniques, which yields a powder of the aPKC inhibitor plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more aPKC inhibitor. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The aPKC inhibitor(s) as described herein can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the aPKC inhibitor can be administered as a liquid formulation, such as a solution or suspension, a semi-solid formulation, such as a lotion or ointment, or a solid formulation. In some embodiments, the aPKC inhibitor can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing a aPKC inhibitor thereof as described herein are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing aPKC inhibitor as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing a aPKC inhibitor and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing a aPKC inhibitor as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof.

Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, C12-C15 alkyl benzoates, mineral oil, squalane, cyclomethicone, capric/caprylic triglycerides, and combinations thereof.

Also described herein are foams that can include an aPKC inhibitor as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The aPKC inhibitor or pharmaceutical salt thereof as described herein can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing an aPKC inhibitor as described herein can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing an aPKC inhibitor as described herein can be prepared using one or more pharmaceutically acceptable excipients, including diluents, preservatives, binders, lubricants, disintegrators, swelling agents, fillers, stabilizers, and combinations thereof.

Delayed release dosage formulations containing an aPKC inhibitor as described herein can be prepared as described in standard references such as "Pharmaceutical dosage form tablets", eds. Liberman. et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing a aPKC inhibitor as described herein can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing an aPKC inhibitor or pharmaceutical salt thereof. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Other suitable additional active agents include, but are not limited to, statins, cholesterol lowering drugs, glucose lowering drugs. The aPKC inhibitor(s) can be used as a monotherapy or in combination with other active agents for treatment of metabolic disorder (diabetes, high-cholesterol, hyperlipidemia, high-triglycerides).

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), H2-receptor antagonists (e.g. cimetidine, famotidine, lafutidine, nizatidine, rafitidine, and roxatidine), tritoqualine, catechin, cromoglicate, nedocromil, and 132-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositomomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Methods of Using the aPKC Inhibitor(s) and Formulations Thereof

Hyperinsulinemia in the periphery can contribute to insulin resistance and ultimately many disorders such as diabetes and metabolic syndrome. As shown in FIG. 1, in the liver aPKC activity can be increased in response to hyperinsulinemia, which can stimulate the production of lipids and other insulin resistant factors that can reduce glucose uptake by muscle cells, which increases blood glucose concentration and further stimulates insulin production. Additionally, increased aPKC in the liver can block Akt, which can increase glucose production by the liver, which can increase blood glucose concentration and further stimulates insulin production. As shown in FIG. 1, in the muscle hyperinsulinemia decreases the expression and/or activity of glucose transporters, which decreases glucose uptake from the blood stream by muscle cells. This increases blood glucose concentration, which can stimulate the production of insulin from islet β-cells and further contribute to hyperinsulinemia.

Previously, it was thought that the brain can become insulin resistant. However, as demonstrated elsewhere herein, the brain is insulin responsive but hyperinsulinemia can result in dysregulation of various signaling pathways, which can be the result of increased aPKC expression in the CNS Also shown in FIG. 1, hyperinsulinemia in the brain can result in increased activity of aPKC isoform, PKC-$\lambda/\iota$ and Akt via stimulation of the IRS 1/2, PI3K pathway. Hyperactivity of these pathways increases production of A$\beta_{1-40/42}$ and p-Tau and decreased PGC-1$\alpha$, which can directly contribute to the development of neurodegenerative disorders, such as AD. In short, hyperinsulinemia in the CNS can result in aberrant signaling, which can be restored to substantially normal by reduction of hyperinsulinemia or direct inhibition of aPKC in the CNS.

The aPKC inhibitors that can cross the blood brain barrier can directly inhibit aPKC in the brain and, inter alia, decrease A$\beta_{1-40/42}$ and p-Tau and increase PGC-1$\alpha$ expression and/or activity, thereby treating and/or preventing a neurodegenerative disorder or a symptom thereof. The aPKC inhibitors that do not cross the blood brain barrier can reduce systemic hyperinsulinemia by their action in the liver and/or muscle. The reduction in hyperinsulinemia reduces stimulation of aPKC and/or Akt in the CNS, which can work to restore normal signaling in the CNS.

The aPKC inhibitors and formulations thereof described herein can be administered to a subject in need thereof. The subject in need thereof can be hyperinsulinemic in the periphery and/or CNS, have diabetes (type 1 or type 2), metabolic syndrome, obesity, a neurodegenerative disorder (e.g. AD) a symptom thereof, or a complication thereof (e.g. high blood sugar and/or cardiovascular disorders). The subject in need thereof can be symptomatic or asymptomatic. In some aspects, the subject in need thereof does not have diabetes, but has a symptomatic or asypomatic neurodegenerative disorder, such as, but not limited to, AD.

The amount of the aPKC inhibitors and formulations thereof delivered to the subject in need thereof can be an amount effective to reduce blood glucose level, reduce hyperinsulinemia in the periphery and/or CNS, decrease phosphorylation an/or activity of Akt, such as in the CNS, directly and/or indirectly decrease activity of aPKC in the CNS, decrease activity of β-secretase in the CNS, decrease the amount of A$\beta_{1-40/42}$ in the CNS, decrease the amount of thr-231-phospho-tau in the CNS, decrease the activity of aPKC isoform PKC-$\lambda/\iota$ in the CNS, decrease p-FoxOs in the CNS, decrease pGSK3β in the CNS, decrease p-mTOR in the CNS, increase the activity of FoxO1, FoxO3a, or FoxO1 and FoxO3a, and/or increase PGC-1$\alpha$ in the CNS. The amount of the aPKC inhibitors and formulations thereof administered to the subject can treat or prevent a neurodegenerative disorder or a symptom thereof. Such neurodegenerative disorders can be, without limitation, AD.

It will be appreciated that "co-administered" or "co-administration" can refer to an additional compound that is included in the formulation or provided in a dosage form separate from the aPKC inhibitor or formulation thereof. The effective amount of aPKC inhibitor or formulation thereof, such as those described herein, can range from about 0.1, 1, 5, 10, 20, 30, 60, 80, 90, 100, 150, 200, 250, 300, 350, 400, or 450 mg/kg to about 500 mg/kg. In some embodiments, the effective amount ranges from about 0.1, 1, 5, 10, 15, 20, 25, 30, 35, 40, 45, 50, 55, 60, 65 mg/kg to 70 mg/kg. In additional embodiments, the effective amount of the aPKC inhibitor or formulation thereof can range from about 100 mg/kg. If further embodiments, the effective amount can range from about 0.1 mg to about 1000 mg. In some embodiments, the effective amount can range from about 500 mg to about 1000 mg. The effective amount in a can range from about 0.1, 1, 5, 10, 20, 30, 40, 50, 60, 70, 80, 90, 100, 150, 200, 250, 300, 350, 400, 450, or 500 mg/kg to about 1000 mg/kg per dose or per day.

Administration of the aPKC inhibitor and/or formulations thereof can be systemic and/or localized. The aPKC inhibitors and formulations thereof described herein can be administered to the subject in need thereof one or more times per day. The aPKC inhibitors and formulations thereof can be administered one or more times per day every other day. In an embodiment, the compound(s) and/or formulation(s) thereof can be administered once daily. The aPKC inhibitors and formulations thereof and/or formulation(s) thereof can be administered given once daily for 1, 2, 3, 4, 5, 6, 7, 8, 9, 10, 11, 12, 13, 14, or more consecutive days. In some embodiments, when administered, an effective amount of the compounds and/or formulations are administered to the subject in need thereof. The compound(s) and/or formulation(s) thereof can be administered one or more times per week. In some embodiments the compound(s) and/or formulation(s) thereof can be administered 1 day per week. In other embodiments, the compound(s) and/or formulation(s) thereof can be administered 2 to 7 days per week.

In some embodiments, the aPKC inhibitor(s) and/or formulation(s) thereof, can be administered in a dosage form. The amount or effective amount of the compound(s) and/or formulation(s) thereof can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 0.1 to about 1000 mg per day. The effective amount in a dosage form can range from about 0.1, 1, 5, 10, 20, 30, 40, 50, 60, 70, 80, 90, 100, 150, 200, 250, 300, 350, 400, 450, or 500 mg/kg to about 1000 mg/kg per dose or per day. The dosage form can be formulated for oral, vaginal, intravenous, transdermal, subcutaneous, intraperitoneal, or intramuscular administration. Preparation of dosage forms for various administration routes are described elsewhere herein.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

Alzheimer's disease (AD) is prevalent in insulin-resistant forms of obesity and type 2 diabetes mellitus (T2DM), and vice versa in the USA. Obesity, the associated metabolic syndrome and T2DM now afflict approximately 50% of people over age 50, and this may explain why AD afflicts approximately 50% of people over age 85. Indeed, in some series, T2DM or "pre-T2DM" is present in 80% of AD patients [1].

As obesity/T2DM generally predates AD, it is thought that systemic insulin resistance abets AD development, and some investigators postulate that the brain itself is insulin-resistant [2-5]. However, in examining brain insulin signaling factors in multiple insulin-resistant obesity/T2DM models [high-fat-fed (HFF) mice [6], ob/ob mice [7], heterozygous muscle-specific PKC-λ knockout (Het-MλKO) mice wherein impaired muscle glucose transport secondarily hyperactivates hepatic aPKC causing hyperexpression of gluconeogenic and lipogenic enzymes [8]), and monkeys with long-standing diet-dependent insulin-resistant obesity/T2DM], it was found that hyperinsulinemia in each model was accompanied by, and apparently responsible for, maximal or near-maximal increases in resting/"basal" activities of the two phosphatidylinositol 3-kinase (PI3K)-dependent protein kinases that mediate most insulin effects, Akt and atypical PKC (aPKC) isoform, PKC-λ/ι [9].

Further, with persistent activation of brain Akt in each obesity/T2DM model, brain FoxOs (1/3a/4/6) were maximally phosphorylated and thereby inhibited, and FoxO1-dependent PGC-1α levels were reduced [9], thus diminishing availability of multiple transcriptional factors needed for memory functions [10] and neuronal integrity [10-16]. Additionally, tau phosphorylation was increased in more-advanced ob/ob and monkey models [9] by a mechanism independent of glycogen synthase kinase-3β (GSK3β), which was inhibited by Akt. Most importantly, both acute insulin treatment of normal mice, and hyperinsulinemia in each insulin-resistant model was accompanied by increases in $A\beta_{1-40/42}$ levels [9]. Moreover, with correction of hyperinsulinemia in the Het-MλKO mouse obesity/T2DM model that follows the reduction of excessive hepatic aPKC activity [elicited by liver-selective aPKC inhibitor, aurothiomalate (ATM), which does not inhibit brain aPKC], all CNS aberrations in Akt, PKC-λ/i, FoxOs, GSK3β, mTOR and $A\beta_{1-40/42}$ reverted to normal, and acute stimulatory effects of exogenous insulin on all of these parameters were restored [9]. This reversal of hyperinsulinemia-induced CNS aberrations and restoration of normal brain insulin signaling suggested that signaling aberrations in untreated animals were provoked by hyperinsulinemia, and, moreover, could abet development of AD pathologies, i.e., phospho-tau "tangles" and β-amyloid plaques.

In this Example, at least the role of insulin-sensitive protein kinases, in particular PKC-ι the role of insulin-sensitive protein kinases was examined for increasing levels of $A\beta_{1-40/42}$ and phospho-tau. To elucidate the mechanism for increases in $A\beta_{1-40/42}$, it was examined whether insulin activates β-secretase. Thus, the findings showing that acute insulin treatment in normal wild-type mice and hyperinsulinemia in Het-MλKO mice can provoke comparable increases in $A\beta_{1-40/42}$, and that liver-selective inhibition of aPKC by aurothiomalate (ATM) in Het-MλKO mice reverses hyperinsulinemia and simultaneously restores normal basal and insulin-stimulated signaling to $A\beta_{1-40/42}$ in the brain was revisited [9]. However, instead of using ATM, which inhibits all aPKCs (PKC-λ/ι/ζ) [8,16], but does not cross the blood brain barrier (BBB) to alter brain aPKCs in doses that satisfactorily inhibit liver aPKC to reverse hyperinsulinemia [8,9], a PKC-Ah-specific inhibitor, [1H-imidazole-4-carboxamide,5-amino]-[2,3-dihydroxy-4-[(phosphono-oxy)methyl]cyclopentane-[1R-(1a,2b,3b,4a)] (ICAPP), which selectively inhibits PKC-λ/ι in both liver and brain. It was observed that, like ATM, ICAPP, by inhibiting liver aPKC and thereby correcting hyperinsulinemia [8] and all hyperinsulinemia-induced signaling aberrations seen basally in brains of Het-MλKO mice and was observed to block acute stimulatory effects of insulin on PKC-λ/ι activity, β-secretase activity and $A\beta_{1-40/42}$ production. Another inhibitor of aPKC, 2-acetyl-cyclopentane-1,3-dione, (ACPD), which, like ICAPP, can cross the BBB, and, in HFF mice, ACPD was observed to not only diminished brain PKC-A/i activity, $A\beta_{1-40/42}$ production and thr-231-tau phosphorylation, but, additionally, was observed to improve an impairment in memory function induced by HF feeding and production of an insulin-resistant state. Finally, at least the stimulatory effects of insulin and other aPKC activators, metformin and constitutive PKC-ι, on β-secretase activity and $A\beta_{1-40/42}$ production in isolated neurons was examined and similarly it was observed that PKC-Ah can cause increases in these parameters as induced by these aPKC activators.

Materials and Methods aPKC Inhibitors. 1H-imidazole-4-carboxamide,5-amino]-[2,3-dihydroxy-4-[(phosphono-oxy)methyl]cyclopentane-[1R-(1a,2b,3b,4a)] (ICAPP) was identified as a potential aPKC inhibitor by high throughput screening (HIS) of a chemical library for virtual docking with the crystallographic structure of PKC-ι catalytic domain, custom-synthesized by the Southern Research (Birmingham, AL), and found to preferentially inhibit recombinant PKC-ι [26]. Because of cost and limited availability, ICAPP is now used primarily in isolated cells, and more recently, particularly in long-term in vivo studies, 2-acetyl-cyclopentane-1,3,-dione (ACPD), which was similarly identified by the same HTS has been used, purchased from Sigma (St Louis, MO), and found to inhibit recombinant PKC-ι and PKC-ζ with equal potency [6,7]. Neither ICAPP [8] nor ACPD [6,7] inhibit conventional PKCs, novel PKCs, AMP-dependent protein kinase and Akt; and ACPD had no effect on a battery of protein kinases, including, Akt2, FGFR1/2/3/4, mTOR, GSK3, IRAK1/4, JAK1/2, MEK1, ERK1/2, JNK1/2, PKA, Src, ROCK2, ROS1, or PI3Kα/α as tested by Life Technologies (Madison WI, USA) [7].

Mouse Studies. Brain samples were obtained from normal and insulin-resistant mice and monkeys used previously [9], and includes mice originally used in studies of insulin signaling and resistance in liver: (a) 4-6 month old C57Bl/6 mice used in studies of high-fat-feeding [USF Vivarium] [6]; 4-6 month-old male C57Bl/6 ob/ob and lean ob+ mice (Jackson Labs, Bar Harbor, Maine) [7]; and (c) 10-12 month-old C57Bl/6 Het-MλKO mice [USF Vivarium] [8]. Males and females were comparably present in experimental groups, and sex didn't appreciably alter combined findings. Hepatic alterations, clinical characteristics and ameliorating effects of liver-selective aPKC inhibitors were reported previously [6-8]. Mice were housed in environmentally-controlled rooms and fed standard mouse chow supplying 10% of calories from fat, or diets supplying either 40% or 60% of calories from fat (Harlan Industries, Madison, Wisconsin) (results in mice consuming these HF diets were comparable and thus combined [9]). Where indicated, Het-MλKO were injected subcutaneously (SC) once daily for 8 days with saline or 1H-imidazole-4-carboxamide,5-amino]-(2,3-dihydroxy-4-[(phosphono-oxy)methyl]cyclopentane-[1R-(1a,2b,3b,4a)] (ICAPP) 0.4 mg/kg body weight) in saline, to inhibit hepatic aPKC, and thus diminish aPKC-dependent expression of hepatic gluconeogenic and lipogenic enzymes, and thereby reduce serum insulin levels to near-normal [8]. Where indicated normal mice were given a single SC injection of saline or saline containing 1.5 mg/kg ICAPP to follow time-related alterations in brain signaling factors. Where indicated, mice were treated intraperitoneally (IP) with insulin (1 U/kg body weight) or vehicle 15-min before euthanization by administration of Xylazine/Ketamine, followed by whole body perfusion with phosphate-buffered saline and rapid removal of brain and other tissues.

Note that, in accordance with an earlier report showing that insulin signaling responses in whole brain largely occur in neurons, rather than glial or endothelial cells, most notably, in the hippocampus and hypothalamus [26], it was previously documented that activating effects of insulin were readily seen in neurons of the anterior cortex and hippocampus [9], and measurements of total brain insulin signaling correlated well with alterations in these individual neurons, both in normal and insulin-resistant HFF and ob/ob mice [9].

All experimental procedures involving mice were approved by the Institutional Animal Care and Use Committees (IACUCs) of the USF-COM or Roskamp Institute, and the James A. Haley Veterans Administration Research and Development Committee.

Monkey Studies. As described [9], brains were obtained immediately post-mortem from 16-30 year old male and female lean non-diabetic and obese/T2D *Macaca mulatta* rhesus monkeys; note that obesity and T2D were present for many years; see [9] for further details. Euthanitization was initiated with ketamine-HCl (10-15 mg/kg body weight) followed by intravenous Euthasol (0.22 ml/kg body weight). Anterior cortical samples of monkey brains were taken and stored at −150° C. Experimental procedures involving monkeys, including euthanitization, were approved by USF-COM IACUC.

Tissue Preparations. As described [9], mouse brains were hemisected sagittally, and one-half was frozen in liquid $N_2$, stored at −80° C., and samples thereof were homogenized in buffer containing 0.25M sucrose, 20 mM Tris/HCl (pH, 7.5), 2 mmol/l EGTA, 2 mM EDTA, 1 mM phenlysulfonoylfluoride (PMSF), 20 µg/ml leupeptin, 10 µg/ml aprotinin, 2 mM Na4P2O7, 2 mM Na3VO4, 2 mM NaF, and 1 µM microcystin, and then supplemented with 1% TritonX-100, 0.6% Nonidet and 150 mM NaCl.

β-Secretase Activity (BACE1; beta-site APP-cleaving enzyme-1). β-Secretase was measured was measured using a kit from Thermo-Fisher.

Western Analyses. As described [9], Western analyses were conducted with rabbit antisera or mouse monoclonal antibodies (mMab), using: anti-aPKC (Santa Cruz Biotechnologies, Santa Cruz, CA); anti-phospho-threonine-560/555-PKC-ζ/λ/ι (Invitrogen, Carlsbad, CA); anti-p-serine-256-FoxO1 and anti-FoxO1 (Abnova, Walnut, CA); anti-Akt (mMab), anti-phospho-serine-473-Akt, anti-phospho-serine-9-GSK3P anti-GSK313, anti-phospho-serine-253-FoxO3a, anti-FoxO3a, anti-phospho-serine-256-FoxO1, anti-phospho-serine-193-FoxO4; anti-FoxO1, anti-phospho-serine-2448-mTOR, anti-mTOR, anti-β-amyloid (anti-5-10 kDa-A$β_{1-40/42}$) and anti-amyloid precursor protein (anti-120 kDa-APP) (Cell Signaling Technologies, Danvers, MA); and anti-phospho-serine-202-tau, anti-phospho-threonine-231-tau (Gene Tex, Irvine, CA). Samples from experimental groups were compared on the same blots, and routinely checked with loading controls. Note that: insulin-sensitive 70 kDa aPKC is largely PKC-ζ in mouse brain and orthologous PKC-ι (98% aa homology) in monkey and other primate brains; brain PKC-ζ exists largely as a 50 kDa moiety that, lacking a regulatory domain, is constitutively-active and unresponsive to insulin.

Novel Object Recognition Testing. This test is dependent on neuronal activity in cortical areas of the para-hippocampal region of the temporal lobe, and was conducted as described (29). In brief, after acclimation to handling for three consecutive days, and then to daily placements in a chamber for another 3 days, the mice were then placed for 5-min in the same chamber containing two copies of an object to allow familiarization, and, 3 hours later, returned for 5-min to the same chamber containing one copy of the initial/familiar object and one copy of a new object. As mice are innately drawn to explore new versus familiar objects, the ratio of time spent exploring the novel object to time spent exploring the initial/familiar object (measured by camera and computer analysis) serves as an index of acute visual memory of the initial/familiar object.

Statistical Analyses. Data were expressed as mean±SEM, and compared using one-way ANOVA and Tukey post hoc test for analysis of significance.

Results

Alterations in Akt Activity in Untreated and ICAPP-treated Het-MλKO Mice.

Figure 4A:
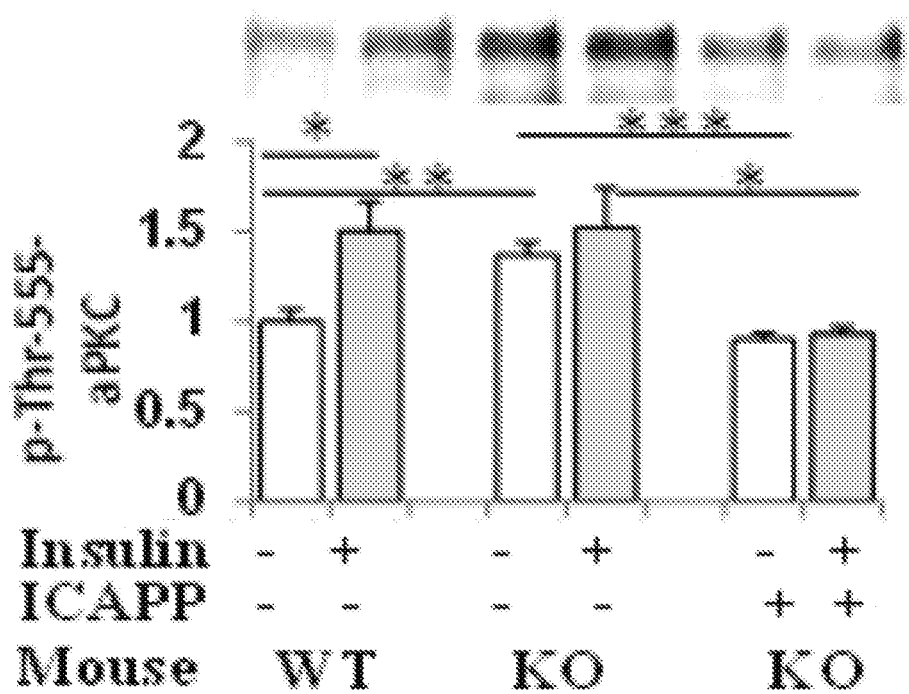
FIGS. 4A-4G show graphs that can demonstrate hepatic aPKC inhibitor ICAPP can reverse hyperinsulinemia-induced increases in basal/resting PKC-λ/ι activity (FIG. 4A), p-Ser-473-Akt activity (FIG. 4B), p-Ser-256-FoxO1 (FIG. 4C), $A\beta_{1-40/42}$ peptide production (FIG. 4D), phosphorylation of Akt substrates, ser-2448-mTOR (FIG. 4F), ser-253-FoxO3a (FIG. 4E), and ser-9-GSK3β (FIG. 4G) in brains of insulin-resistant Het-MλKO (KO) mice. Where indicated, PKC-λ/ι inhibitor, ICAPP (0.4 mg/kg body weight), was administered subcutaneously once daily for 8 days, and insulin (1 U/kg body weight) (shaded bars) was administered intraperitoneally 15-min before killing. Representative Western blots of indicated proteins are shown; loading control levels, which were not altered, are not shown. Relative bar values are mean±SEM of 6 mice. Asterisks: *, $P<0.05$; , $P<0.01$; *, $P<0.001$ (ANOVA).
Figure 4B:
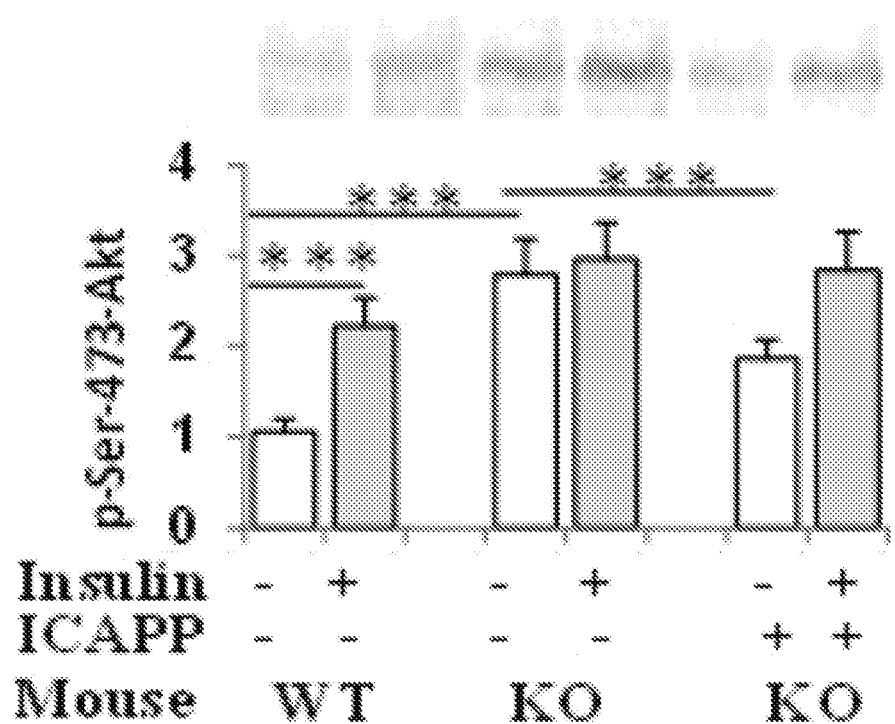
Figure 4C:
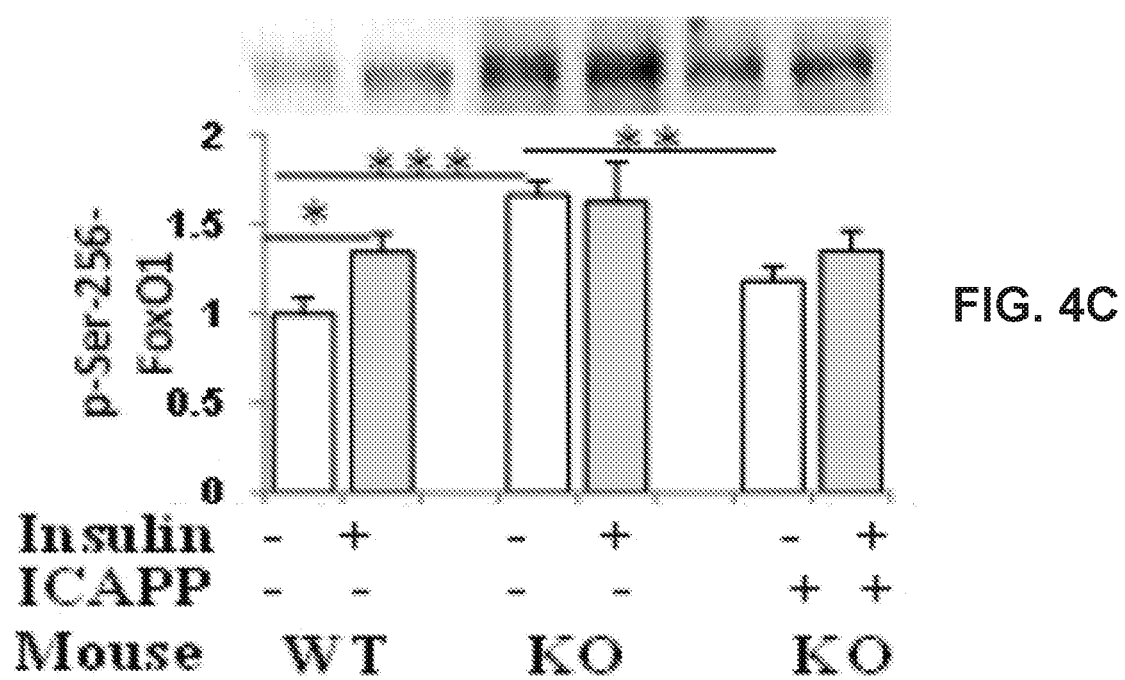
Figure 4D:
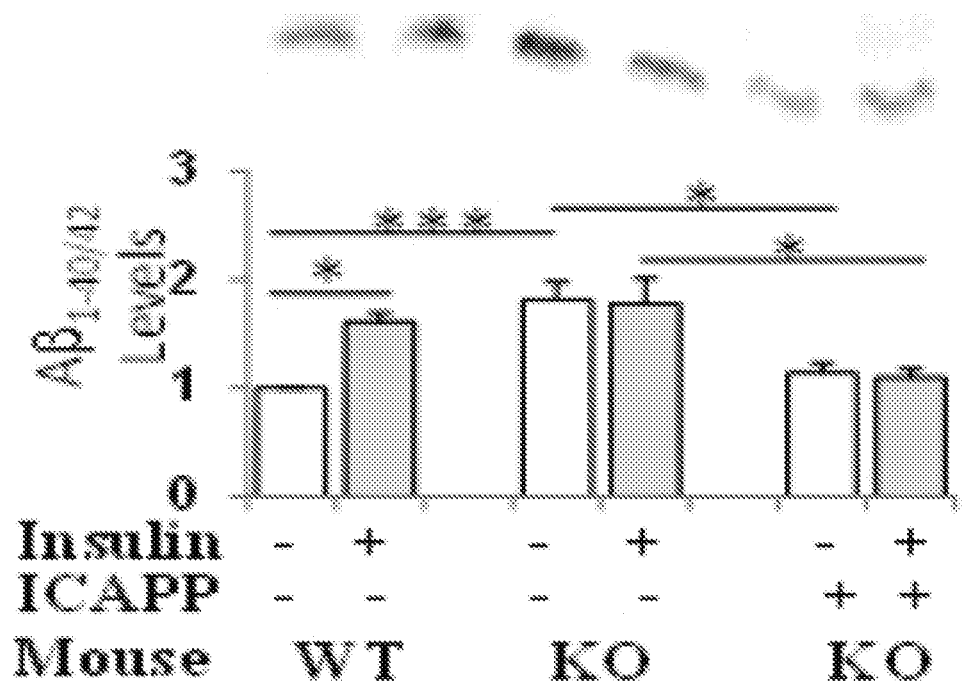
Figure 4E:
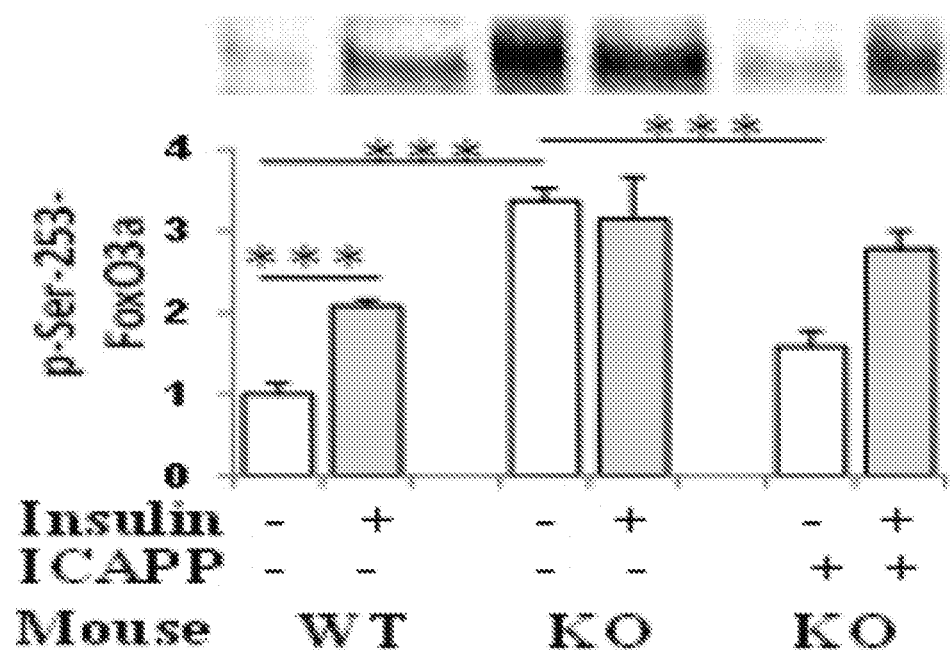
Figure 4F:
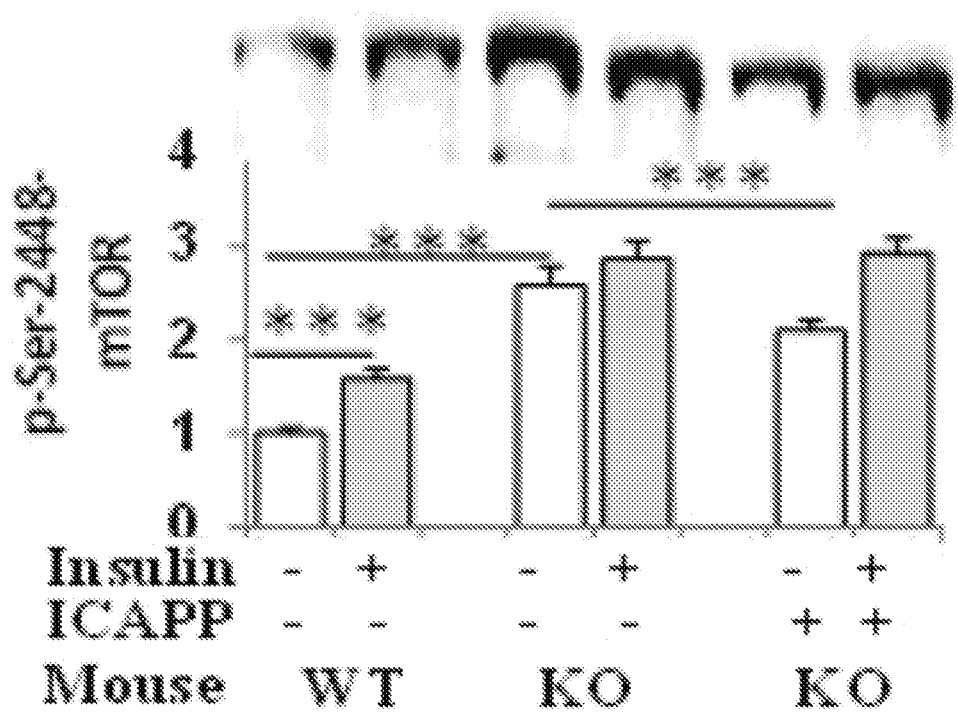
Figure 4G:
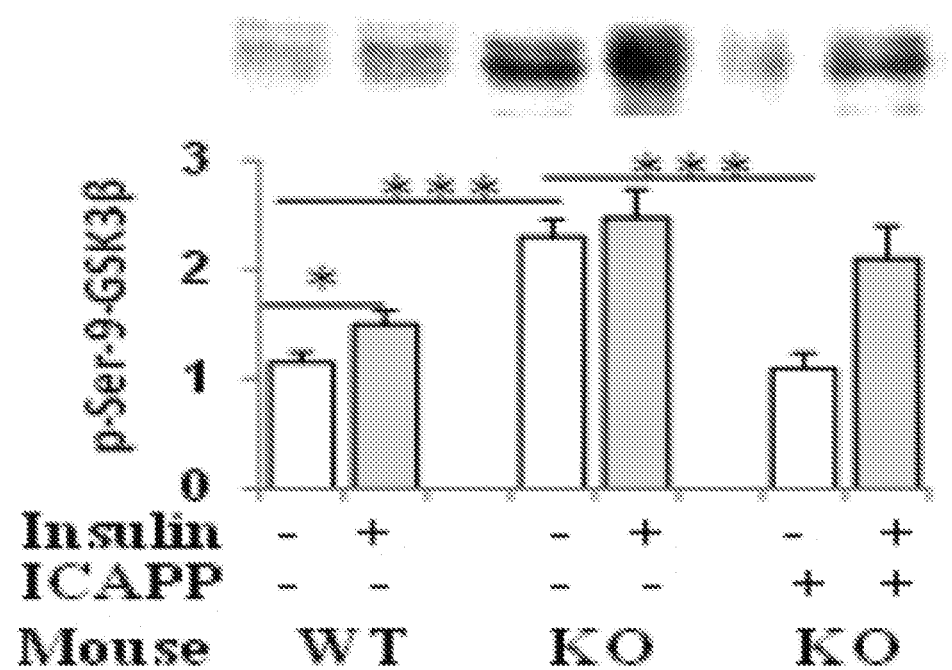

As reported [9], Akt activity (FIG. 1a) and the phosphorylation of its substrates, mTOR (FIG. 4B), FoxO3a (FIG. 4E) and GSK3β (FIG. 4G) were increased by acute 15-min insulin treatment in normal wild-type (WT) mice, and to apparently similar maximal levels in the resting/"basal" state in Het-MλKO mice, as acute insulin treatment was without further effect in these mice. Further, as with ATM treatment [9], which inhibits liver, but not brain, aPKC and thereby corrects systemic insulin resistance and hyperinsulinemia [8], 8-day treatment of Het-MλKO mice with ICAPP diminished resting/basal Akt activity (FIG. 4B) and phosphorylation of Akt substrates (FIG. 4E), and this was attended by restored ability of insulin to acutely activate Akt (FIG. 4B) and increase phosphorylation of its substrates (FIGS. 4B, 4E, and 4G). These improvements in brain Akt signaling presumably reflected correction of hyperinsulinemia [8] elicited by inhibitory effects of ICAPP on hepatic PKC-λ/ι and consequent decreases in expression of hepatic gluconeogenic and lipogenic enzymes [8,16].

Alterations in PKC-λ/ι Activity and A$β_{1-40/42}$ Levels in Untreated and ICAPP-treated Het-MλKO mice. As with Akt activity, ICAPP diminished resting/basal activity of insulin-sensitive 70 kDa PKC-λ/ι in brains of Het-MλKO mice (FIG. 4A). However, in marked contrast to the restoration of the ability of insulin to activate Akt, ICAPP blocked the ability of insulin to activate PKC-λ/ι in in Het-MλKO mice (FIG. 4A). Further, the loss of insulin effects on PKC-λ/ι activity in ICAPP-treated Het-MλKO mice was accompanied by a comparable loss in the ability of insulin to acutely increase A$β_{1-40/42}$ levels (FIG. 4D).

Figure 7:
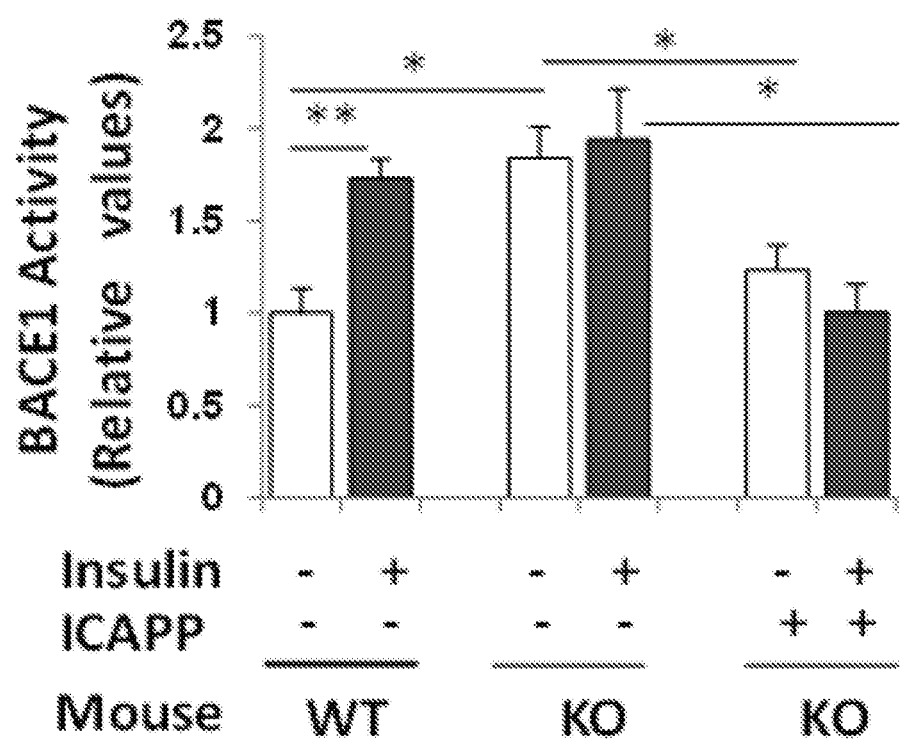
FIG. 7 depicts activation of BACE1 by insulin (1 U/kg-bw, IP, 15-min) in normal WT mice and by hyperinsulinemia in Het-MλKO mice, and blockade by aPKC inhibitor ICAPP (0.4 mg/kg-bw/day×8 days). Values are Mean±SEM of 6 mice. Asterisks: *, $P<0.05$; **, $P<0.01$ (ANOVA).
Figures 8A, 8B, 8C:
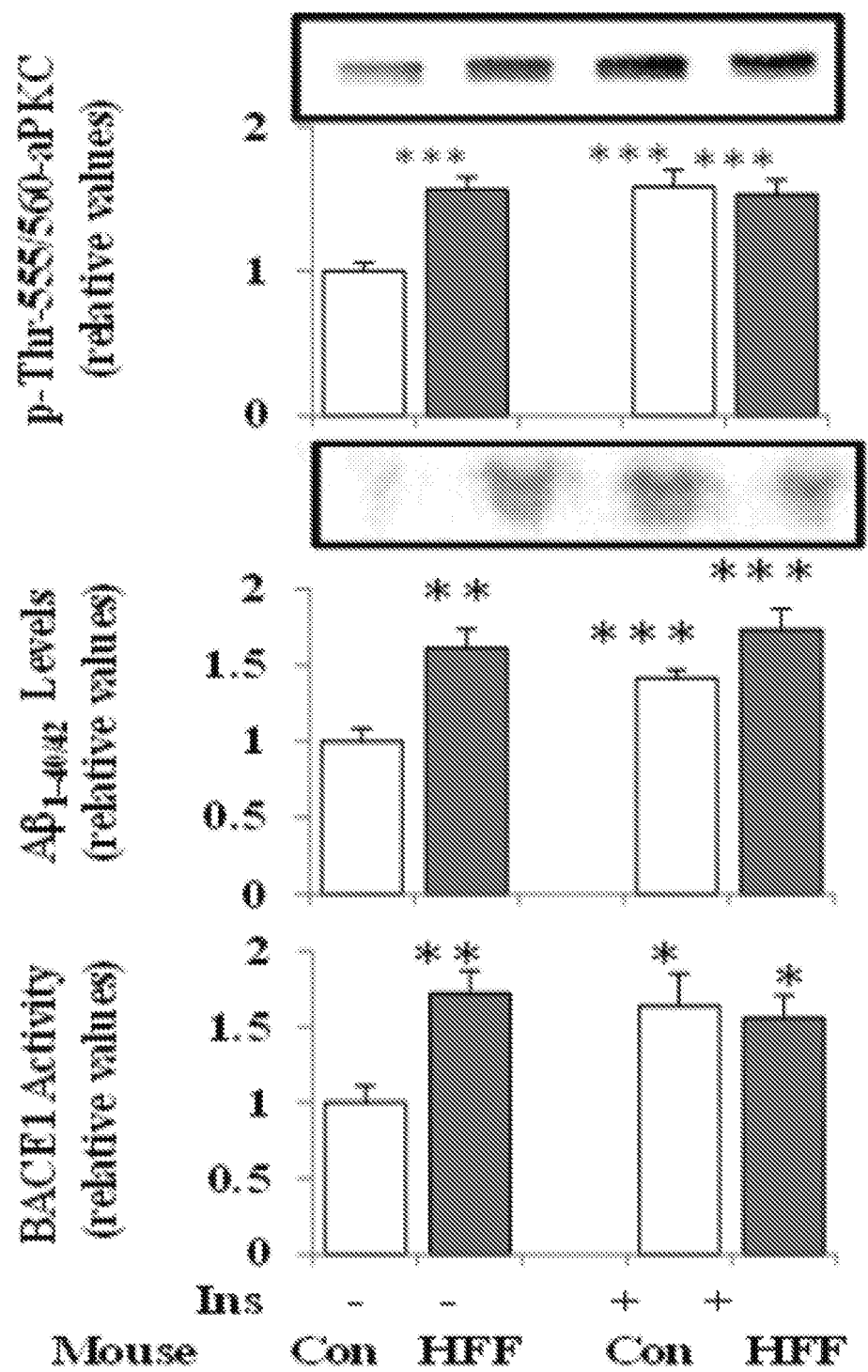
FIGS. 8A-8C depicts activation of CNS aPKC activity (FIG. 8A), $A\beta_{1-40/42}$ peptide production (FIG. 8B), and BACE1 activity (FIG. 8C) by insulin in chow fed control (Con) and by hyperinsulinemia in high fat-fed (HFF) mice. IP insulin (Ins) treatment: 1 U/kg-bw. Mean±SEM of 6 mice. Asterisks: *, $P<0.05$; , $P<0.01$; *, $P<0.001$.

Alterations in β-Secretase Activity in Untreated and ICAPP-Treated Het-MλKO Mice Next β-secretase was focused on, which initiates proteolytic release of A$β_{1-40/42}$ from β-amyloid precursor protein (p-APP). As with $A\beta_{1-40/42}$ levels (FIG. 4D), acute insulin treatment in normal WT mice and chronic hyperinsulinemia in Het-MλKO mice were accompanied by increases in brain β-secretase activity (BACE1) (FIG. 7). More importantly, ICAPP treatment reduced resting/basal β-secretase activity to near-normal levels, and fully blocked acute insulin-stimulated increases in β-secretase activity in brains of Het-MλKO mice (FIG. 7).

Figure 23A:
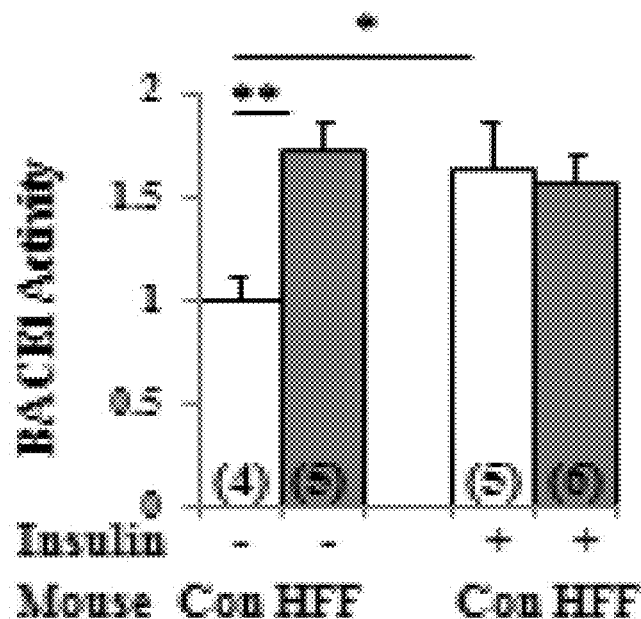
FIGS. 23A-23C show graphs that can demonstrate activation of brain β-secretase activity (BACE1) by insulin (1 U/kg body weight) administered intraperitoneally 15-min before killing (shaded bars) of control chow-fed (FIG. 23A) and lean (ob+) control (Con) mice (FIG. 23B), and activation of brain β-secretase (BACE1) by hyperinsulinemia in high fat-fed (HFF) mice (FIG. 23A), ob/ob mice (b), and obese/type 2 diabetic (T2DM) monkeys (FIG. 23C). Relative bar values are mean±SEM of (N) mice or monkeys. Asterisks: *, P<0.05; **, P<0.01; P<0.001 (ANOVA).
Figure 23B:
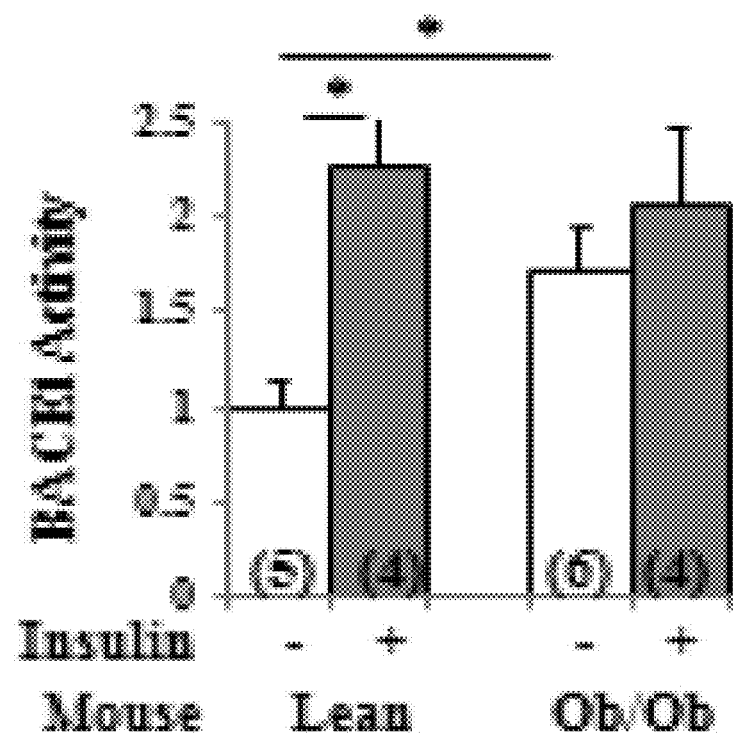
Figure 23C:
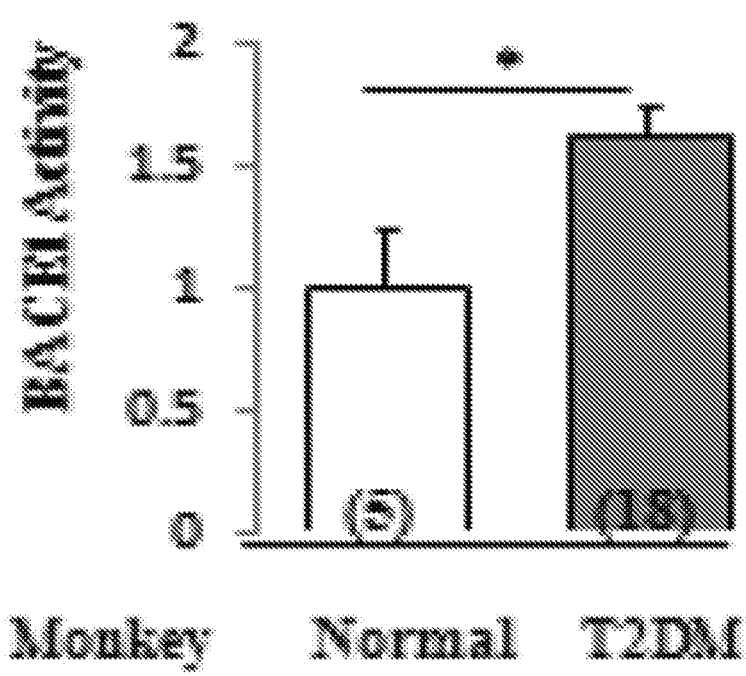

Alterations in β-Secretase Activity in HFF and Ob/OB Mice and Obese/T2D Monkeys. It was previously reported that (a) brain $A\beta_{1-40/42}$ levels are increased acutely by insulin in normal mice and by hyperinsulinemia in HFF and ob/ob mice, and obese/T2D monkeys [9]; (b) β-APP levels are not altered in insulin-resistant mice models [9]; and (c) in monkeys with long-standing obesity and T2DM, in conjunction with increases in $A\beta_{1-40/42}$ peptides, there are modest but significant decreases in p-APP [9], suggesting that increases in $A\beta_{1-40/42}$ were occurring at the expense of β-APP, which, over time, was measurably decreased. Coincident with this idea, acute insulin treatment in normal chow-fed and lean ob+ control mice, and hyperinsulinemia in HFF mice (FIG. 23A), ob/ob mice (FIG. 23B) and obese/T2D monkeys (FIG. 23C), were accompanied by apparently maximal or near-maximal increases in resting/basal β-secretase activity.

Figure 5A:
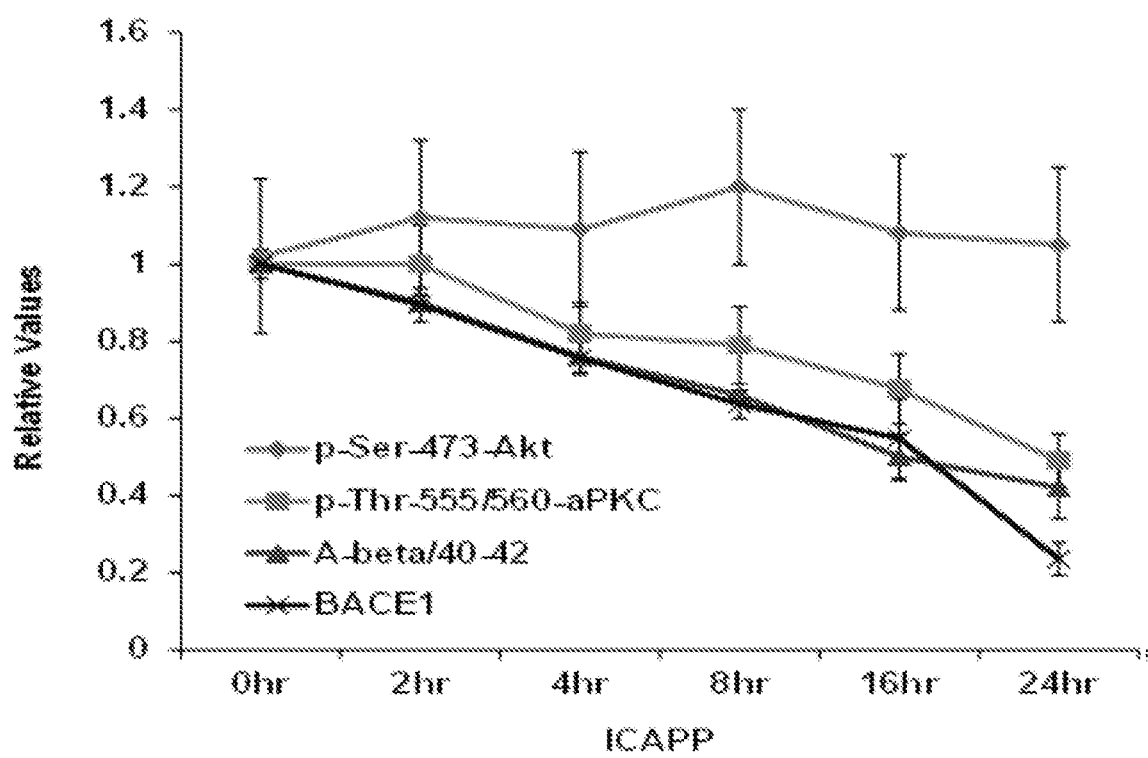
FIGS. 5A-5B shows a graph (FIG. 5A) and an image of a representative blot (FIG. 5B) that can demonstrate that ICAPP (at about 0.5 mg/kg-bw; given SC) can provoke time-related decreases in CNS insulin-stimulated aPKC activity (squares), BACE1 (β-secretase) activity ("x") and $A\beta_{1-40/42}$ peptide production (triangles), but can spare Akt activation (circles). ICAPP (1.5 mg/kg body weight) was administered subcutaneously as a single dose at zero time, and at indicated times, insulin (1 U/kg body weight) was administered intraperitoneally 15-min before killing. Results in insulin-stimulated samples were compared to results in vehicle-injected control mice (see FIGS. 4A-4G, 7, and 25A-25C for comparison of control and insulin-stimulated values). Values are Mean±SEM (N=3-6).
Figure 5B:
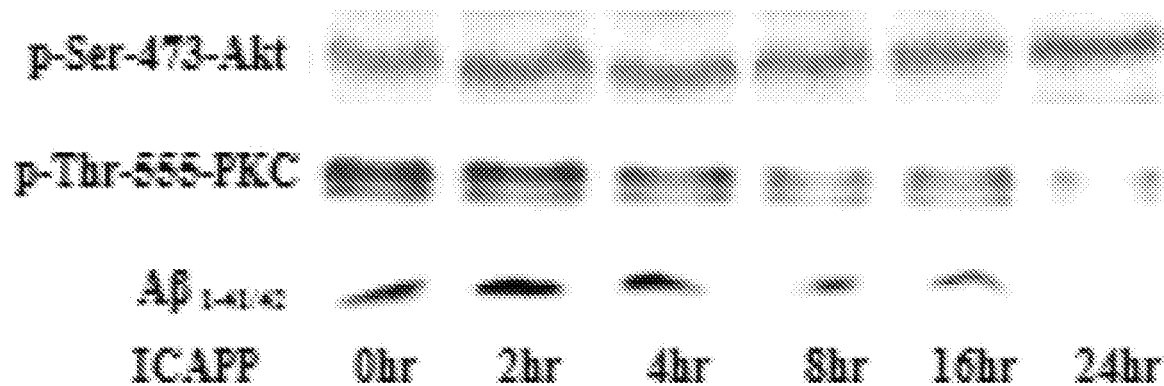

Alterations in PKC-M Activity, β-Secretase Activity and $A\beta_{1-40/42}$ Levels in Untreated and ICAPP-treated Normal Mice. In addition to findings suggesting PKC-λ/ι-dependence of β-secretase activation in Het-MλKO mice, we found in normal mice that administration of a single dose of PKC-λ/ι inhibitor ICAPP provoked time-related, well-correlated decreases in insulin-dependent PKC-λ/ι activity, β-secretase activity and $A\beta_{1-40/42}$ peptide levels, without altering insulin-stimulated increases in Akt activity (FIGS. 5A-5B).

Figures 24A, 24B, 24C, 24D, 24E, 24F:
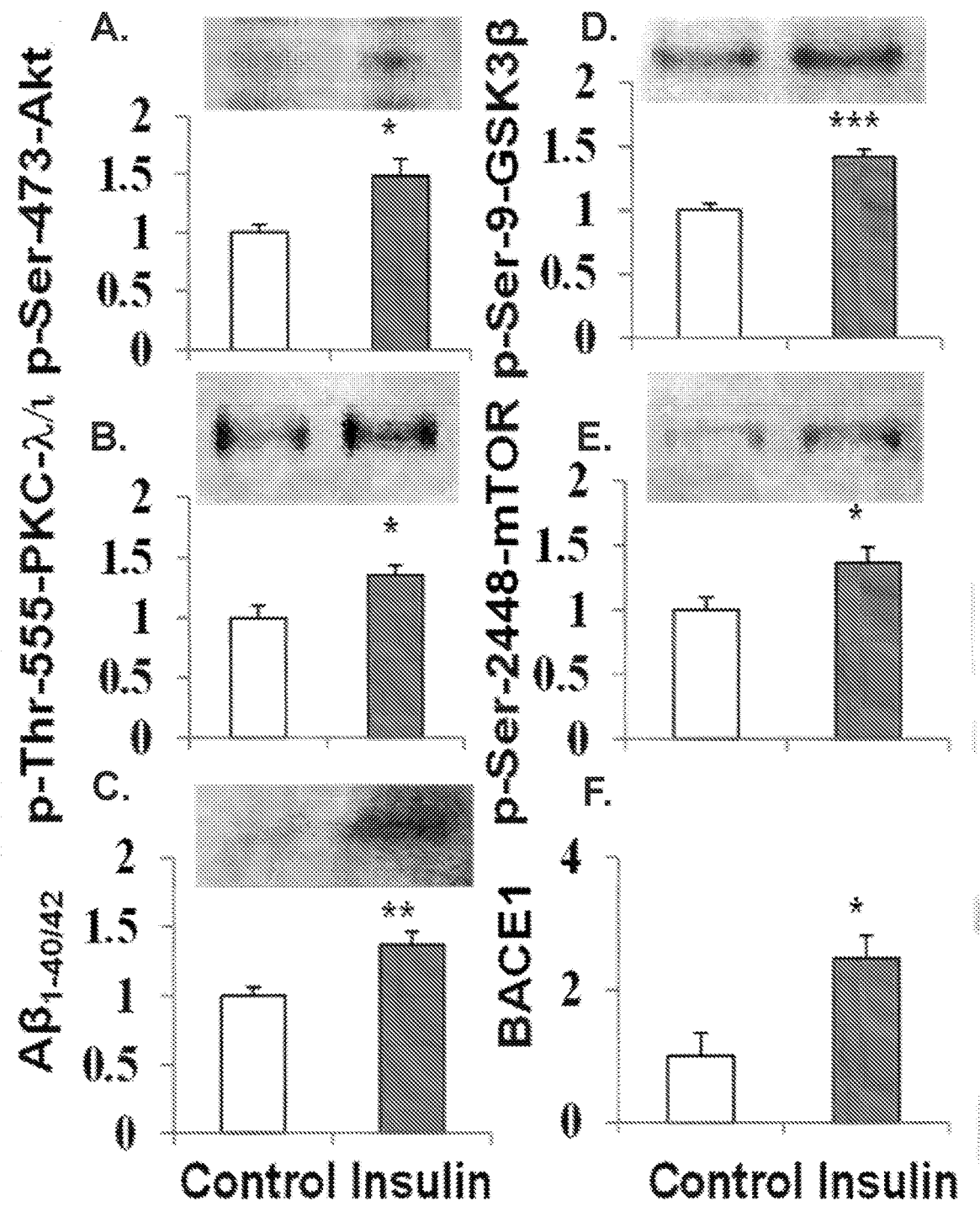
FIGS. 24A-24G show graphs and images that can demonstrate the effect(s) of insulin and ICAPP on aPKC and Akt activities, phosphorylation of Akt substrates (GSK3β and mTOR), β-secretase activity (BACE1) and $A\beta_{1-40/42}$ peptide levels in LA1-5s human neuroblastoma cells. Effects of 24-hour treatment with or without 200 nM insulin are shown in FIGS. 24A-24F, and dose-related effects of ICAPP on insulin-stimulated parameters are shown in FIG. 24G. Relative bar values in panel a are mean±SEM of 6 determinations. Asterisks: *, P<0.05; , P<0.01; *, P<0.001 (ANOVA). Values in panel b are means of 2-4 determinations.
Figure 24G:
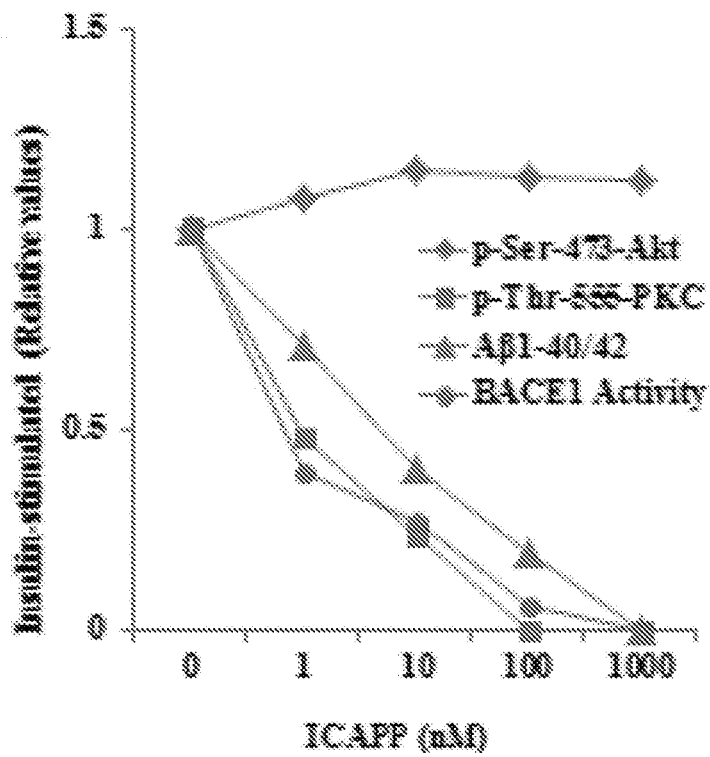

Effects of Insulin and ICAPP on Akt, PKC-M, and 13-Secretase Activity and $A\beta_{1-40/42}$ Levels in Cultured Neuronal Cells. In concert with findings in brains of normal mice, 24-hour insulin treatment elicited increases in: activities of Akt and aPKC; phosphorylation of Akt substrates, GSK3β and mTOR; activity of β-secretase; and levels of $A\beta_{1-40/42}$ in cultured LA1-5s human neuroblastoma neuronal cells (FIGS. 24A-24F). Further, in these cells, ICAPP provoked dose-dependent decreases in insulin-stimulated aPKC activity, 8-secretase activity and $A\beta_{1-40/42}$ levels, without altering stimulatory effects of insulin on Akt activity (FIG. 24G) and phosphorylation of Akt substrates (not shown). Dose-dependent inhibitory effects of ICAPP on insulin-stimulated aPKC activity in these neuronal cells were similar ($IC_{50}$, approximately 1-10 nM) to those previously seen in isolated human hepatocytes, mouse adipocytes and recombinant PKC-λ/ι [8,16].

Figure 25A:
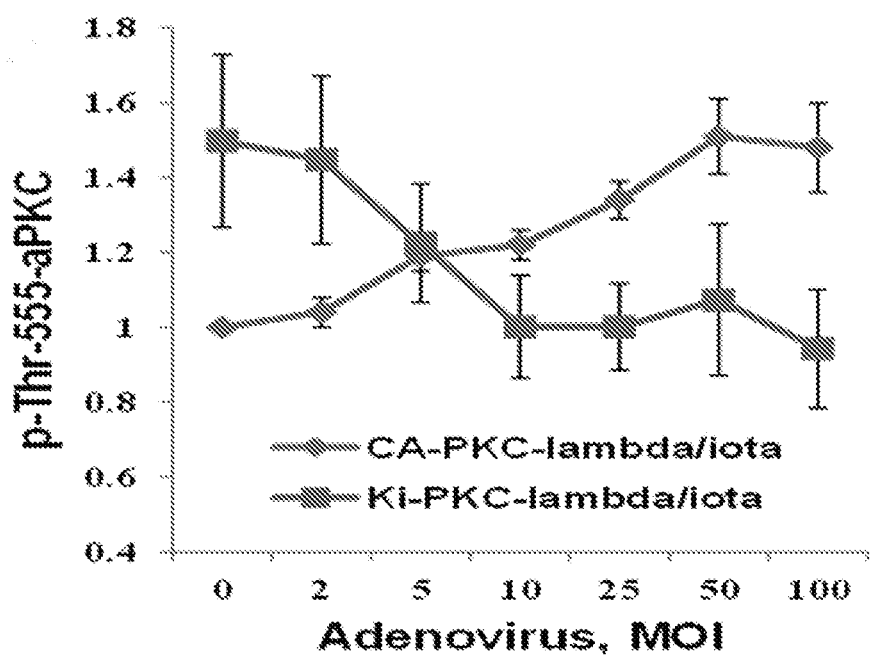
FIGS. 25A-25D show graphs that can demonstrate that adenovirus (Adv) encoding constitutively active (CA) PKC-λ/ι (diamonds) dose-relatedly phosphorylates/activates total aPKC (FIG. 25A) and increases phospho-tau levels (FIG. 25B), δ-secretase activity (BACE1) (FIG. 25C), and $A\beta_{1-40/42}$ levels (FIG. 25D) in LA1-5s human neuroblastoma cells. Adv-encoding kinase-inactive (KI) PKC-λ/ι (squares) dose-relatedly blocks effects of 200 nM insulin on these parameters. Cells were incubated for 48 hours with (squares) and without (diamonds) 200 nM insulin and indicated Adv, the total level of which kept constant at 100 MOI for all samples by adding non-coding Adv. Shown here are Mean±SEM (N=4) values relative to the mean initial basal or insulin-stimulated level of indicated immunoreactive protein/peptide.
Figure 25B:
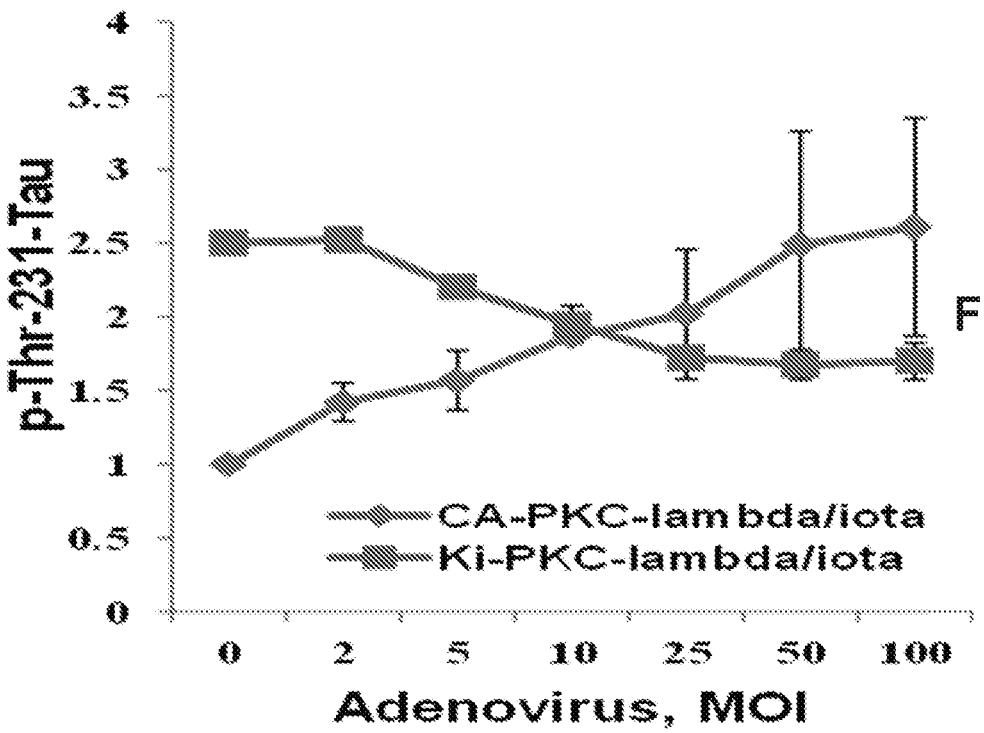
Figure 25C:
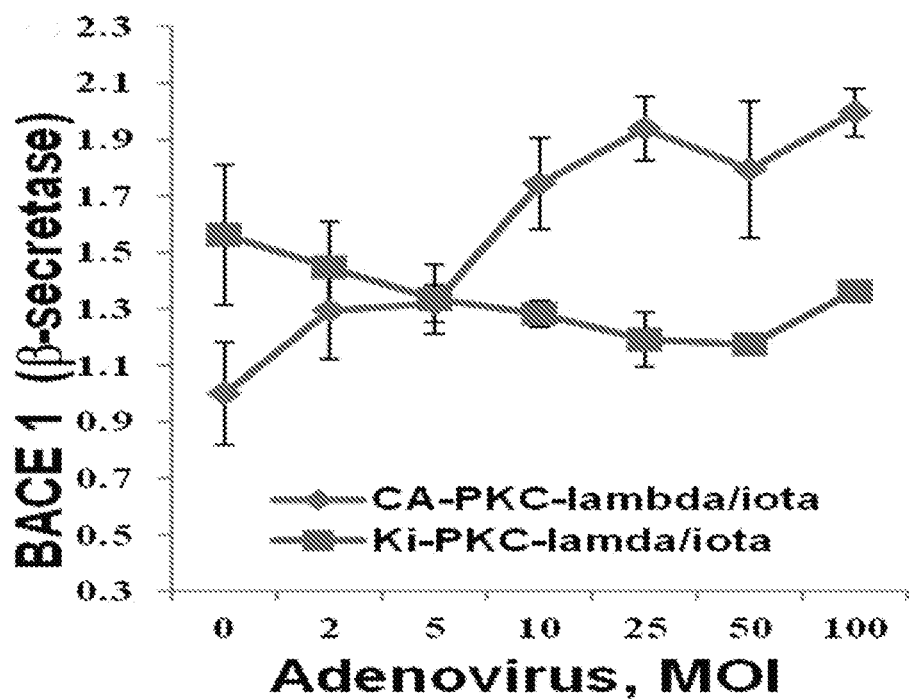
Figure 25D:
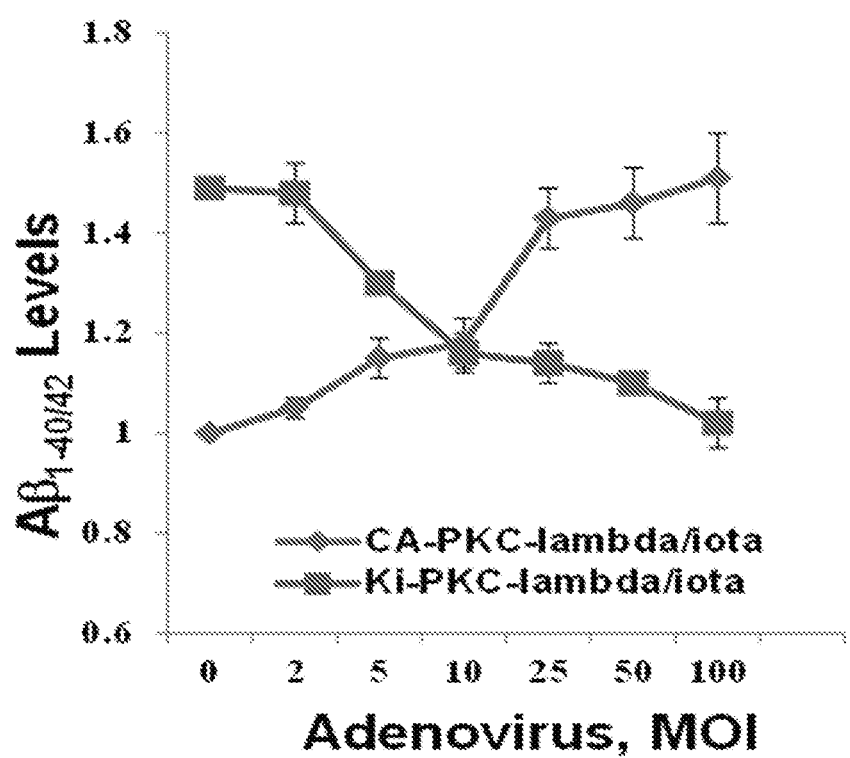

Effects of Adenovirally-mediated Expression of Constitutively-active and Kinase-inactive PKC-ι on Basal and Insulin-stimulated PKC-ι Activity, p-thr-231-Tau, β-Secretase Activity (BACE1) and $A\beta_{1-40/42}$ Levels in Cultured Neuronal Cells. As, in addition to aPKC, insulin activates other signaling factors, it was observed that constitutively-active (CA) PKC-ι provoked insulin-like increases in aPKC activity (FIG. 25A), β-secretase activity (FIG. and $A\beta_{1-40/42}$ levels (FIG. 25C), without altering basal levels and insulin-stimulated increases in Akt activity (latter data not shown), in cultured neuronal cells. Further, as chemical inhibitors may target unintended factors, it was important to find that expression of kinase-inactive (KI) PKC-ι blocked the stimulatory effects of insulin on aPKC activity (FIG. 275), phospho-thr-231-tau (FIG. 25B), β-secretase activity (FIG. 25C) and $A\beta_{1-40/42}$ levels (FIG. 25D).

Effects of Metformin and ICAPP on PKC-ι Activity, β-Secretase Activity (BACE1), $A\beta_{1-40/42}$ Levels, and p-thr-231-Tau Levels in Cultured Nuronal Cells.

Figures 26A, 26B, 26C, 26D, 26E:
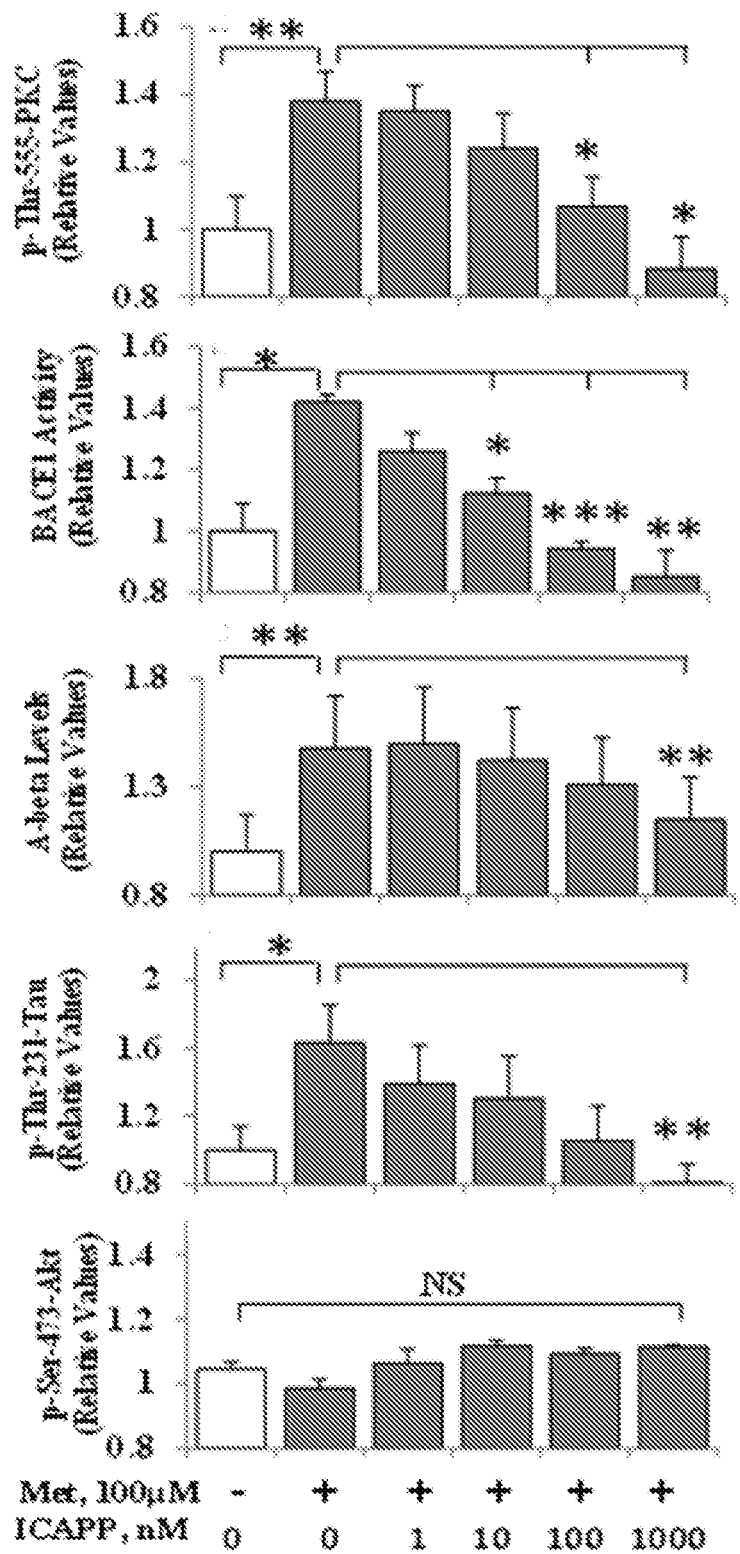
FIGS. 26A-26E show graphs that can demonstrate that Metformin activates aPKC (FIG. 26A), and increases β-secretase activity (BACE1) (FIG. 26B), A-beta ($A\beta_{1-40/42}$) levels (FIG. 26C), and phospho-thr-231-tau levels (FIG. 26D), but not Akt activity (FIG. 26E) in LA1-5s human neuroblastoma cells, and PKC-λ/ι inhibitor, ICAPP, dose-relatedly blocks metformin-induced increases in aPKC activity, β-secretase activity (BACE1), and levels of $A\beta_{1-40/42}$ and phospho-thr-231-tau. Shown here are Mean±SEM (N=4) values relative to the mean initial basal or insulin-stimulated level of indicated immunoreactive protein/peptide. Asterisks: *, P<0.05; , P<0.01; *, P<0.001 (ANOVA).

In addition to insulin and constitutive PKC-ι, aPKC activator, metformin, which reportedly activates β-secretase and increases $A\beta_{1-40/42}$ in isolated neuronal cells and intact mouse brain [17], was also found to increase activity of aPKC (FIG. 26A), but not Akt (FIG. 26E), and simultaneously increase β-secretase activity ((FIG. 26B), and levels of $A\beta_{1-40/42}$ (FIG. 26C) and phospho-thr-231-tau (FIG. 26D) in isolated neuronal cells; and, more importantly, ICAPP dose-dependently inhibited each of these metformin effects.

Figure 27A:
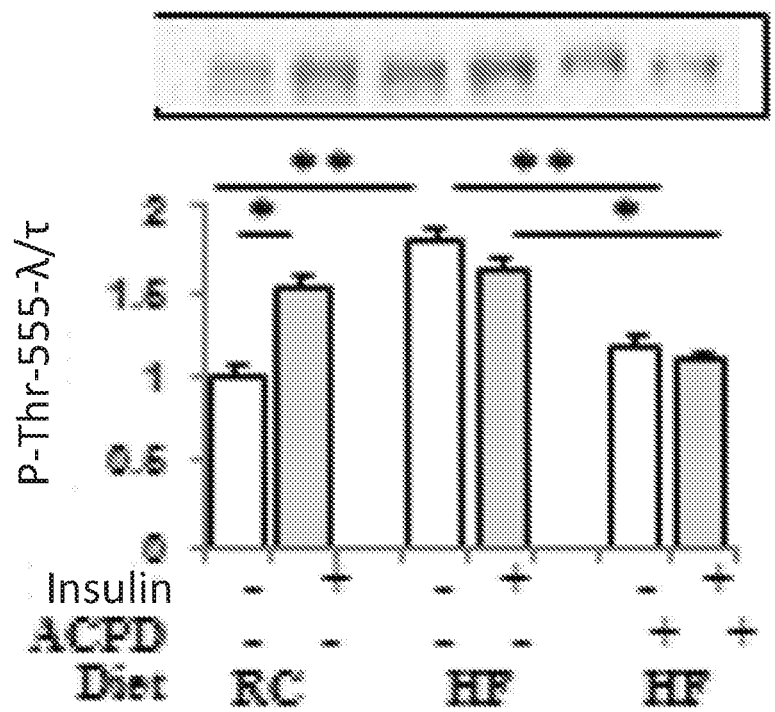
FIGS. 27A-27F show graphs and representative blots that can demonstrate that treatment of high-fat mice with a PKC inhibitor, ACPD, can reduce resting/basal increases in 70 kDa PKC-10 (FIG. 27A), $A\beta_{1-40/42}$ levels (FIG. 27D), and phospho-thr-231-tau (FIG. 27F), and simultaneously reverses/prevents a memory defect in novel recognition (FIG. 27C), without affecting high-fat-diet-induced elevations in Akt activity (FIG. 27B) or PKM-ζ activity (FIG. 27E). Mice were fed regular chow (RC) or a high fat (HF) diet, and treated ±ACPD (20 mg/kg body weight) or vehicle every Monday, Wednesday and Friday of each week for 10 consecutive weeks. Novel object recognition testing was conducted at week 9. At 10 weeks, mice were treated acutely ±insulin (1 U/kg body weight) or vehicle 15 min before killing. Mean values ±SEM (N=4). Asterisks: *, P<0.05; , P<0.01; *, P<0.001 (ANOVA).
Figure 27B:
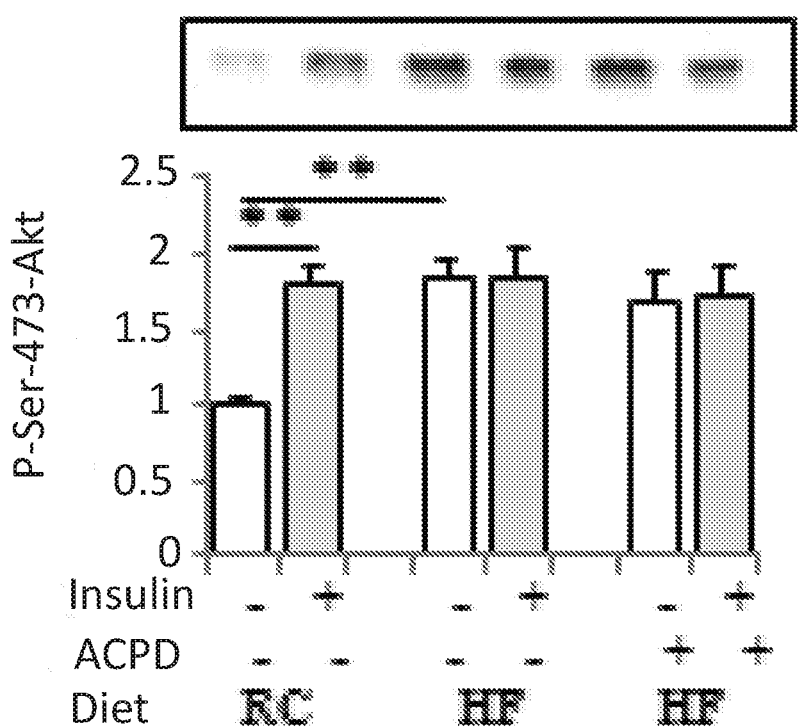
Figure 27C:
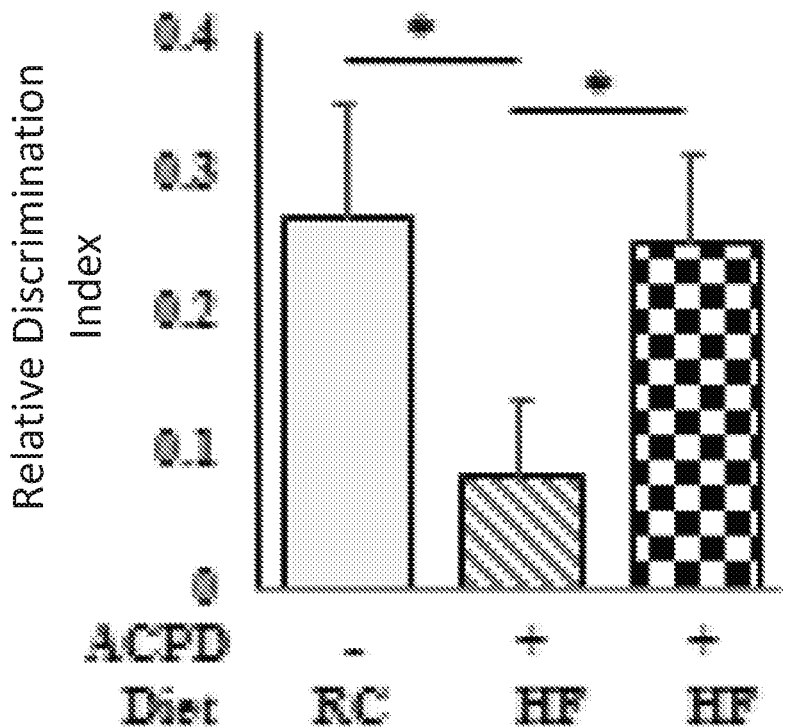
Figure 27D:
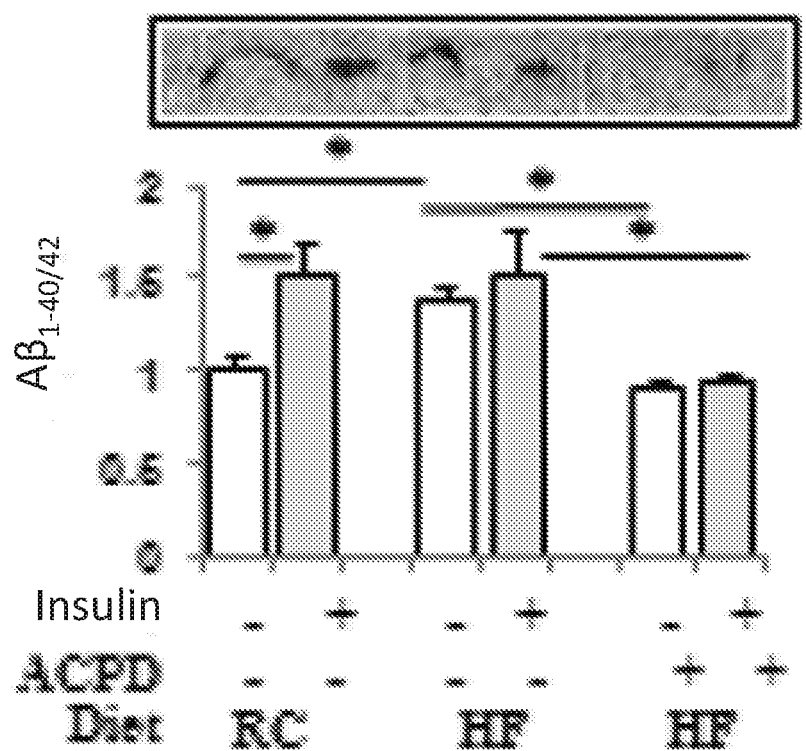
Figure 27E:
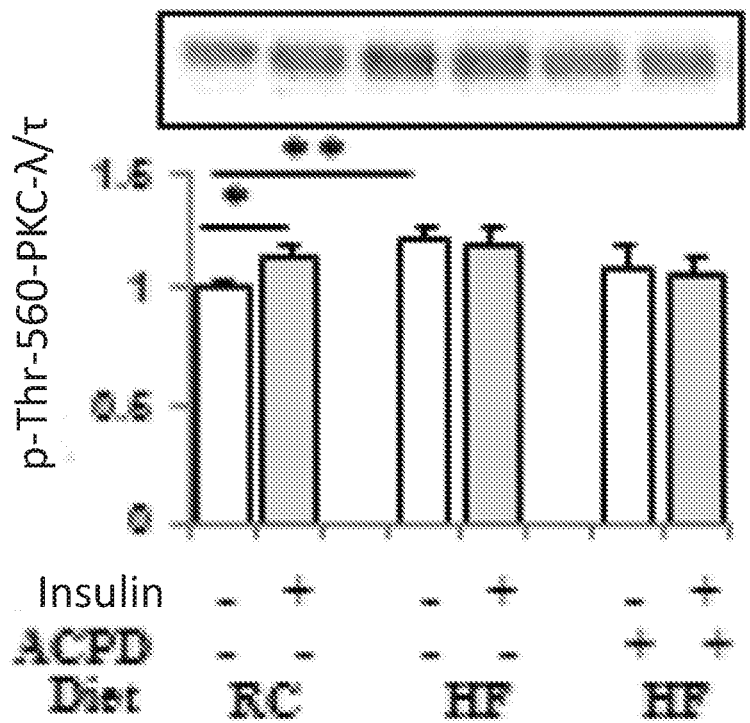
Figure 27F:
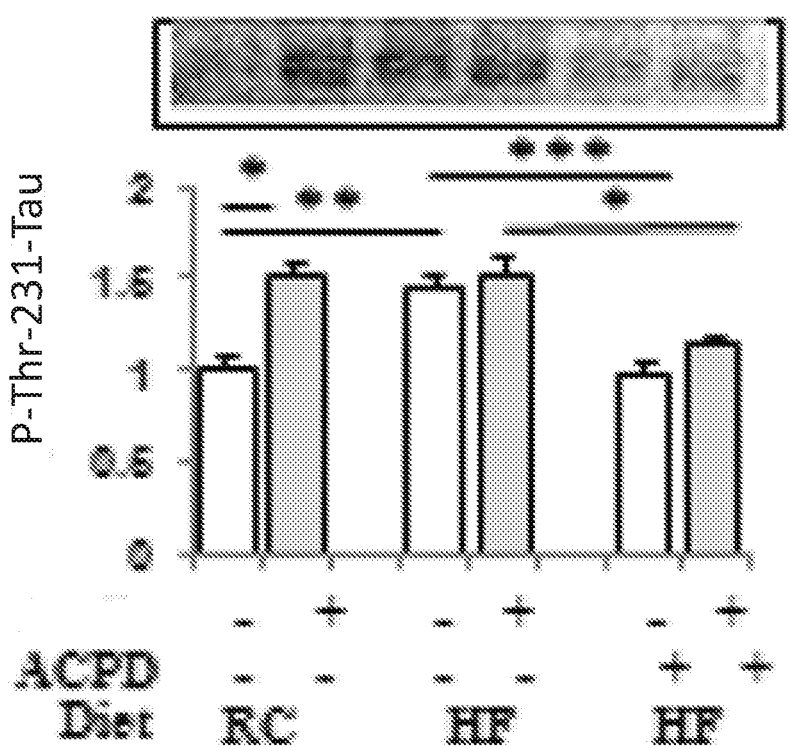

Effects of ACPD-mediated inhibition of Brain aPKC on High-Fat-Feeding-Induced (a) Elevations of Brain $A\beta_{1-40/42}$ and Phospho-thr-231-Tau, and (b) Impairment of Novel Object Recognition Memory Function. Results are demonstrated in FIGS. 27A-27F. Different from ATM- and ICAPP-treated Het-MλKO mice in which hyperinsulinemia was fully/sufficiently improved [8], the hyperinsulinemia in the more insulin-resistant HFF and ob/ob mice treated with 10 mg/kg body weight/day was only modestly, but not sufficiently, improved [6,7] to reverse resting/basal increases in brain 70 kDa PKC-λ/ι and Akt activities [9]. However, we presently found that a higher dose of 20 mg/kg ACPD (administered every other day as inhibition of hepatic aPKC activity persists near-maximally for 48 hours after subcutaneous ACPD injection [6,7]) reduced hyperinsulinemia-induced increases in resting/basal PKC-λ/ι activity to normal, and moreover, blocked acute stimulatory effects of insulin on 70 kDa PKC-λ/ι activity in these HFF mice (FIG. 27A). In contrast, HF diet-induced increases in resting/basal activities of brain 50 kDa PKM-ζ and Akt were not influenced appreciably by ACPD treatment (FIG. 27B). On the other hand, most interestingly, along with ACPD-induced decreases in 70 kDa PKC-λ/ι activity and decreased levels of $A\beta_{1-40/42}$ and thr-231-phospho-tau, the HFF-induced impairment in novel object recognition was obviated (FIG. 27C).

Figure 29A:
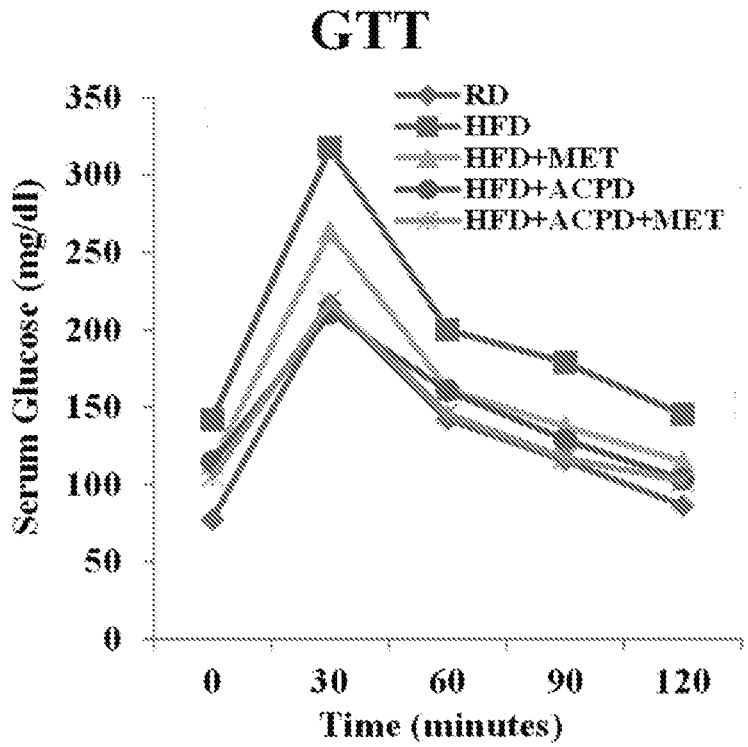
FIGS. 29A-29B show graphs that can demonstrate the effects of metformin (50 mg/kg/day; administered IP), ACPD (10 mg/kg/day; administered SC) and metformin+ACPD treatment on IP glucose tolerane test (GTT, FIG. 29A) and IP pyruvate tolerance test (PTT, FIG. 29B) in HFF mice.
Figure 29B:
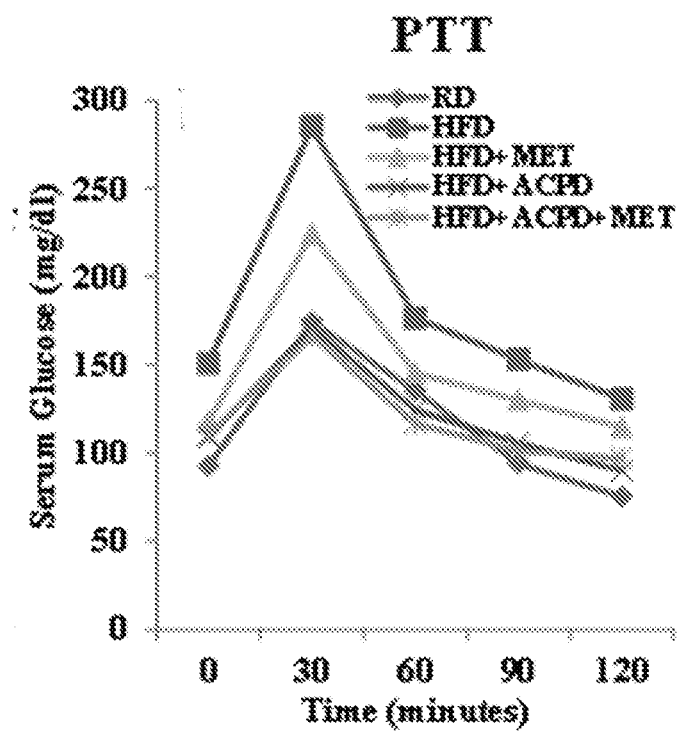

Additionally, the effects of metformin, ACPD, and metformin and ACPD on IP glucose tolerance and IP pyruvate tolerance was examined. Mice were fed a standard mouse chow or high fat (60%-kcal) for 8 weeks prior to testing. The results are demonstrated in FIGS. 29A-29B. Values are means of 8-10 mice.

Discussion

Figure 28:
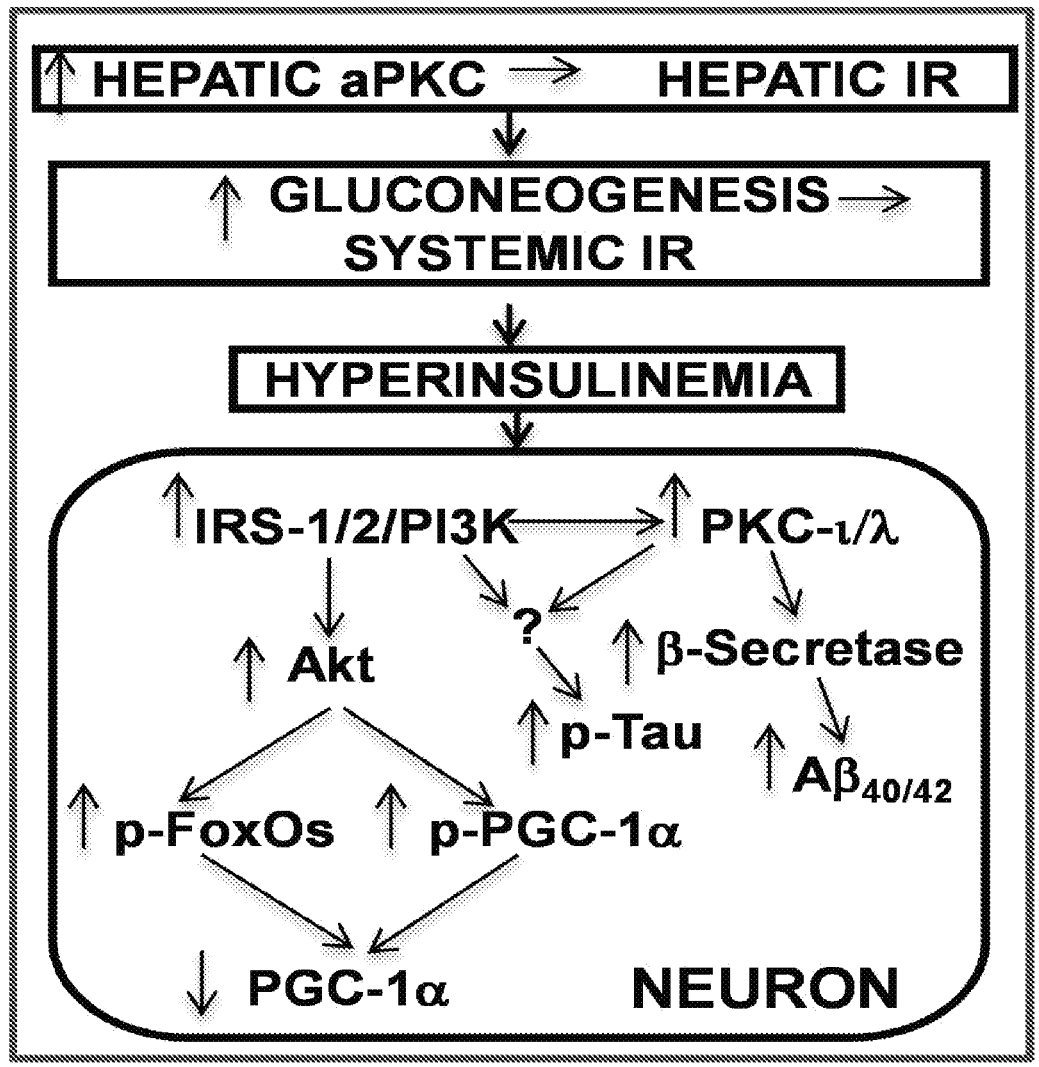
FIG. 28 shows a schematic that can demonstrate the pathogenesis of neuronal signaling abnormalities in insulin-resistant states that lead to production of factors that may abet development of Alzheimer's disease. In this scheme, diet-induced increases in hepatic aPKC activity lead to impaired Akt action and/or activation by insulin, e.g., hepatic insulin resistance (IR), increases in hepatic gluconeogenesis, systemic IR, and hyperinsulinemia, which persistently hyperactivates brain Akt and aPKC. Increases in brain Akt activity lead to phosphorylation and thus diminished activities of all FoxOs (1,3a,4,6), and decreased activity and expression of PGC-1α. Increases in brain aPKC activity, either directly or indirectly, provokes increases in β-secretase activity, and levels of $A\beta_{1-40/42}$ and phospho-thr-231-tau.

This observations presented in this Example can at least demonstrate that (a) insulin provoked rapid increases in β-secretase activity in mouse brain; (b) hyperinsulinemia in insulin-resistant HFF, ob/ob mice, Het-MλKO mice, and obese/T2D monkeys was accompanied by increases in brain β-secretase activity, as well as previously reported increases in PKC-λ/ι activity and $A\beta_{1-40/42}$ production [9]; (c) correction of hyperinsulinemia in insulin-resistant Het-MλKO mice by ICAPP, which improves systemic insulin resistance sufficiently by inhibiting hepatic aPKC in this model [8], simultaneously reduced the resting/basal hyperactivity of both Akt and aPKC to normal, and, moreover, restored insulin effects on Akt activation, but, in contrast, blocked acute stimulatory effects of insulin on PKC-λ/ι activity, β-secretase activity, and $A\beta_{1-40/42}$ production in brains of Het-MλKO mice; (d) PKC-A/1 was required for acute stimulatory effects of insulin on β-secretase activity and Aβ$_{1-40/42}$ production in brains of normal mice; and (e) in cultured neuronal cells, aPKC activators, insulin, metformin and expression of CA-PKC-λ/ι increased PKC-λ/ι activity, β-secretase activity, Aβ$_{1-40/42}$ production, and phospho-thr-231-tau levels, and aPKC inhibitor, ICAPP, and/or expression of KI-PKC-λ/ι blocked effects of insulin, metformin and constitutive PKC-λ/ι on these parameters. Perhaps most interestingly, the present findings showed that two PKC-λ/ι inhibitors, ICAPP and ACPD, were able to pass the blood brain barrier (BBB) in intact mice and inhibit hyperinsulinemia- and acute insulin-dependent increases in brain PKC-λ/ι activity, and simultaneously inhibit insulin-dependent increases, not only in β-secretase activity, Aβ$_{1-40/42}$ production, and thr-231-tau phosphorylation, but also prevented/repaired a HD diet-induced impairment in memory function, as evaluated by acute visual novel object recognition. Together, these findings suggested that aPKC activation may play an important role in the development of AD pathology (see FIG. 28) and cognitive dysfunction in hyperinsulinemic conditions.

The finding that PKC-λ/ι can cause acute stimulatory effects of insulin on β-secretase activity and Aβ$_{1-40/42}$ production in brains of intact mice and isolated neuronal cells further suggested that alterations in β-secretase were largely responsible for the increases in brain levels of Aβ$_{1-40/42}$ seen both in normal mice after acute insulin treatment, and in response to persistent hyperinsulinemia in insulin-resistant mice and monkeys. That insulin increased β-secretase activity, Aβ$_{1-40/42}$ production and thr-231-tau phosphorylation in mouse brain, and can therefore abet development of AD pathology, is seemingly at odds with the fact that intra-nasal insulin treatment is currently being used in clinical trials for patients with AD or mild cognitive impairment (MCI) [3,5]. The rationale for using insulin therapy in AD and MCI derives from findings indicating that levels of the insulin receptor and post-receptor insulin signaling factors are deficient in damaged brain areas of AD patients [2-5,17]. Indeed, AD has been called "type 3 diabetes", and it has led to postulation that insulin action in brain is impaired in insulin-resistant states, and the assumption that brain resistance per se predisposes to AD development However, contrariwise, at least the present Example suggests that prior to the development of significant AD pathology that can eventually lead to actual resistance to insulin, the brains of insulin-resistant obese and T2D subjects, presumably including those destined to develop AD, are, if anything, hyperinsulinized, and this, over time, can promote development of AD pathology by multiple mechanisms discussed above and elsewhere [9].

The data from isolated neuoronal cells indicates that increases in phospho-thr-231-tau levels seen previously [9] in brains of hyperinsulinemic ob/ob mice and obese/T2D monkeys, and seen presently in HFF mice consuming a diet supplying 60% of calories from fat, may also be due, in part, to increases in aPKC activity, and may contribute to the development of the intraneuronal neurofibrillary "tangles" in AD. However, it was also observed that increases in phospho-thr-231-tau were not seen in either HFF mice consuming a diet supplying 40% of calories from fat, or in Het-MλKO mice [9], and this can be reflective of lesser degrees of insulin resistance in Het-MλKO mice, or involvement of factors other than insulin.

In addition to the hyperactivation of brain PKC-λ/ι and subsequent increases in β-secretase activity and Aβ$_{1-40/42}$ levels, hyperactivation of brain Akt also occurs in insulin-resistant hyperinsulinemic states, and this leads to persistent Akt-dependent phosphorylation and thus inhibition, of the all four brain FoxOs3, 1/3a/4/6, and subsequent decreases in activity and levels of PGC-1 a [9]. These alterations can be important, as FoxOs and PGC-1α are needed to maintain brain memory functions and neuronal integrity (reviewed in [9]).

The fact that the aPKC inhibitors, ICAPP and ACPD, can cross the BBB and directly inhibit insulin-stimulated PKC-λ/ι in brain, and thereby diminish insulin-dependent increases in β-secretase activity, Aβ$_{1-40/42}$ levels and phospho-thr-231-tau levels, may have relevance, not only for hyperinsulinemia-dependent increases in brain aPKC activity, but also for increases provoked by other aPKC activators. In this regard, a variety of non-insulin PKC-λ/ι activators have been implicated in AD development, e.g., lipids that involve increases in sphingomyelins, ceramide and phosphatidic acid, hypoxia, hyperglycemia, proinflammatory cytokines, e.g., tumor necrosis factor-α and various agonists, e.g., insulin-like growth factor-1 and metformin, which reportedly increases 3-secretase and/or Aβ$_{1-40/42}$ levels [18-20]. This "promiscuity" of aPKC can indicate that direct and/or indirect inhibition of CNS PKC-λ/ι can be useful for preventing/diminishing β-amyloid plaque and phospho-tau accumulation in AD and pre-AD states.

Finally, in considering the use of aPKC inhibitors that act directly in brain, note that the truncated, 50 kDa PKMζ which is abundant and present only in brain, is thought to play a key role in long-term potentiation (LTP) and spatial long-term memory formation [21]. Further note: (a) HF feeding, presumably via hyperinsulinemia, modestly increased 50 kDa PKMζ activity, and ACPD treatment had no appreciable effect on. 50 kDa PKMζ activity (b) although brain-specific PKMζ knockout does not impair LTP and memory functions [22,23], it was recently found that hippocampal PKC-λ/ι can increase in amount and compensate for losses of hippocampal PKMζ in PKMζ knockout mice, and thereby maintain LTP and spatial memory functions [24, 25]; and (c) 70 kDa PKC-λ/ι is thought to play a role in short-term and LTP [25,27] memory functions. On the other hand, presently-used ACPD inhibited acute insulin- and hyperinsulinemia-related increases in activity of 70 kDa PKC-λ/ι and this was accompanied by substantial improvement in a defect in acute memory function, i.e., novel object recognition, induced by the HF diet.

REFERENCES FOR EXAMPLE 1

1. Janson J, Laedtke T, Parisi J E, O'Brien P, Peterson R C, Butler P C. Increased risk of type 2 diabetes in Alzheimer's disease. Diabetes 53: 478-481, 2004
2. De la Monte, S. M. Brain insulin resistance and deficiency as therapeutic targets in Alzheimer's disease. Curr Alzheimer Res 9: 35-66, 2012
3. Craft S. Insulin resistance and Alzheimer's disease pathogenesis: mechanisms and implications for treatment. Curr Alzheimer Res 4: 147-152, 2007
4. De Felice F G. Alzheimer's disease and insulin resistance: translating basic science into clinical applications. J Clin Invest 123: 531-539, 2013
5. Craft, S. Intranasal insulin therapy for Alzheimer's disease and amnestic mild cognitive impairment: a pilot clinical trial. Arch Neurol 69: 29-38, 2012
6. Sajan M P, Acevedo-Duncan M E, Standaert M L, Ivey R A, III, Lee M C, Farese R V. Akt-dependent phosphorylation of hepatic FoxO1 is compartmentalized on a WD40/Propeller/FYVE scaffold and is selectively inhibited atypical PKC in early phases of diet-induced obesity.

A mechanism for impairing gluconeogenic but not lipogenic enzyme expression. Diabetes 63: 2690-2701, 2014
7. Sajan M P, Ivey R A, III, Lee M C, Farese R V. Hepatic insulin resistance in ob/ob mice involves increases in ceramide, atypical PKC activity and selective impairment of Akt-dependent FoxO1 phosphorylation. J Lipid Res 56:70-80, 2015
8. Sajan M P, Nimal S, Mastorides S, Acevedo-Duncan M, Kahn C R, Fields A P, Braun U, Leitges M, and Farese R V. Correction of Metabolic Abnormalities in a Rodent Model of Obesity, Metabolic Syndrome and Type 2 Diabetes by Inhibitors of Hepatic Protein Kinase C-iota. Metabolism 61: 459-469, 2012
9. Sajan, M. P. Ivey R A, III, Farese R V. Brain insulin signaling is increased in insulin-resistant states and decreases in FOXOs and PGC-1a and increases in Aj31-40/42 and phospho-tau may abet Alzheimer's development. Diabetes 65:1892-1903, 2016
10. Salih D A M, Rashid A J, Colas D, de la Torre-Libieta L, Zhu R P, Morgan A A, Santo E E, Ucar D, Devarajan K, Cole C J, Madison D V, Shamloo M, Butte A J, Bonni A, Josselyn S A, Brunet A. FoxO6 regulates memory consolidation and synaptic function. Genes and Development 26: 2780-2801, 2012
11. Renault V M, Rafalski V A, Morgan A, Salih D A, Brett J O, Webb A E, Villeda S, Thekkat P U, Guillerey C, Denko N C, Palmer T D, Butte A J, Brunet A. FoxO3 regulates neural stem cell homeostasis. Cell Stem Cell 5: 527-539, 2009
12. Gong B, Pan Y, Pasinetti G M. Nicotinamide riboside restores cognition through an upregulation of proliferator-activated receptor-coactivator 1 regulated-secretase 1 degradation and mitochondrial gene expression in Alzheimer's mouse models. Neurobiol Aging 34: 1581-1588, 2013
13. Paik J-H, Ding Z, Narukar R, Ramkissoon S, Muller F, Kamoun W S, Ghae S-S, Zheng H, Ying H, Mahoney J, hiller D, Jiang S, Protopopov A, Wong W H, Chin L, Logon K L, DePinho R A. FoxOs cooperatively regulate diverse pathways governing neural stem cell homeostasis. Cell Stem Cell 5: 540-553, 2009
14. Qin, W. Haroutunian V, Katsel P, Cardozo C P, Lo H, Buxbaum J D, Pasinetti G M. PGC-1a expression decreases in the Alzheimer disease brain as a function of dementia. Arch Neurol 66: 352-361, 2009.
15. G. Sweeney G, Song J. The association between PGC-1 a and Alzheimer's disease. Anat Cell Biol 49: 1-6, 2016.
16. Sajan, M. P, Farese, R. V. Insulin Signalling in Hepatocytes of Type 2 Diabetic Humans. Excessive Expression and Activity of PKC-ι and Dependent Processes and Reversal by PKC-ι Inhibitors. Diabetologia. 55: 1446-1457, 2012
17. Chen Y, Zhou K, Wang R, Liu Y, Kwak Y-D, Ma T, Thompson R C, Zhao Y, Smith L, Gasparini L, Luo Z, Xu H, Liao F-F. Antidiabetic drug metformin (Glucophage) increases biogenesis of Alzheimer's amyloid peptides via upregulating BACE1 transcription. Proc Natl Acad Sci USA 106: 3907-3912, 2009
18. Frolich P, Blum-Degen D, Bernstein H G, Engelsberger S, Humrich J, Laufer S, Muschner D, Thalheimer A, Turk A, Hoyer S, Zochling R, Boissl K W, Jellinger K, Riederer P. Brain insulin and insulin receptors in aging and sporadic Alzheimer's disease. J Neural Transm 105: 423-438, 1998
19. J. Zemva, M. Schubert, The role of neuronal insulin/insulin-like growth factor-1 signaling for the pathogenesis of Alzheimer's disease: possible therapeutic implications. CNS Neurol. Disord. Drug Targets 13: 322-337, 2014
20. Gontier G, George C, Chaker Z, Holzenberger M, Aid S. Blocking IGF signaling in adult neurons activates Alzheimer's disease pathology through amyloid-clearance. J Neurosci 35: 11500-11513, 2015
21. Sacktor T C. PKMzeta, LTP maintenance, and the dynamic molecular biology of memory storage. Prog Brain Res 169: 27-40, 2008
22. Lee, A. M. Kanter B R, Wang D, Lim J P, Zou M E, Qiu C, McMahon T, Dagdar J, Fischbach-Weiss S C, Messing R O. Prkc null mice show normal learning and memory. Nature 493: 416-420, 2013
23. Volk, L. J., Bachman, J. L., Johnson, R., Yu, Y., Huganir, R. L. PKM-ζ is not required for hippocampal synaptic plasticity, learning and memory. Nature 493: 420-425, 2013
24. Tsokas, P. Hsieh C, Yao Y, Lesburgueres E, Wallace E J C, Tcherepanov A, Jothaniandan D, Hartley B R, Pan L, Rivard B, Farese R V, Sajan M P, Bergold P J, Hernandez A I, Cottrell J, Harel Z, Shouval H Z, Fenton A A, Sacktor T C. Compensation for PKM (in LTP and spatial long-term memory in mutant mice. eLife 2016:5:e14846.
25. Ren S-Q, Yan J-Z, Zhang X Y, Bu Y-F, Pan W-W, Yao W, Tian T, Lu W. PKCλ is critical in AMPA receptor phosphorylation and synaptic incorporation in LTP. The EMBO J 32: 1365-1380, 2013
26. Pillai P, Desai S, Patel R, Sajan M, Farese R, Ostrov D, Acevedo-Duncan M. A novel PKC-ι inhibitor abrogates cell proliferation and induces apoptosis in neuroblastoma. Int J Biochem Cell Biol 43:784-794, 2011.
27. Wang S, Sheng T, Ren S, Tian T, Lu W. Distinct roles of PKCλ/ι and PKMζ in the initiation and maintenance of hippocampal long-term potentiation and memory. Cell Reports 16: 1954-1961, 2016.
28. Wang J, Gallagher D, DeVito L M, Cancina G I, Tsui D, He L, Keller G M, Frankland P W, Kaplan D R, Miller F D. Metformin activates an atypical PKC-CBP pathway to promote neurogenesis and enhance spatial memory formation. Cell Stem Cell 11: 23-35, 2012.
29. Antunes M, Biala G. The novel object recognition memory: neurobiology, test procedure and its modification. Cogn Process 13: 93-110, 2012.

Example 2

Introduction

Insulin-resistant obesity and the metabolic syndrome are present in one of three adults (1) and progress to type 2 diabetes mellitus (T2DM) in one of four people over 65 years of age. Alzheimer disease (AD) afflicts one of eight people over 65 years of age and one of two people over 85 years of age. Moreover, AD risk in people with T2DM and vice versa is increased twofold (2,3), and fasting glucose intolerance or T2DM was present in four of five Mayo Clinic AD patients (4). It is therefore suspected that insulin-resistant states may predispose the brain to development of late-onset AD.

Mechanisms that might link insulin-resistant states with AD are obscure. Obesity/T2DM-associated vascular disease may contribute, but alterations in insulin signaling factors in AD brains raise the suspicion of a relationship. In particular, human AD brains show diminished insulin receptor levels and impairments in insulin receptor substrate (IRS)-1 (5,6), which, in some tissues, activates both protein kinase B (mammalian homolog to viral-Akt [Akt]) and atypical protein kinase C (aPKC), the two intracellular mediators of most insulin effects. However, in liver, although IRS-1 activates Akt, IRS-2 activates aPKC (7), and information on IRS-1 and IRS-2 in brain is lacking. Nevertheless, as systemic insulin resistance is often considered to be generalized, it is postulated that the brain is similarly insulin resistant and abets AD development (8-11). To reinforce this idea, it is theorized that insulin-stimulated Akt phosphorylates/inhibits glycogen synthase kinase-3β (GSK3(3), which, by phosphorylating threonine (Thr)-231-tau (12,13), increases intraneuronal phospho (p)-tau tangles, which, along with interneuronal β-amyloid ($A\beta_{1-40/42}$) peptide-containing plaques, promotes AD pathology (14). With this rationale, intranasal insulin therapy is now in clinical trials for the treatment of putative brain insulin resistance in AD (15).

However, insulin resistance is not necessarily generalized. Indeed, insulin-sensitive pathways extrinsic to that responsible for impaired glucose metabolism may be intact and hyperactivated. For example, in the initial phases of insulin resistance in high-fat-fed (HFF) (16) and ob/ob (17) mice, the level of hepatic aPKC is inordinately increased by diet-derived ceramide; aPKC selectively impairs insulin/Akt regulation of hepatic FOXO1; and subsequent increases in peroxisome proliferator-activated receptor γ coactivator-1α (PGC-1α) provoke increases in gluconeogenesis, glucose intolerance, systemic insulin resistance, and hyperinsulinemia, which increases still-intact hepatic Akt activity and lipogenesis (16,17). Additionally, in livers of obese humans and humans with T2DM, insulin activation of IRS-2 is conserved and further activates aPKC and lipogenesis, even when IRS-1 and Akt are downregulated (18,19).

To explore the relationships between systemic insulin resistance and neurodegenerative disorders, in this Example at least insulin signaling in brains of mice with diet-induced obesity (D10), HFF mice, and hyperphagic ob/ob mice consuming high-carbohydrate chow (16,17); mice in which insulin resistance is provoked by impaired muscle glucose transport owing to heterozygous muscle-specific PKC-A knockout (Het-MλKO) (20,21); and monkeys with long-standing diet-dependent obesity and T2DM was examined. In these models, brain insulin-signaling factors were at least observed to be maximally activated, thus leading to 1) hyperphosphorylation/inactivation of FOXO proteins and subsequent decreases in PGC-1a that together maintain neuronal function/integrity and 2) insulin-dependent increases in $A\beta_{1-40/42}$ peptides and p-tau that may promote AD plaque and tangle formation.

Materials and Methods

Mouse Studies. Brains were harvested from mice used in previous studies of insulin signaling and resistance in liver and muscle: 1) 4- to 6-month-old male C57BL/6 ob/ob and lean ob+ mice (The Jackson Laboratory, Bar Harbor, ME) (17), 2) 4- to 6-month-old male and female C57BL/6 mice used in studies of high-fat feeding (colony in University of South Florida [USF] vivarium) (16), and 3) 10- to 12-month-old C57BL/6 male and female Het-MλKO mice and littermate wild-type mice (colony in USF vivarium) (20,21). Males and females were comparably present in experimental groups 2 and 3, as sex did not alter the combined findings; hepatic alterations and clinical characteristics were reported previously (16,17,20,21). Mice were housed in environmentally controlled rooms and randomly fed standard mouse chow supplying 10% of calories from fat or diets supplying either 40% or 60% of calories from fat (Harlan Laboratories, Madison, WI) (16). Note that insulin-signaling results in brains (and liver and muscle) of mice fed 40% kcal fat and 60% kcal fat diets were comparable and therefore combined.

Where indicated, Het-MλKO mice were randomly injected subcutaneously daily for 8 days with aurothiomalate (ATM) (60 mg/kg body wt [bw]) or [1H-imidazole-4-carboxamide,5-amino]-[2,3-dihydroxy-4-[(phosphono-oxy)methyl]cyclopentane-[1R-(1a,2b,3b,4a)] (ICAPP) (0.4 mg/kg/bw) in saline to selectively inhibit hepatic aPKC and reduce serum insulin levels (21). Where indicated, mice were randomly treated with insulin (1 unit/kg/bw i.p.) 15 min before being euthanized by administration of xylazine/ketamine, followed by whole-body perfusion with PBS and rapid removal of brain and other tissues.

To summarize, the following schedules were used: HFF mice, age 4-6 months, normal or HFF diet×10 weeks, intraperitoneal insulin administration 15 min before killing; ob/ob mice, age 4-6 months, normal diet, intraperitoneal insulin administration 15 min before killing; and Het-MλKO mice, age 10-12 months, normal diet, once-daily subcutaneous ATM administration for 8 days before killing, intraperitoneal insulin administration 15 min before killing.

All experimental procedures involving mice were approved by the institutional animal care and use committees of the USF Morsani College of Medicine or the Roskamp Institute, and the James A. Haley Veterans Hospital Research and Development Committee.

Monkey Studies. Brains were obtained immediately post-mortem from 16- to 30-year-old male and female lean nondiabetic and obese/T2DM *Macaca mulatta* rhesus monkeys. Diabetic monkeys had been maintained on ad libitum standard monkey chow and treated with standard daily insulin regimens similar to those of patients with advanced T2DM, as described previously (22,23). Euthanitization was initiated with ketamine-HCl (10-15 mg/kg/bw) followed by intravenous Euthasol (0.22 mL/kg/bw). Brain samples were frozen in liquid N2 and stored at −160°. Experimental procedures involving monkeys, including euthanitization, were approved by the USF Morsani College of Medicine Institutional Animal Care and Use Committee.

Tissue Preparations. Mouse brains were hemisected sagittally, and one half was frozen in liquid N2, stored at −80° C., and subsequently homogenized in buffer containing 0.25 mol/L sucrose, 20 mmol/L Tris/HCl (pH 7.5), 2 mmol/L EGTA, 2 mmol/L EDTA, 1 mmol/L phenylmethylsulfonyl fluoride, 20 μg/mL leupeptin, 10 μg/mL aprotinin, 2 mmol/L Na4P2O7, 2 mmol/L Na3VO4, 2 mmol/L NaF, and 1 μmol/L microcystin and then supplemented with 1% Triton X-100, 0.6% Nonidet, and 150 mmol/L NaCl. The remaining brain halves were fixed in 4% paraformaldehyde and embedded in paraffin, and 4-μm sagittal sections were prepared on a microtome for immunohistochemical staining.

Western Analyses. Western analyses were conducted with rabbit antisera or mouse monoclonal antibodies (16-21) using the following: anti-aPKC (Santa Cruz Biotechnology, Santa Cruz, CA); anti-p-Thr-560/555-PKC-ζ/λ/ι (Invitrogen, Carlsbad, CA); anti-p-serine (Ser)-256-FOXO1 and anti-FOXO1 (Abnova, Walnut, CA); anti-Akt (mouse monoclonal antibodies), anti-p-Ser-473-Akt, anti-p-Ser-9-GSK3p, anti-GSK3p, anti-p-Ser-253-FOXO3a, anti-FOXO3a, anti-p-Ser-256-FOXO1, anti-p-Ser-193-FOXO4, anti-FOXO1, anti-p-Ser-2448-mammalian target of rapamycin (mTOR), anti-mTOR, anti-41-40/42 (5-10 kDa), and anti-amyloid precursor protein (APP; 120 kDa) (Cell Signaling Technology, Danvers, MA); and anti-p-Ser-202-tau and anti-p-Thr-231-tau (GeneTex, Irvine, CA). Samples from experimental groups were compared on the same blots and routinely checked with loading controls. Note that 75-kDa aPKC is largely PKC-λ in mouse brain and 98% homologous PKC-ι in brains of monkeys, humans, and other primates; PKC-ζ in brain exists largely as a 50-kDa moiety that, lacking a regulatory domain, is constitutively active and unresponsive to insulin; 50-kDa PKC-ζ (also called PKM-ζ) is produced by the operation of an intronal promoter and downstream transcription start site and is postulated to function in long-term memory potentiation (24); however, this idea has been challenged (25,26).

Immunohistochemistry. The 4-μm brain sections were deparaffinized in an automated system (Discovery XT; Ventana Medical Systems) with EZ Prep solution. A heat-induced antigen retrieval method was used in Cell Conditioning 1 solution. Rabbit primary antibody reacting with pAkt (ab81283; Abcam, Cambridge, MA) was used at a 1:200 dilution in PSS Diluent for antibodies (Ventana Medical Systems) and was incubated for 32 min, followed by OmniMap anti-rabbit secondary antibody (Ventana Medical Systems) for 20 min. For detection, the Discovery Chromo-Map DAB Kit (Ventana Medical Systems) was used; slides were then counterstained with hematoxylin, dehydrated, and coverslipped. A BX53 Microscope (Olympus) and cellSens Dimension software were used to obtain pictures with ×10 and ×60 objectives.

Statistical Analyses. Data are expressed as the mean±SEM and were compared using one-way ANOVA and Tukey post hoc test for analysis of significance.

Results

Studies in HFF and ob/ob Mice. In control mice, short-term maximal insulin treatment provoked increases in brain activities (as per phosphorylation) of Akt and aPKC (FIGS. 11A-11F). However, resting/"basal" activities of Akt and aPKC were maximally or near maximally elevated, presumably by preexisting hyperinsulinemia (16,17), in brains of HFF and ob/ob mice because there was little or no response of either Akt or aPKC to exogenous insulin (FIGS. 11A-11F). With Akt activation, phosphorylation of multiple Akt substrates, namely, GSK3β, mTOR, FOXO1, FOXO3a, and FOXO4, was elevated in the resting/basal state in brains of HFF and ob/ob mice and, here again, maximally or near maximally because short-term insulin treatment had little or no additive effect (FIGS. 11A-11F) (the level of p-FOXO4 was similarly increased but not shown).

Immunohistochemical methods were also used to examine Akt activation in individual neurons in the anterior cortex and hippocampus. In this regard, it has previously been shown (27) that insulin-signaling responses are seen largely in neurons, rather than glial or endothelial cells, most notably in neurons of the hippocampus and hypothalamus. Similarly, Akt activity was largely confined to neurons, most prominently and significantly increased in hippocampal and anterocortical regions of HFF and ob/ob mice (FIGS. 14A-14K).

Figure 15A:
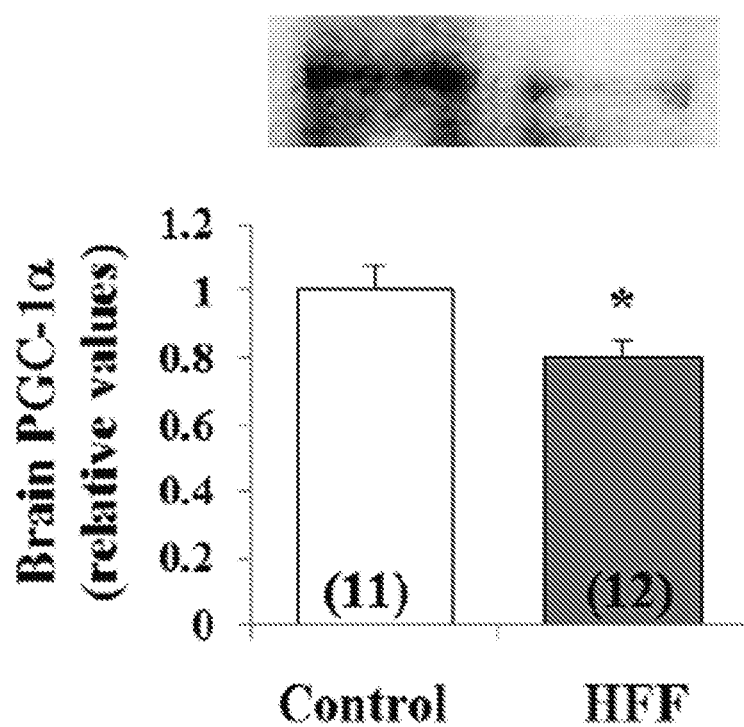
FIGS. 15A-15B show graphs and images of representative blots that can demonstrate Diminished levels of PGC-1a in brains of HFF (FIG. 15A) and ob/ob (FIG. 15B) mice. Portrayed values are mean±SEM of (N) mice. *$P<0.05$ for comparison of HFF or OB control mice (ANOVA).
Figure 15B:
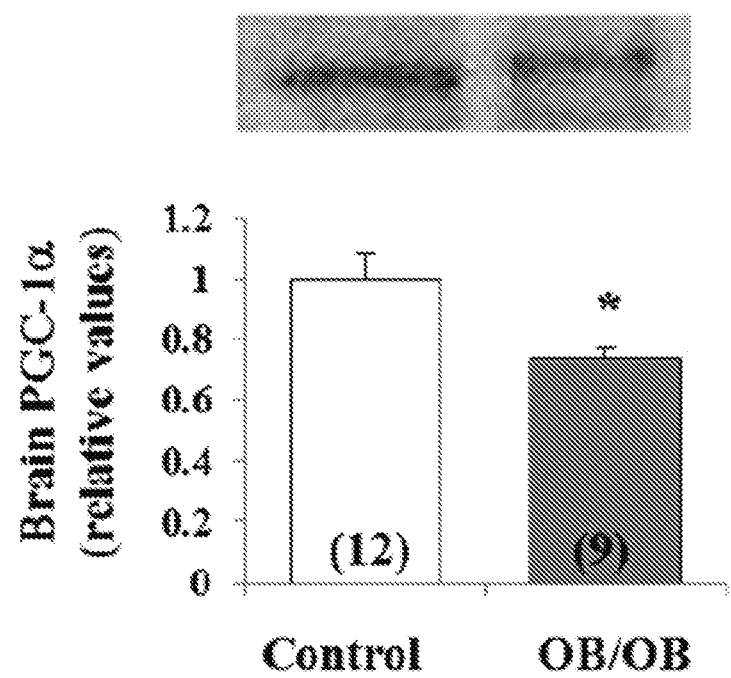
Figure 16A:
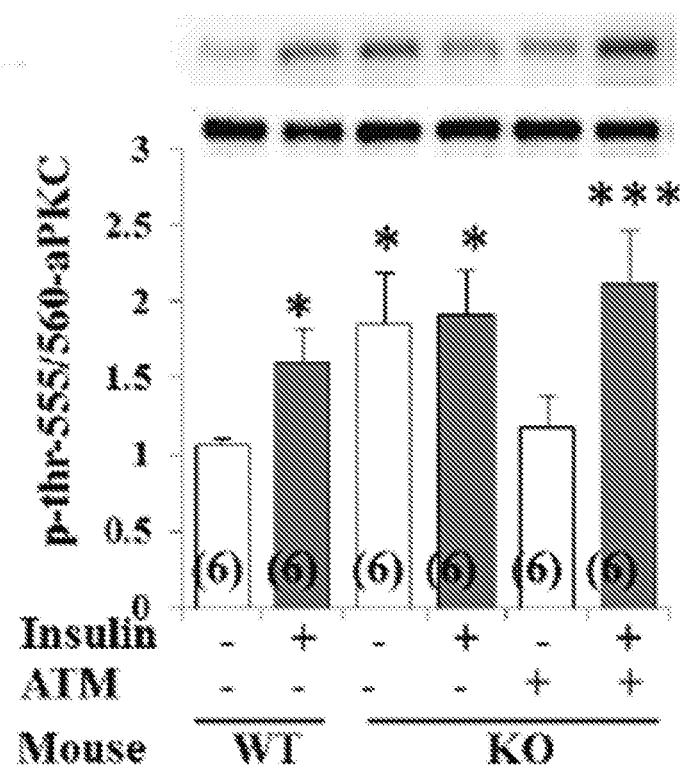
FIGS. 16A-16F show graphs and images of representative blots that can demonstrate effects of liver-selective aPKC inhibitor ATM on resting/basal and insulin-stimulated phosphorylation/activity of aPKC and Akt and phosphorylation of Akt substrates FOXO1, FOXO3a, GSK3β, and mTOR in brains of wild-type (WT) control and Het-MλKO (KO) mice. Where indicated, ad libitum-fed mice were treated with insulin (1 unit/kg bw i.p.) 15 min before being killed. Where indicated, Het-MλKO mice were injected once daily for 8 days with aPKC inhibitor ATM (60 mg/kg bw s.c.), which reversed hyperinsulinemia. Portrayed values of phosphoproteins are reported as the mean±SEM of 6 mice. *$P<0.05$, $P<0.01$, and *$P<$(ANOVA) for comparison of values of indicated groups vs. values of the WT control group.
Figure 16B:
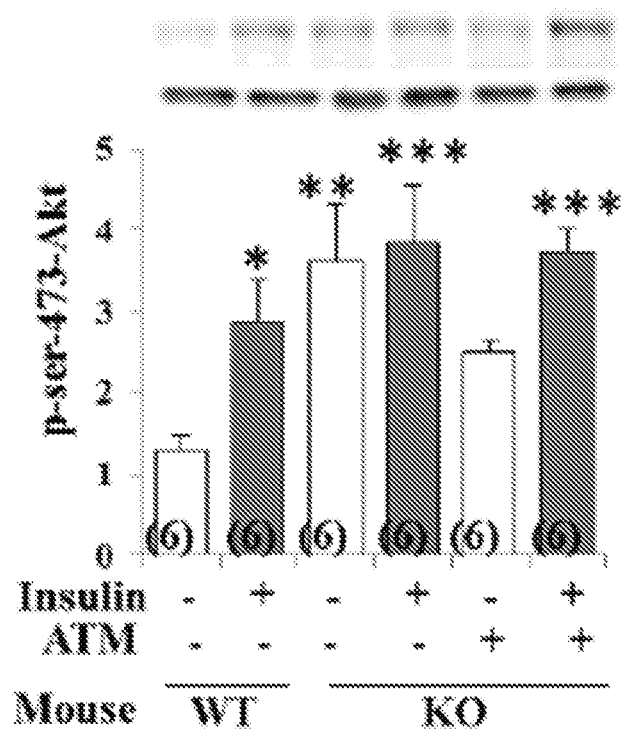
Figure 16C:
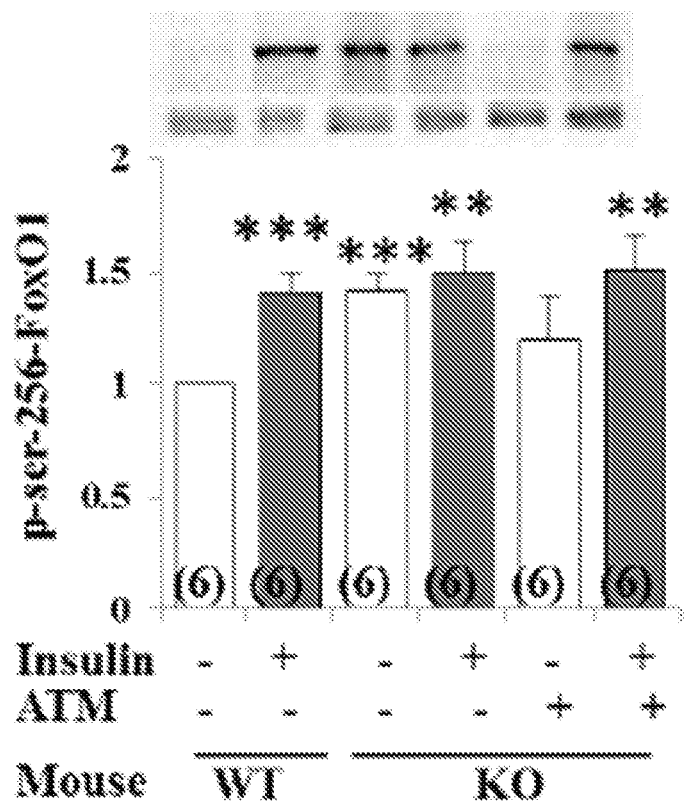
Figure 16D:
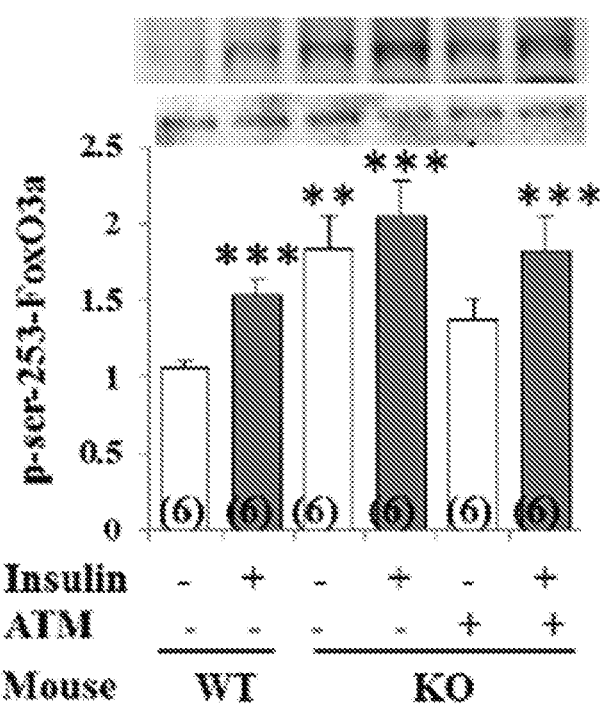
Figure 16E:
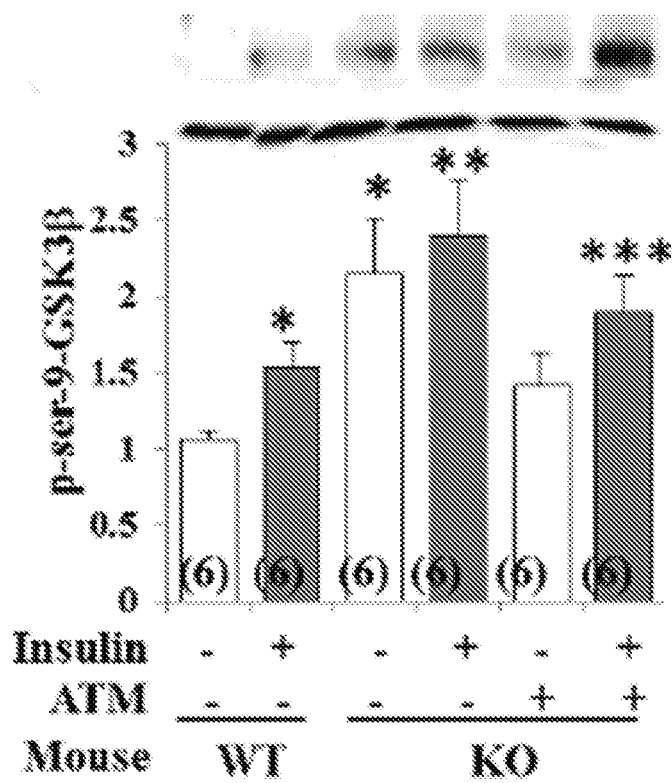
Figure 16F:
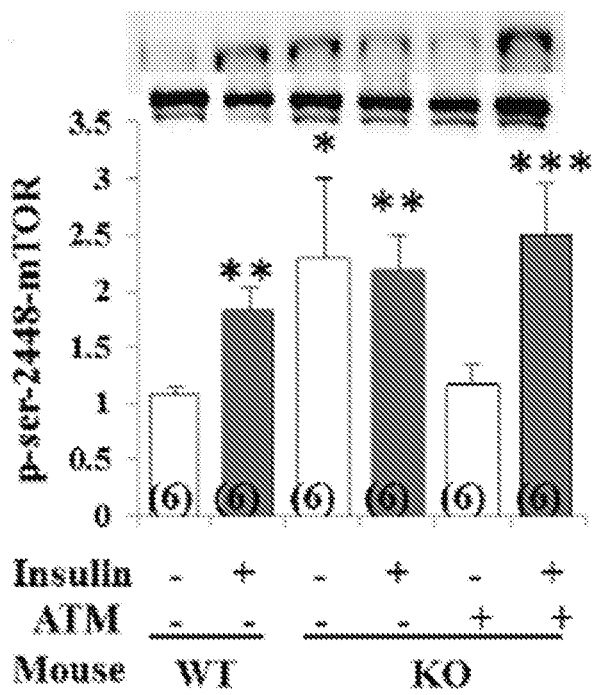

In keeping with the fact that FOXO1 controls PGC-1α expression and FOXO1 phosphorylation would diminished its activity, PGC-1α levels were diminished in HFF and ob/ob mice (FIGS. 15A-15B).

Studies in Het-MλKO Mice and Reversal of Brain-Signaling Aberrations by Correction of Insulin Resistance. In addition to DIO mice, in which insulin resistance starts in liver (15,16), we studied Het-MλKO mice, in which insulin resistance is initiated by impaired glucose transport in muscle; and resultant hyperinsulinemia hyperactivates hepatic aPKC, causing excessive activation of gluconeogenic and lipogenic pathways that contribute importantly to glucose intolerance, insulin resistance, abdominal obesity, hyperlipidemia, hepatosteatosis, and mild/moderate T2DM (20,21). As in HFF and ob/ob mice, resting/basal activities of Akt and aPKC and phosphorylation levels of FOXO1, FOXO3a, GSK3β, and mTOR were maximally or near maximally increased in brains of Het-MλKO mice because short-term insulin treatment increased phosphorylation of these factors in control wild-type mice but not in Het-MλKO mice (FIGS. 15A-15B).

As reported previously (21), tissue-selective inhibition of hepatic aPKC by ATM not only effectively diminished hepatic biochemical and clinical abnormalities but, moreover, reduced serum insulin levels to normal in Het-MλKO mice. It was therefore important to find that this marked improvement in hyperinsulinemia in ATM-treated Het-MλKO mice was attended by reductions in resting/basal activities of brain Akt and aPKC to levels comparable to those seen in wild-type mice; further, with diminished Akt activity, the phosphorylation of FOXO1, FOXO3a, GSK3β, and mTOR similarly diminished to near-normal levels (FIGS. 16A-16F). Moreover, with decreases in resting/basal Akt and aPKC activities and Akt substrate phosphorylations after treatment of Het-MλKO mice with ATM, short-term insulin treatment provoked essentially normal increases in these parameters (FIGS. 16A-16F), indicating a restoration of normal brain insulin-signaling mechanisms.

In addition to ATM, treatment of Het-MλKO mice with another liver-selective aPKC inhibitor, ICAPP, similarly reduced serum insulin levels in Het-MλKO mice to normal (21), and this normalization was attended by reductions of resting/basal activities of brain Akt and aPKC, comparable to those seen with ATM treatment (data not shown).

Figure 17A:
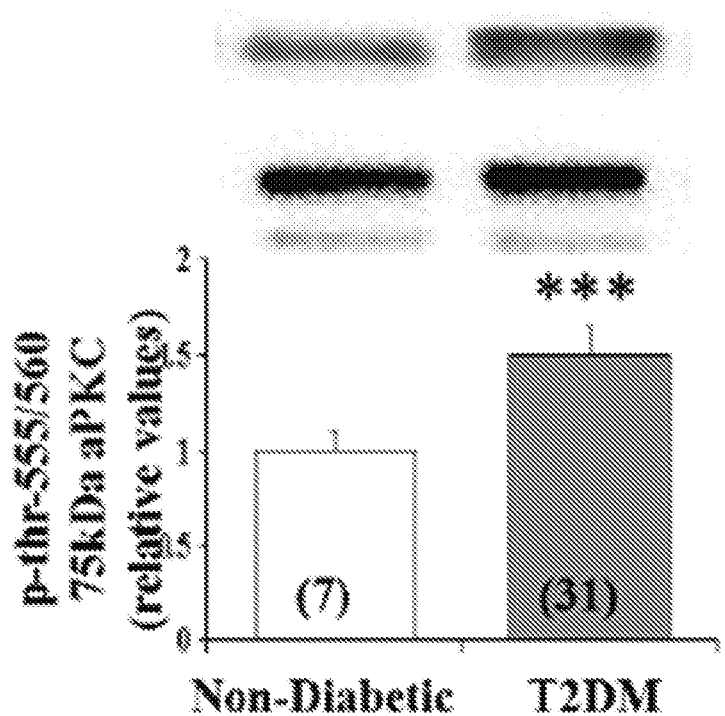
FIGS. 17A-17F show graphs and images of representative blots that can demonstrate resting/basal and insulin-stimulated phosphorylation/activity of the 75-kDa aPKC (largely PKC-ι) (FIG. 17A) and Akt (FIG. 17B) and phosphorylation of Akt substrates FOXO1 (FIG. 17C), FOXO3a (FIG. 17D), GSK3β (FIG. 17E), and mTOR (FIG. 17F) in brains of nondiabetic and T2DM monkeys. Portrayed values of phosphoprotein levels are the mean±SEM of (N) monkeys. *$P<0.05$ and ***$P<0.001$ for comparison of T2DM and nondiabetic monkeys (ANOVA).
Figure 17B:
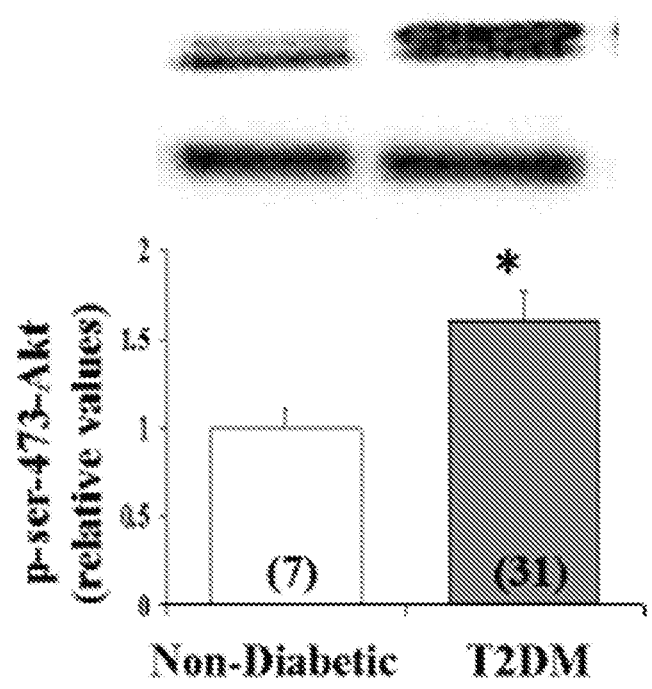
Figure 17C:
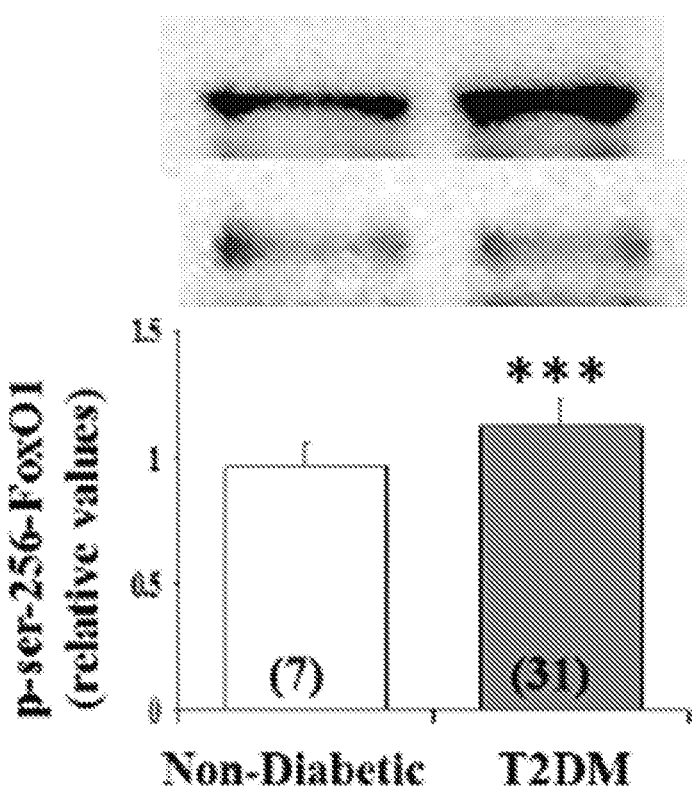
Figure 17D:
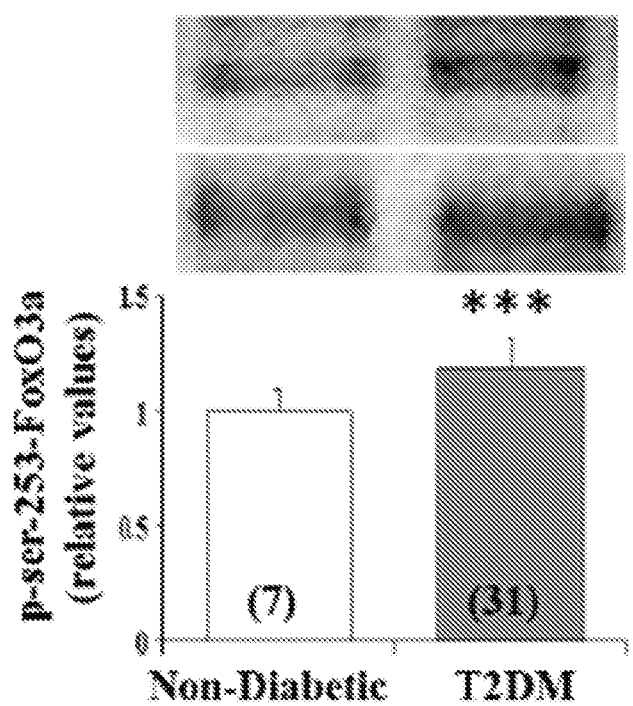
Figure 17E:
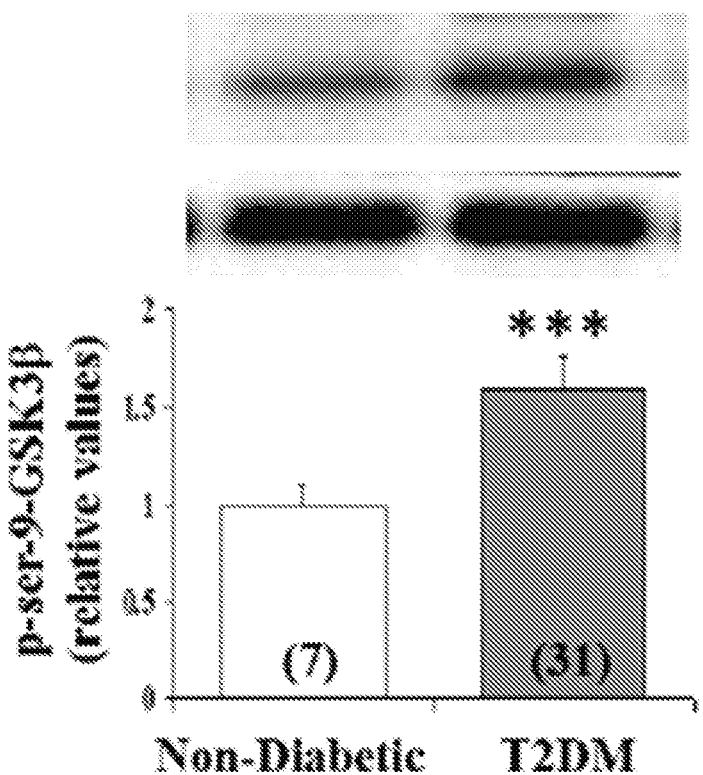
Figure 17F:
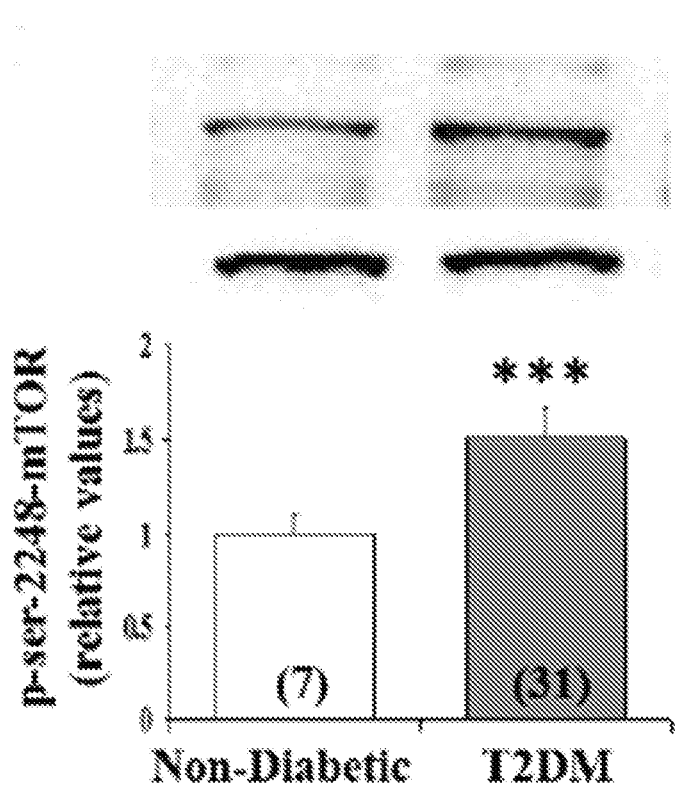

Studies in T2DM Monkeys. As mouse insulin resistance syndromes were relatively short-lived and mild, we studied monkeys with long-standing obesity and insulin-requiring T2DM (Table 1, clinical characteristics). As in mouse models, phosphorylation/activities of Akt and aPKC and phosphorylation of Akt substrates FOXO1, FOXO3a, GSK3β, and mTOR were increased in brains of T2DM monkeys (FIGS. 17A-17B).

TABLE 1

Clinical Characteristics of Normal and type 2 Diabetic Monkeys

| Characteristic | Non-diabetic (N = 7) | Type 2 Diabetic (N = 31) |
| --- | --- | --- |
| Age (yrs) | 26 ± 2.5 | 23 ± 0.8 |
| Body Weight (kg) | 8 ± 1.02 | 12 ± 0.8 * |
| % Body Fat | 24 ± 3.6 | 33 ± 1.9 * |
| Fasting Plasma Glucose (mg/dl) | 62 ± 2.7 | 221 ± 19 *** |
| Fasting TG (mg/dl) | 107 ± 25.3 | 466 ± 82 * |
| Fasting Plasma Cholesterol (mg/dl) | 142 ± 11.0 | 196 ± 19 |
| Fasting Plasma Insulin (pU/mL) | 34 ± 5.8 | 75 ± 11 * |
| HbA1C (%) | 3.75 ± 0.1 | 7.67 ± 0.9 * |

Values are Mean ± SEM.
Asterisks indicate:
* P < 0.05; and
*** P < 0.001 (ANOVA).
N = number of monkeys.

$A\beta_{1-40/42}$ Peptide and APP Levels in Mouse and Monkey Brain. Particularly important, the levels of $A\beta_{1-40/42}$ peptide, which may accumulate to form amyloid plaques, were increased in the short term by insulin in brains of control mice and in the resting/basal state in HFF, ob/ob, and Het-MλKO mice and obese/T2DM monkeys (FIGS. 18A-18D). Moreover, levels of 120-kDa APP, the $A\beta_{1-40/42}$ precursor, were diminished in obese/T2DM monkeys (FIG.

Figure 18A:
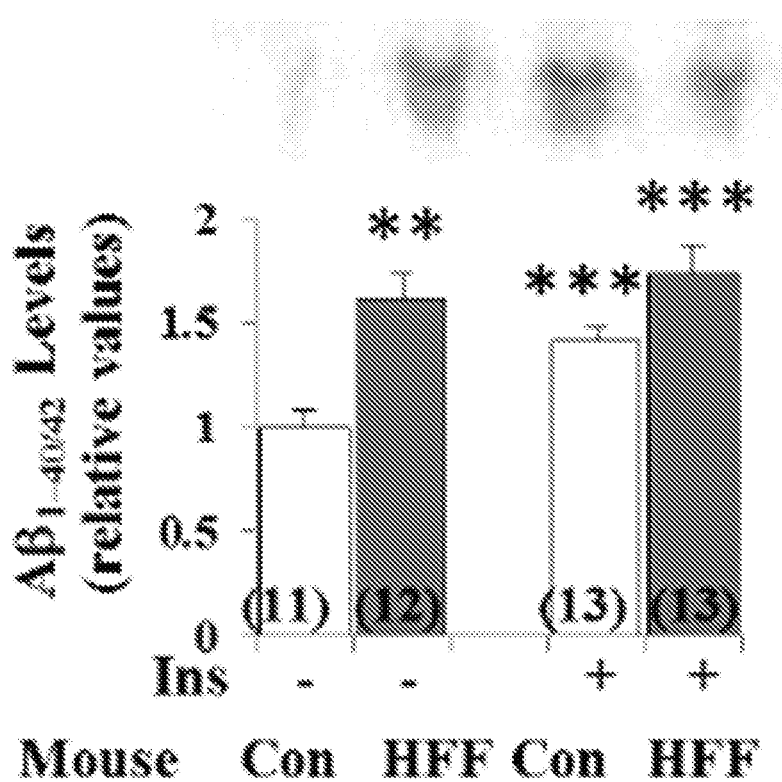
FIGS. 18A-18E show graphs and images of representative blots that can demonstrate levels of $A\beta_{1-40/42}$ peptides in brains of HFF mice (FIG. 18A), ob/ob mice (FIG. 18B), Het-MλKO (KO) mice (FIG. 18C), and T2DM monkeys (FIG. 18D); levels of APP levels in brains of monkeys (FIG. 18E); reversal of basal increases in $A\beta_{1-40/42}$ peptides by treatment of hepatic aPKC with liver-selective aPKC inhibitor ATM (60 mg/kg bw/day) and reversal of hyperinsulinemia (21) (FIG. 18C); and effects of 15-min insulin treatment (1 unit/kg bW) on $A\beta_{1-40/42}$ peptide levels in mouse models (FIGS. 18A-18C). Representative blots for 5- to 10-kDa $A\beta_{1-40/42}$ and 120-kDa APP are shown. Portrayed values of $A\beta_{1-40/42}$ and APP are the mean±SEM of (N) mice or monkeys. *P<0.05, P<0.01, and *P<0.001 (ANOVA) for comparison of HFF mice, ob/ob mice, or T2DM monkeys to respective controls. Con, control mice; Ins, insulin; OB, ob/ob mice; WT, wild type.
Figure 18B:
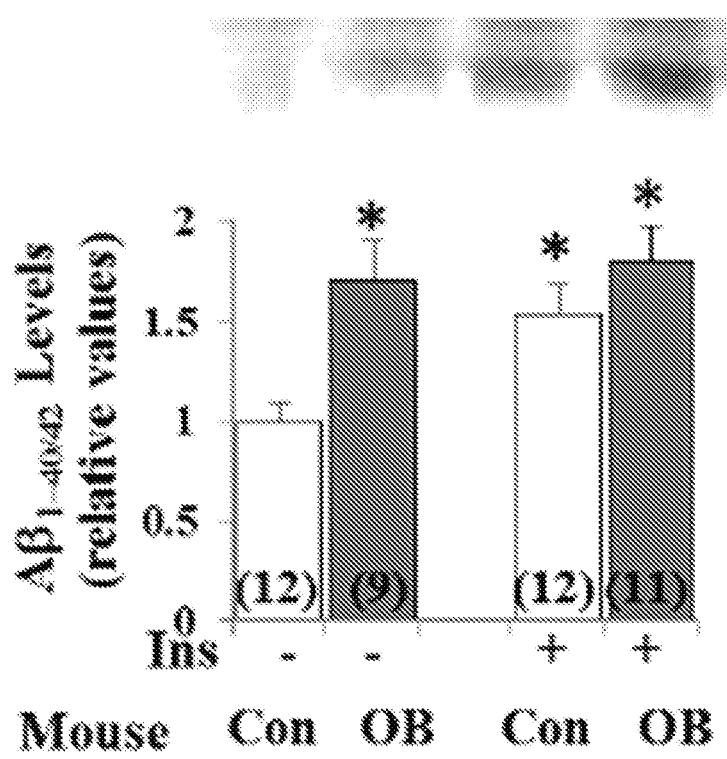
Figure 18C:
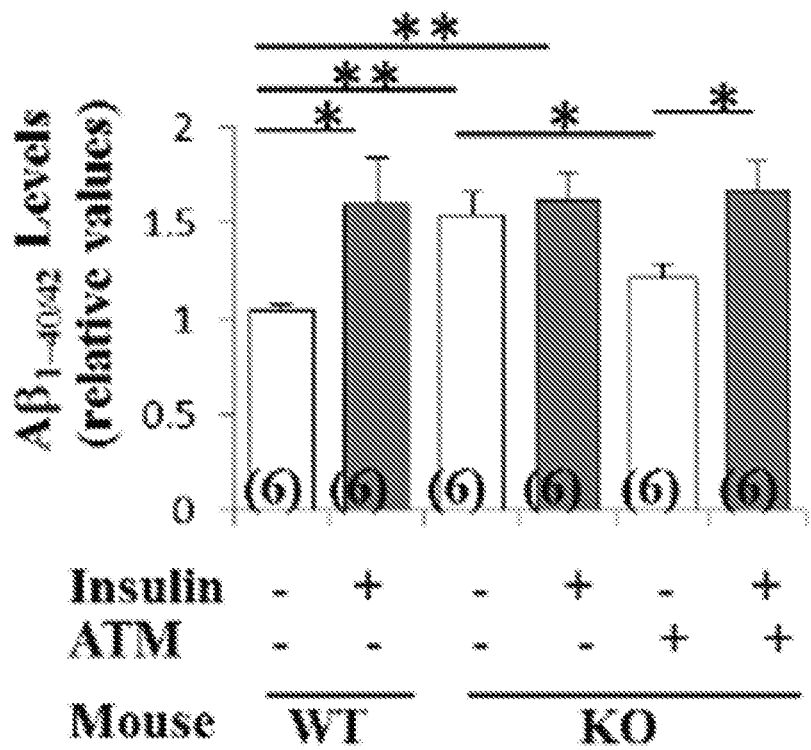
Figure 18D:
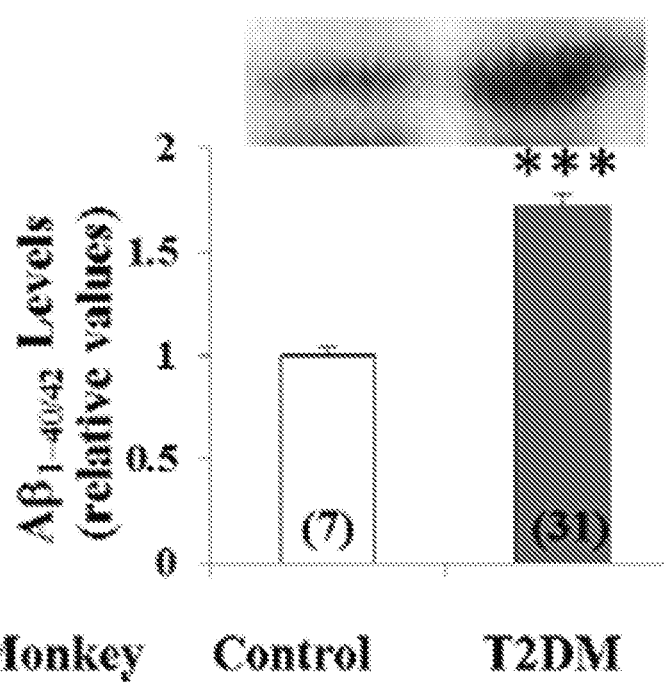
Figure 18E:
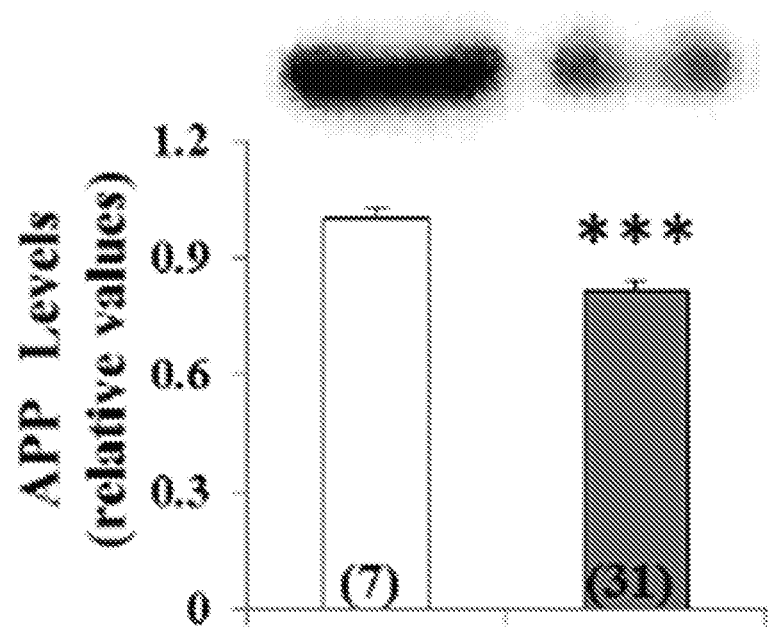
Figure 19A:
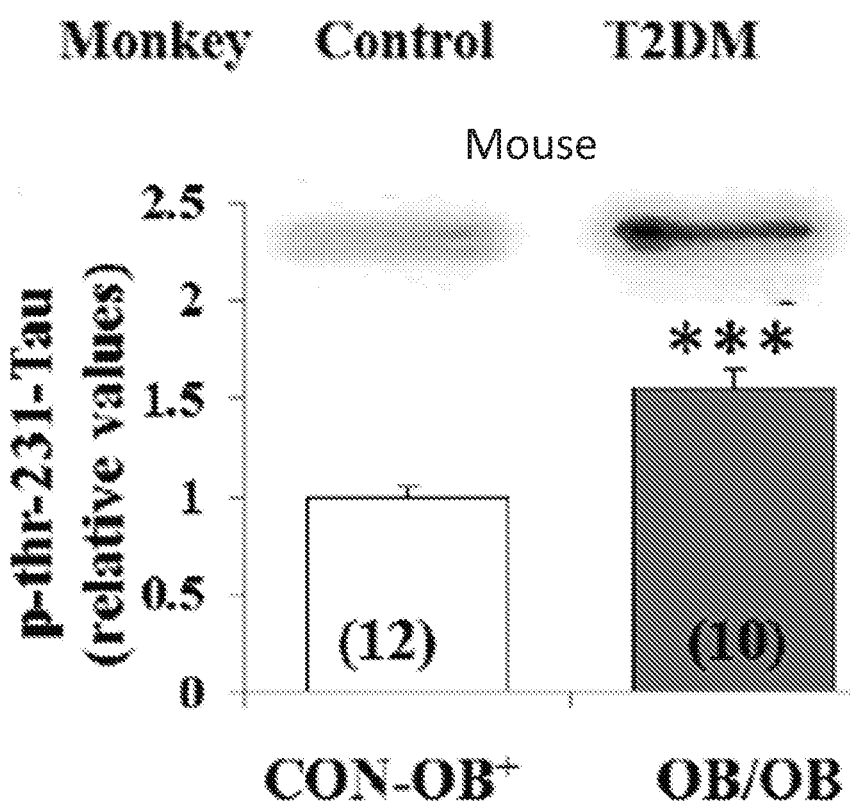
FIGS. 19A-19D show graphs and images of representative blots that can demonstrate resting/basal phosphorylation of Thr-231-tau and Ser-202-tau in brains of lean control ob+(CON-OB+) vs. ob/ob (OB/OB) mice (FIGS. 19A and 19C), and nondiabetic vs. T2DM monkeys (FIGS. 19B and 19D). Portrayed values of phosphoprotein levels are the mean±SEM of (N) mice or monkeys. *P<0.05 and ***P<0.001 (ANOVA) for comparison of ob/ob mice or T2DM monkeys with lean ob+ control mice or nondiabetic monkeys.
Figure 19B:
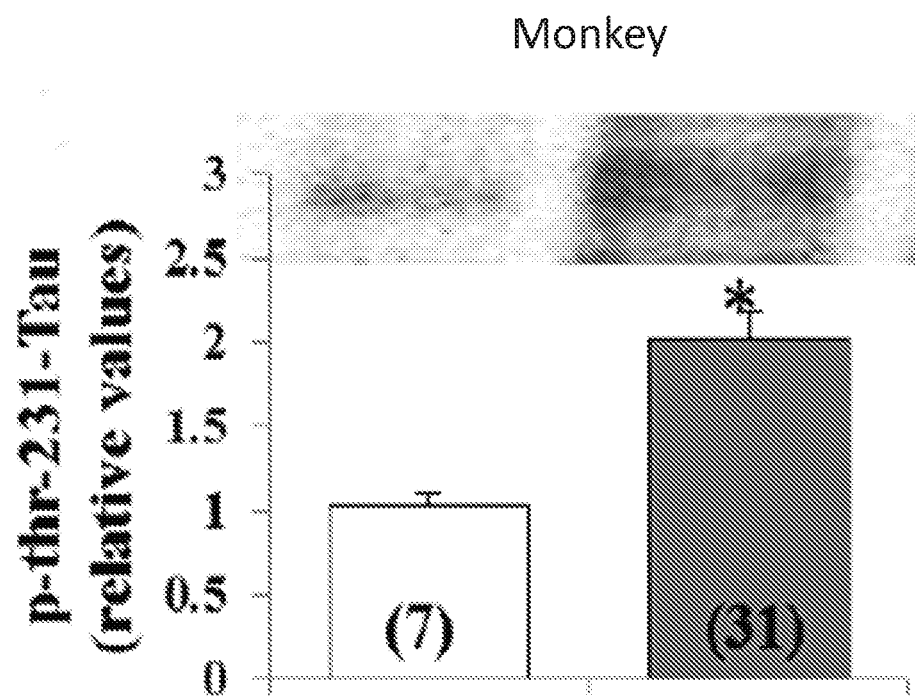
Figure 19C:
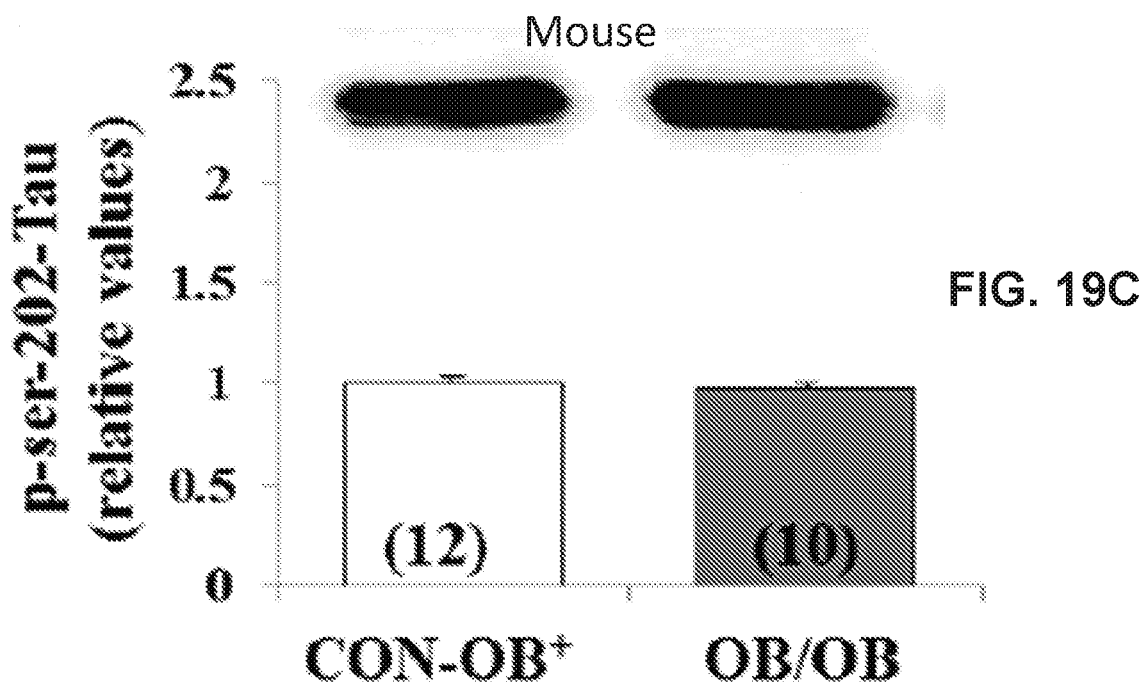
Figure 19D:
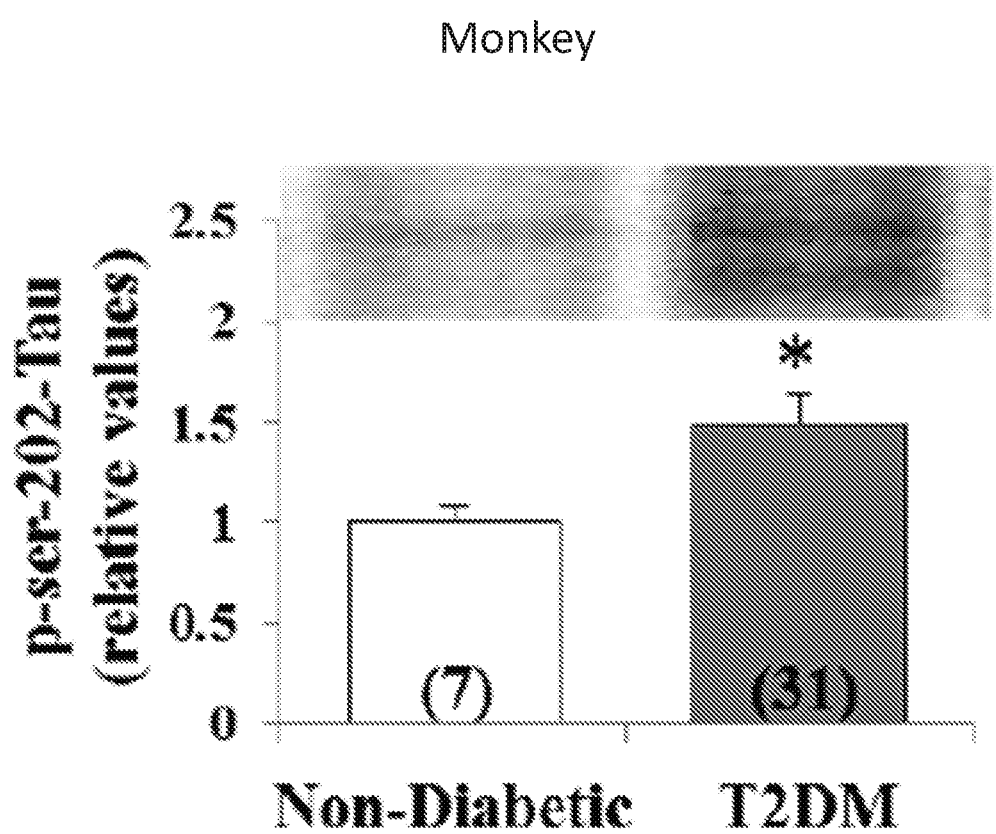
Figure 21A:
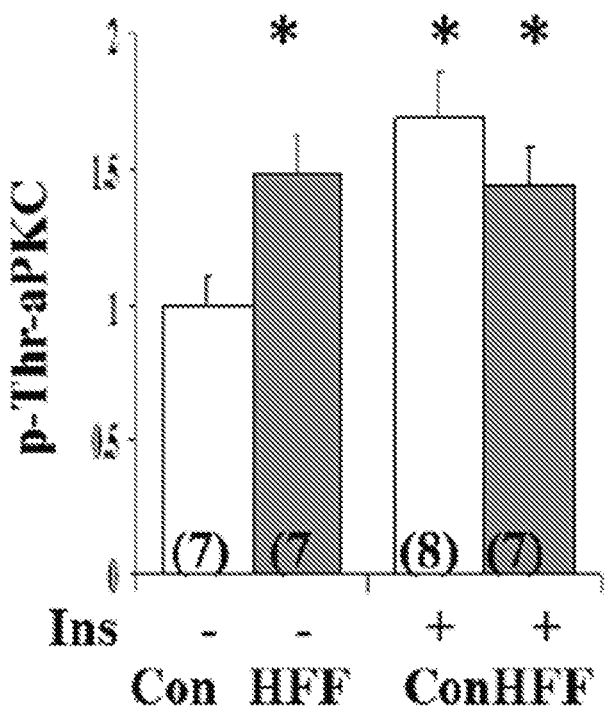
FIGS. 21A-21F show graphs that can demonstrate the effect of insulin on p-Thr-aPKC (FIG. 21A), p-Ser-473-Akt (FIG. 21B), p-ser-256-FoxO1 (FIG. 21C), p-ser-253-FoxO3a (FIG. 21D), p-Ser-9GSK3β (FIG. 21E), and p-ser-2248-mTOR (FIG. 21F) in the brains of control and HFF mice.
Figure 21B:
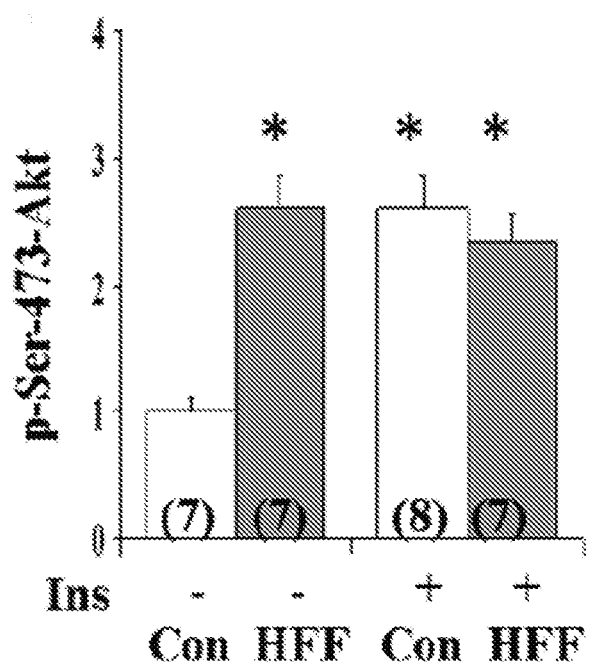
Figure 21C:
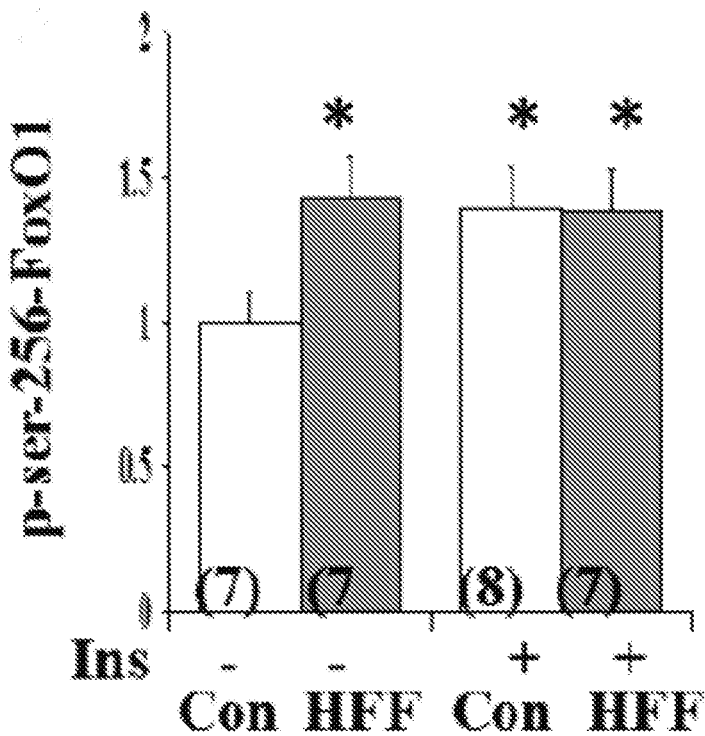
Figure 21D:
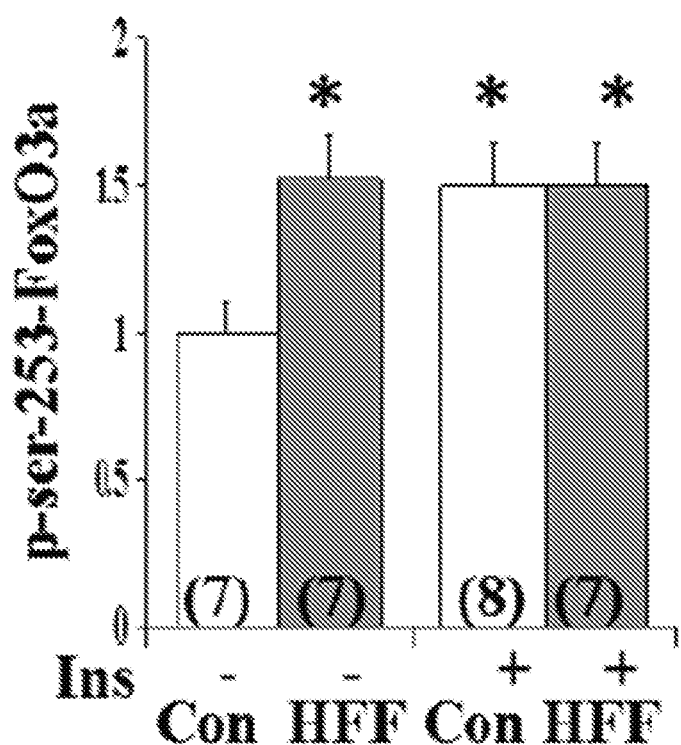
Figure 21E:
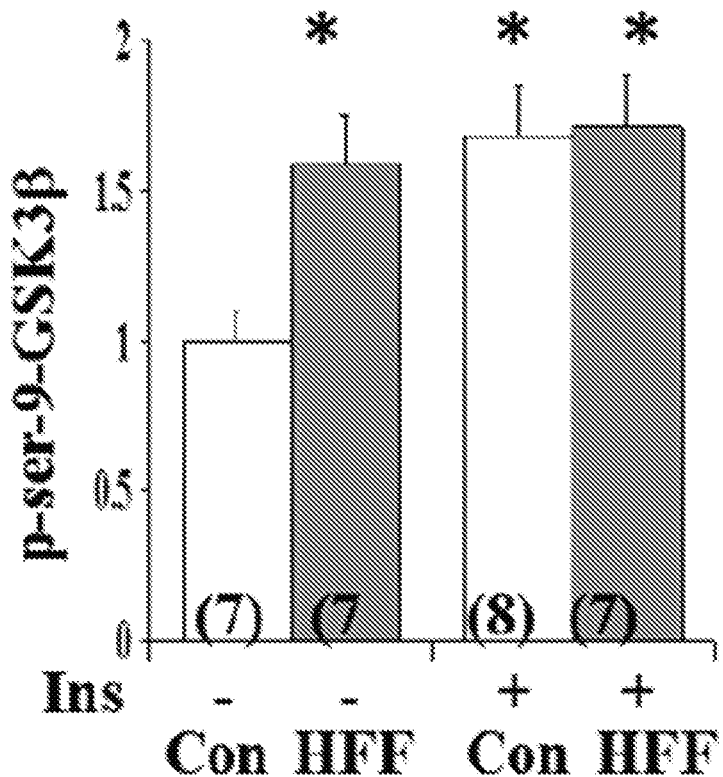
Figure 21F:
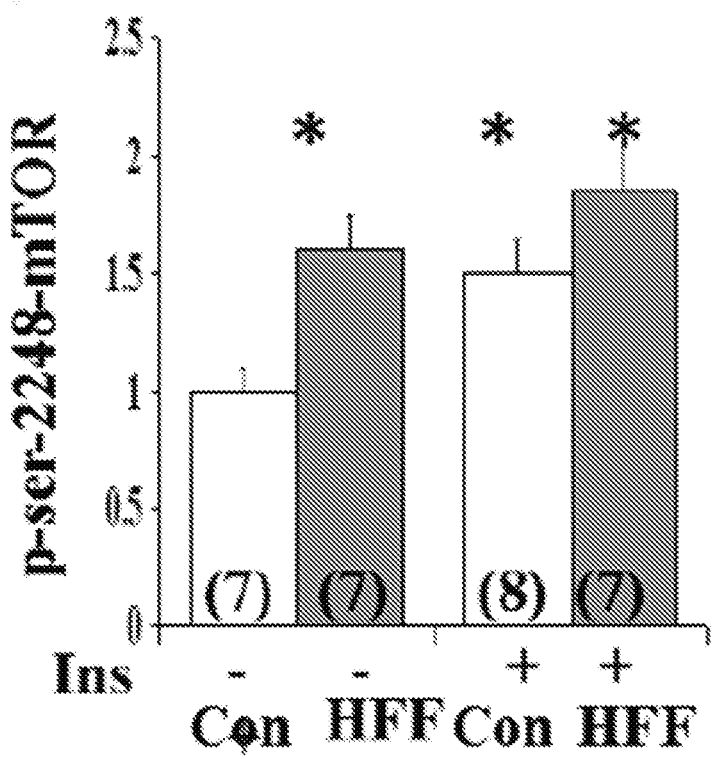

18E), but not in HFF or ob/ob mice (data not shown). Also note that the correction of hyperinsulinemia in Het-MλKO mice diminished resting/basal levels of Aβ$_{1-40/42}$ peptides and restored the ability of insulin to increase levels of Aβ$_{1-40/42}$ peptides (FIG. 18C).

Tau Phosphorylation in Mouse and Monkey Brain.

Despite hyperactivation of Akt and subsequent hyperphosphorylation of GSK3β in brains of HFF and Het-MλKO mice, phosphorylation of Thr-231-tau was not diminished, as might be expected with Akt-dependent decreases in GSK3β activity (13,14); also, phosphorylation of Thr-231-tau and Ser-202-tau was similarly not significantly altered in these mice (data not shown). Moreover, despite increased phosphorylation/inactivation of GSK3β, phosphorylation of Thr-231-tau was increased in both ob/ob mice and T2DM monkeys (FIGS. 19A-19D). Further, phosphorylation of Ser-202-tau was increased in brains of T2DM monkeys (FIGS. 19A-19D).

Insulin Receptor Levels in Mouse and Monkey Brains.

Although brain insulin receptor levels may be diminished in the AD brain (5,6), levels of the α-subunit and β-subunit of the insulin receptor were not altered in HFF mice, ob/ob mice, and T2DM monkeys (FIGS. 20A-20C).

Effect of Insulin on Signaling in Mouse Brains

Figure 10:
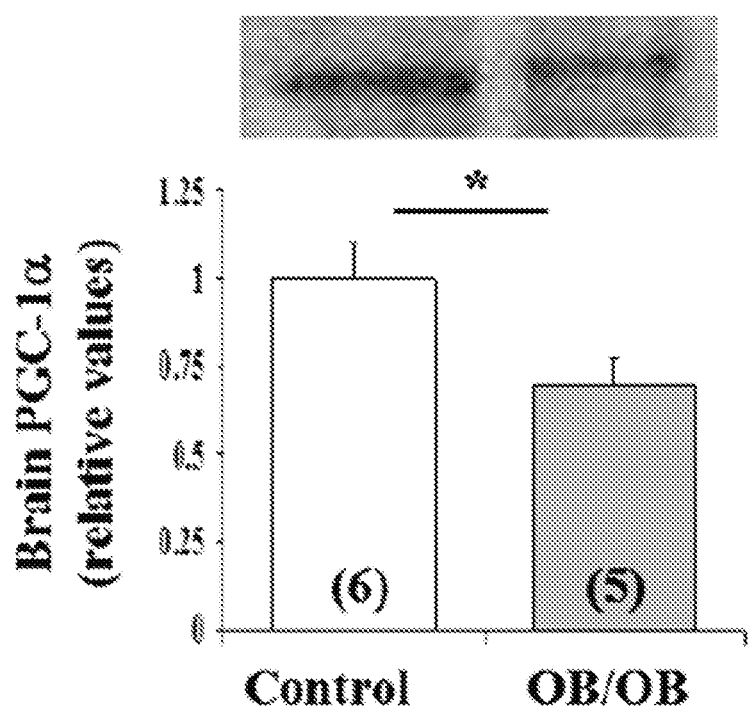
FIG. 10 shows a graph and image of representative blots that can demonstrate levels of brain PGC1-α in control and OB/OB mice.
Figure 11A:
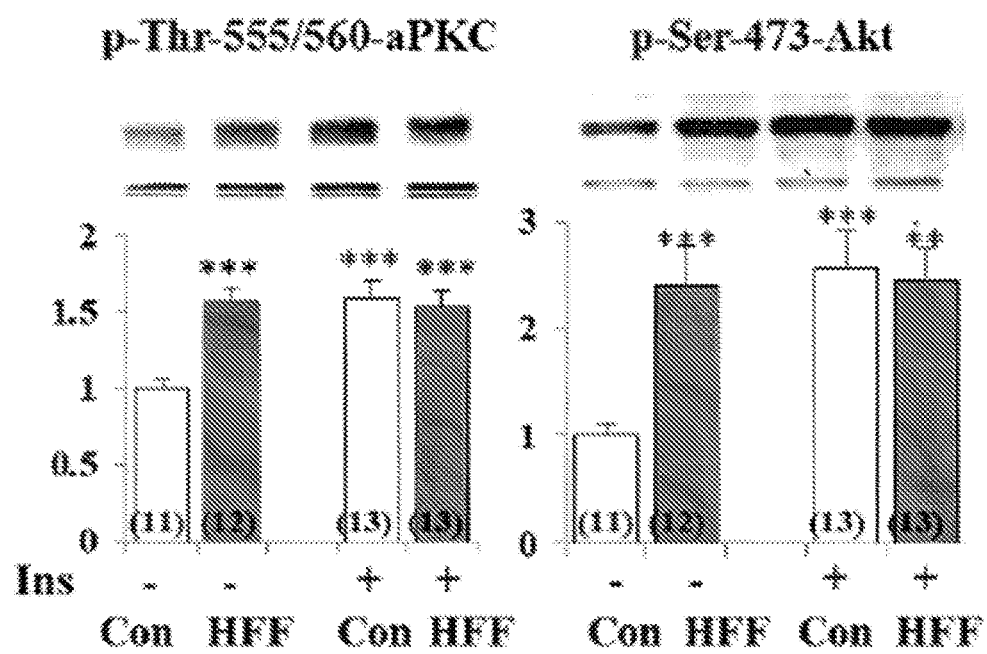
FIGS. 11A-11F show graphs and images of representative western blots that can demonstrate resting/basal and insulin-stimulated phosphorylation/activity of aPKC and Akt (FIGS. 11A and 11B) and phosphorylation of Akt substrates FOXO1, FOXO3a (FIGS. 11C and 11D), GSK3β, and mTOR (FIGS. 11E and 11F) in brains of control (Con), HFF, and ob/ob (OB) mice. Where indicated, mice were treated with insulin (Ins) (1 unit/kg bw i.p.) 15 min before being killed. Representative blots of phosphoproteins (top bands) and unaltered total protein levels (bottom bands) are shown. Portrayed values of phosphoprotein levels are mean±SEM of (N) mice. $P<0.01$ and *$P<0.001$ for comparison of HFF or OB values to control values (ANOVA).
Figure 11B:
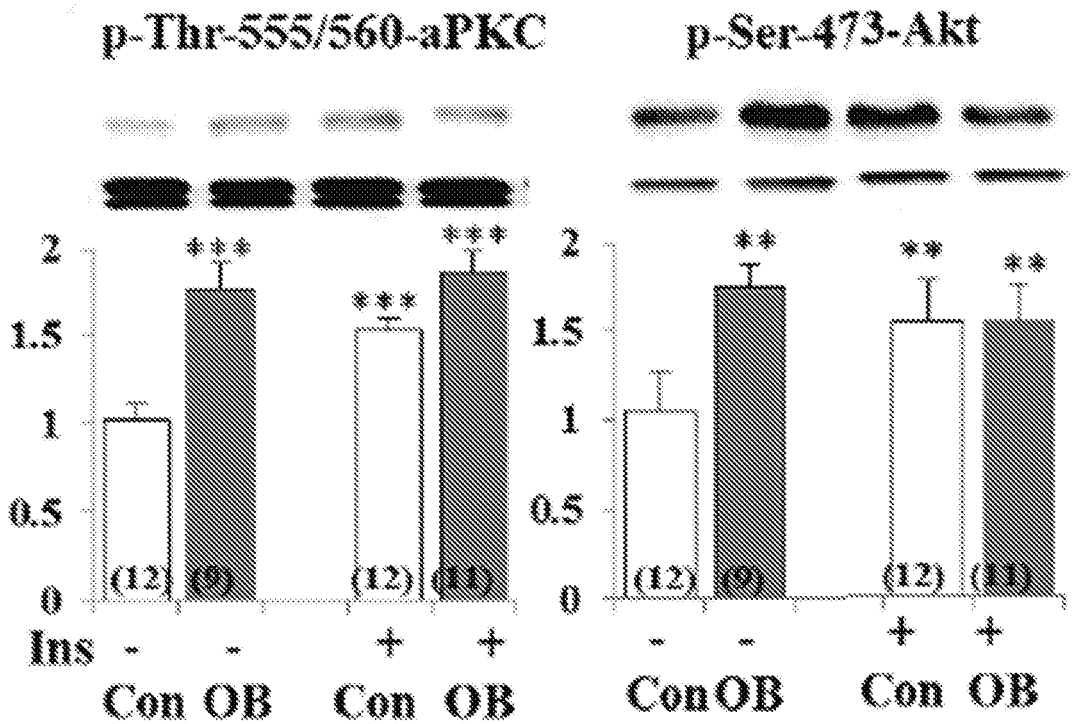
Figure 11C:
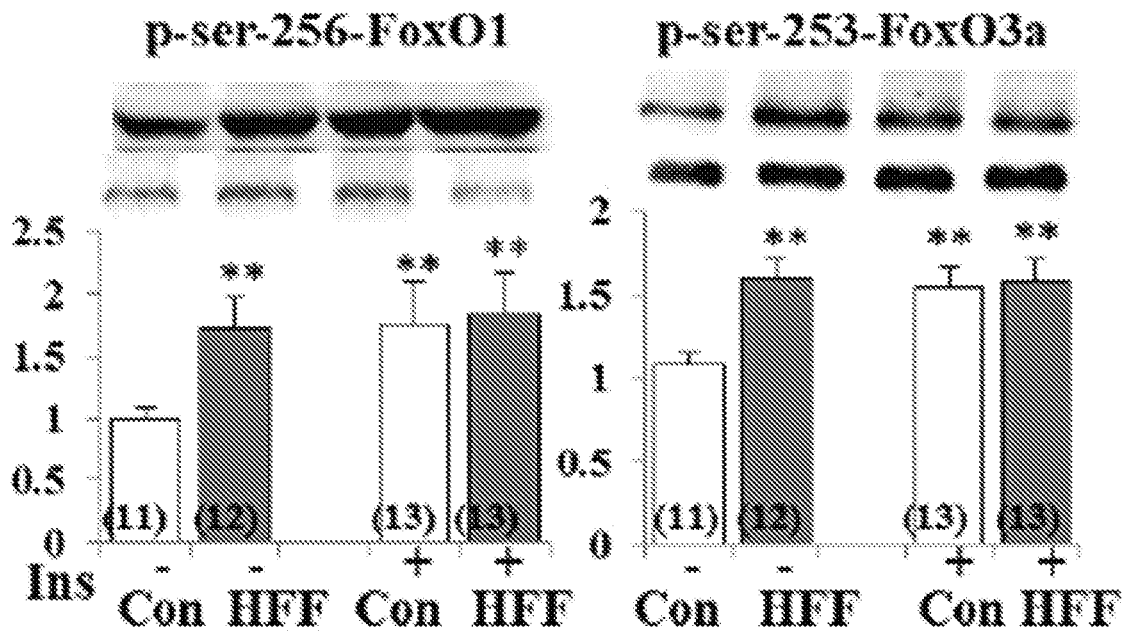
Figure 11D:
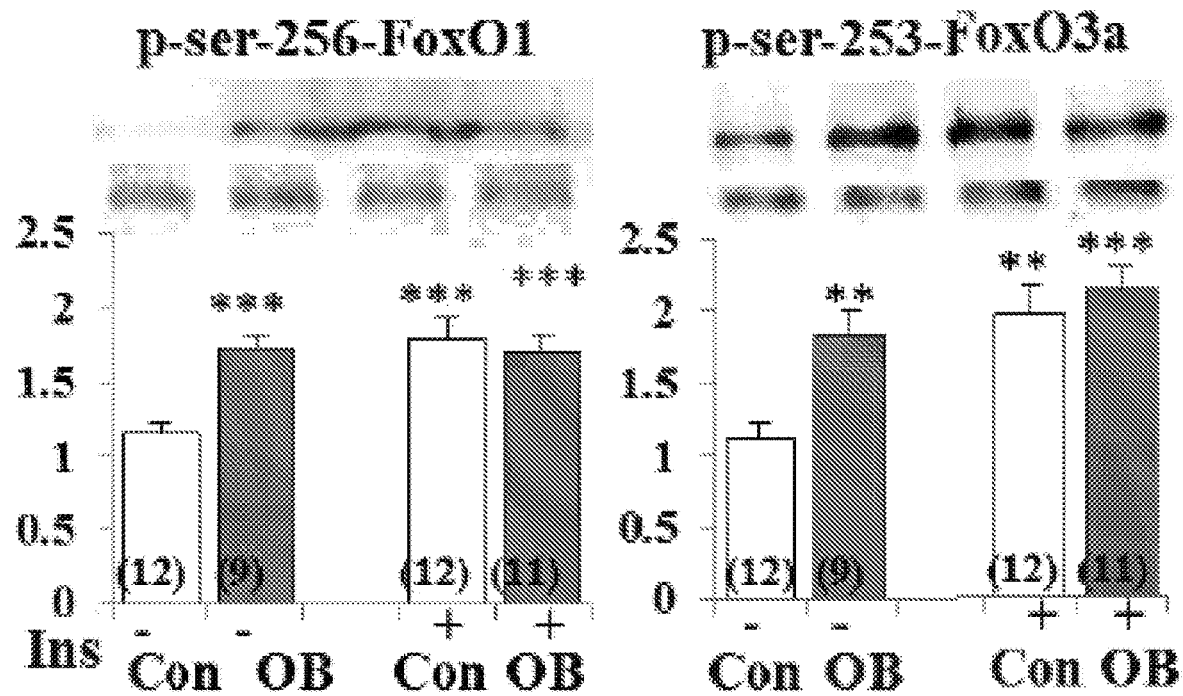
Figure 11E:
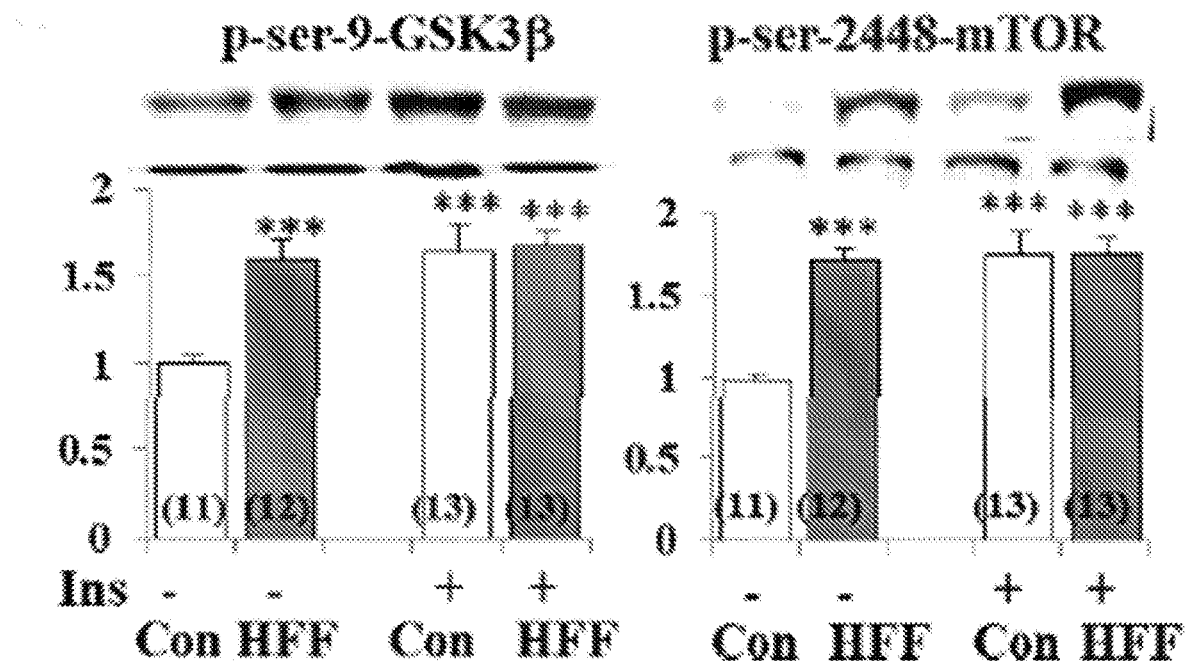
Figure 11F:
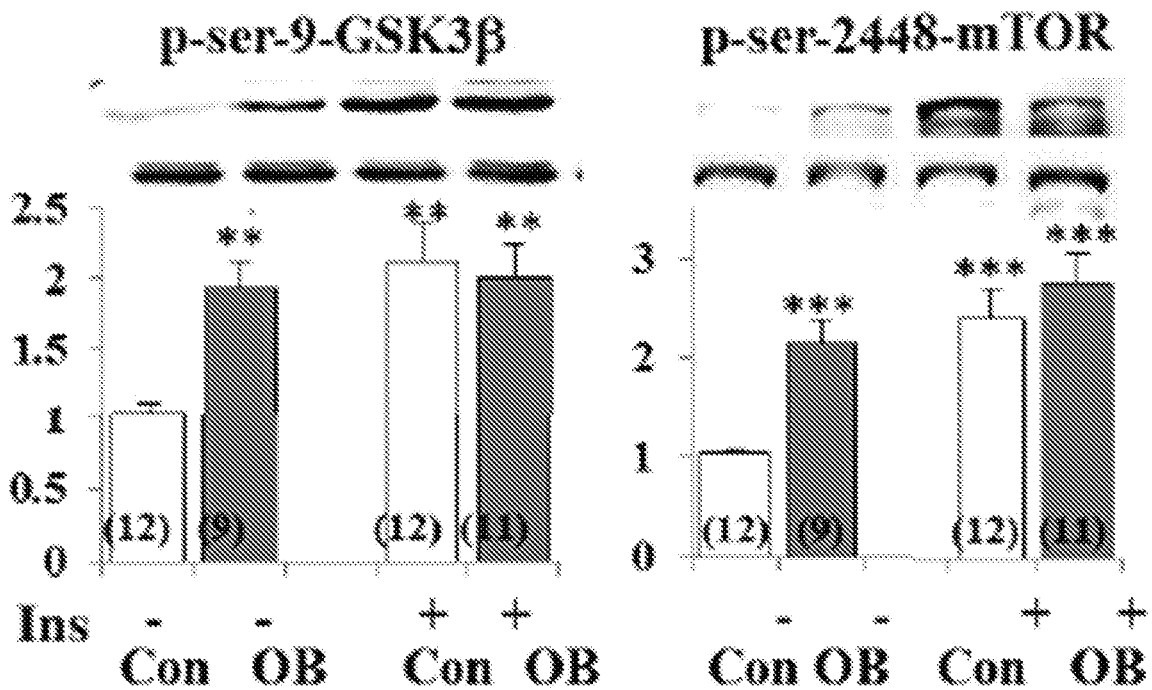
Figure 12A:
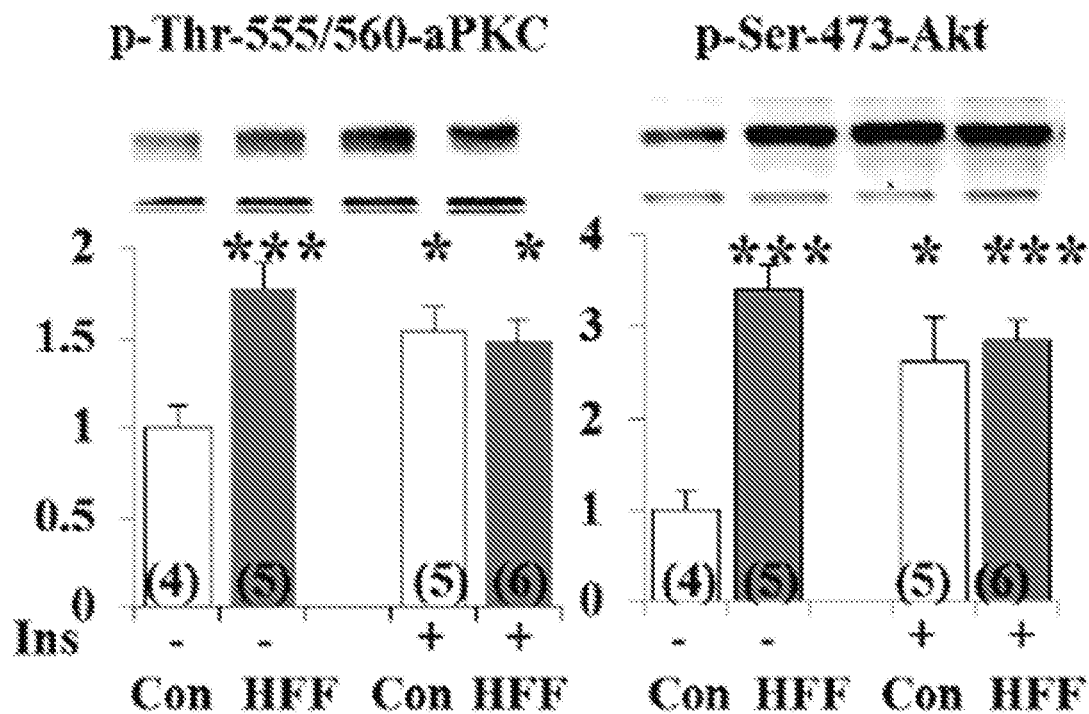
FIGS. 12A-12F show graphs and images of representative western blots that demonstrate resting/basal and insulin-stimulated phosphorylation/activity of aPKC and Akt (FIGS. 12A and 12B) and phosphorylation of Akt substrates FOXO1, FOXO3a (FIGS. 12C and 12D), GSK3β, and mTOR (FIGS. 12E and 12F) in brains of control (Con), high-fat fed (HFF), and ob/ob (OB) mice. Also shown are representative blots of phosphoproteins (top bands) and unaltered total protein levels (bottom bands).
Figure 12B:
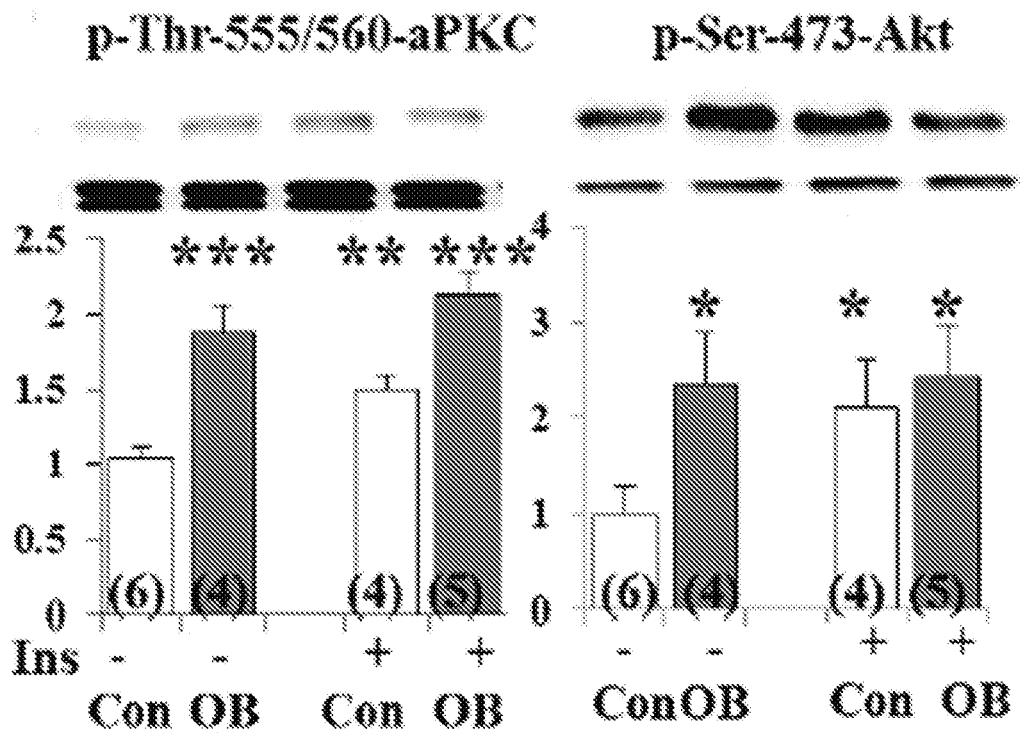
Figure 12C:
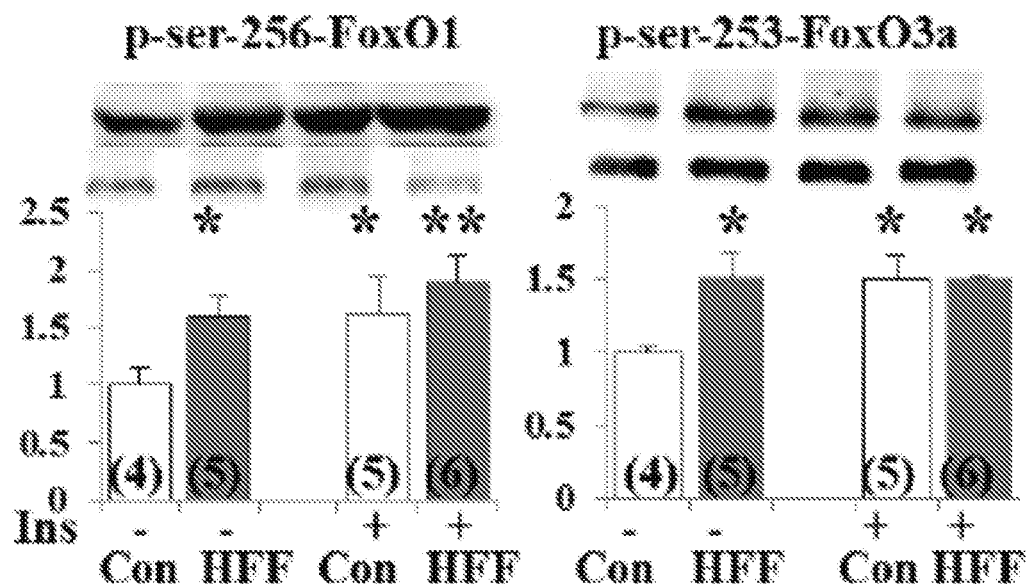
Figure 12D:
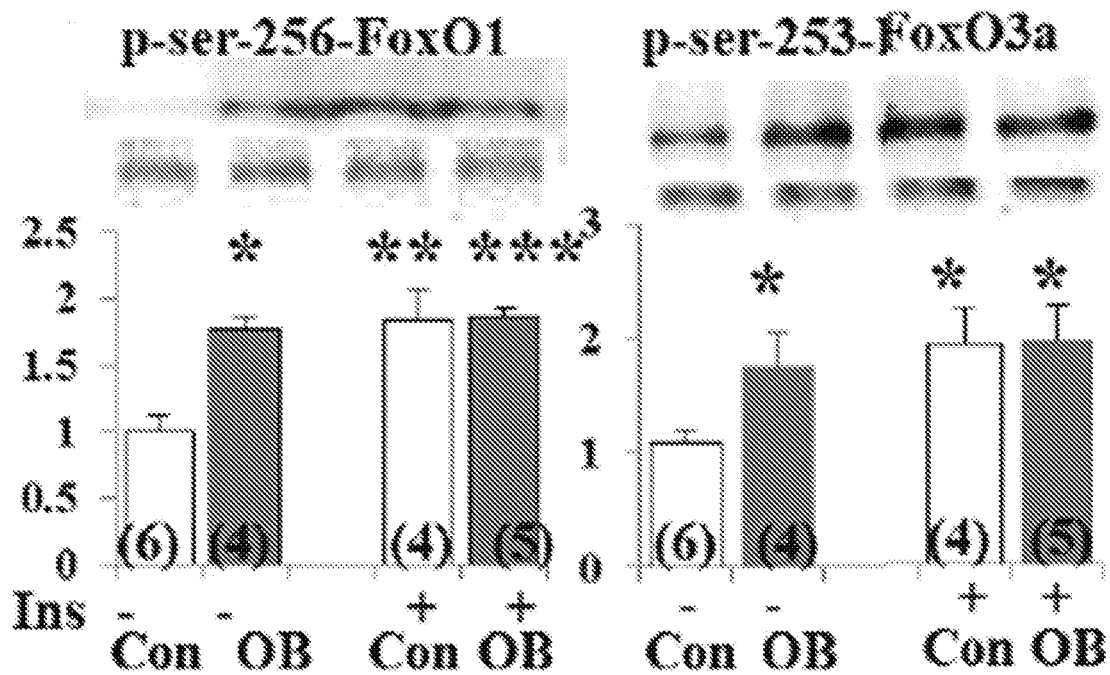
Figure 12E:
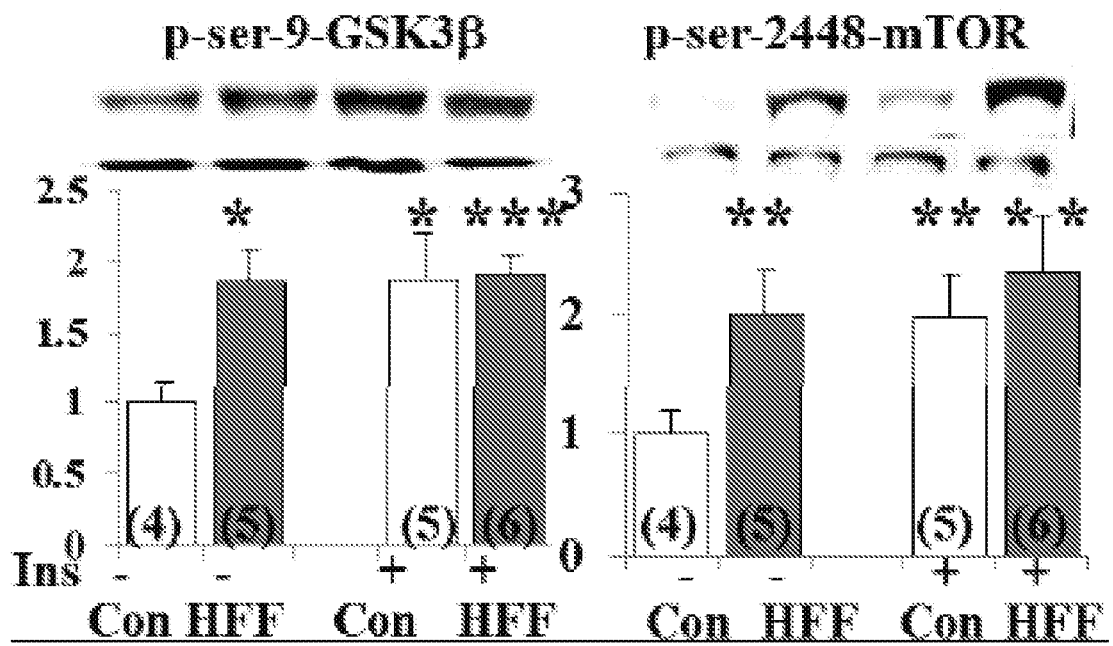
Figure 12F:
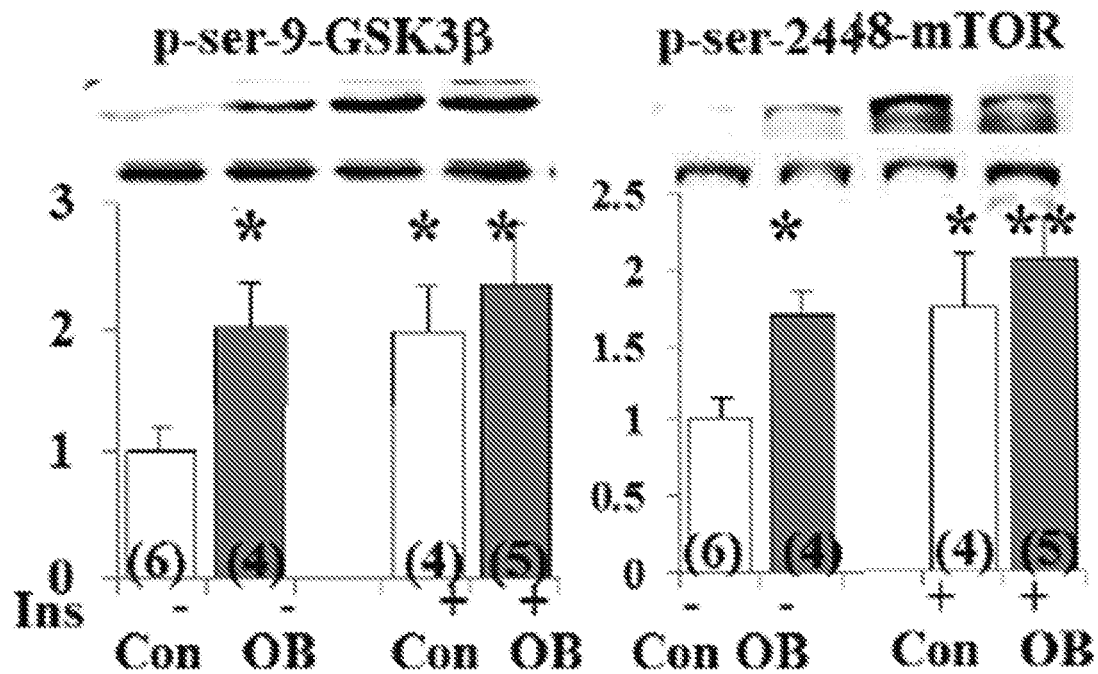
Figure 13A:
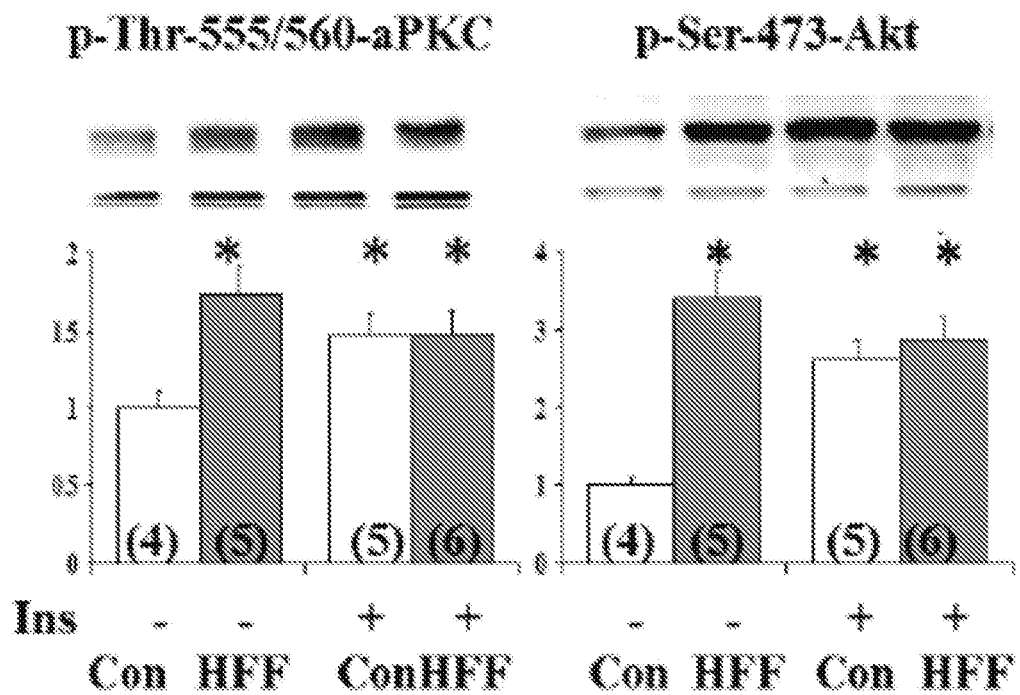
FIGS. 13A-13F show graphs and images of representative western blots that demonstrate resting/basal and insulin-stimulated phosphorylation/activity of aPKC and Akt (FIGS. 13A and 13B) and phosphorylation of Akt substrates FOXO1, FOXO3a (FIGS. 13C and 13D), GSK3β, and mTOR (FIGS. 13E and 13F) in brains of control (Con), high-fat fed (HFF), and ob/ob (OB) mice. Also shown are representative blots of phosphoproteins (top bands) and unaltered total protein levels (bottom bands).
Figure 13B:
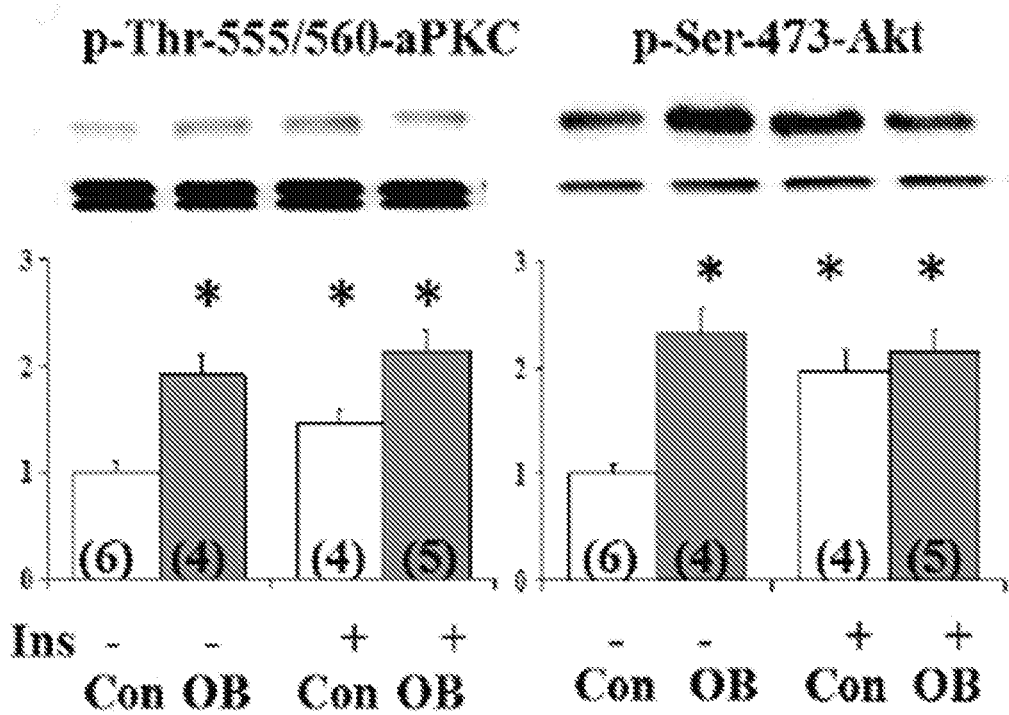
Figure 13C:
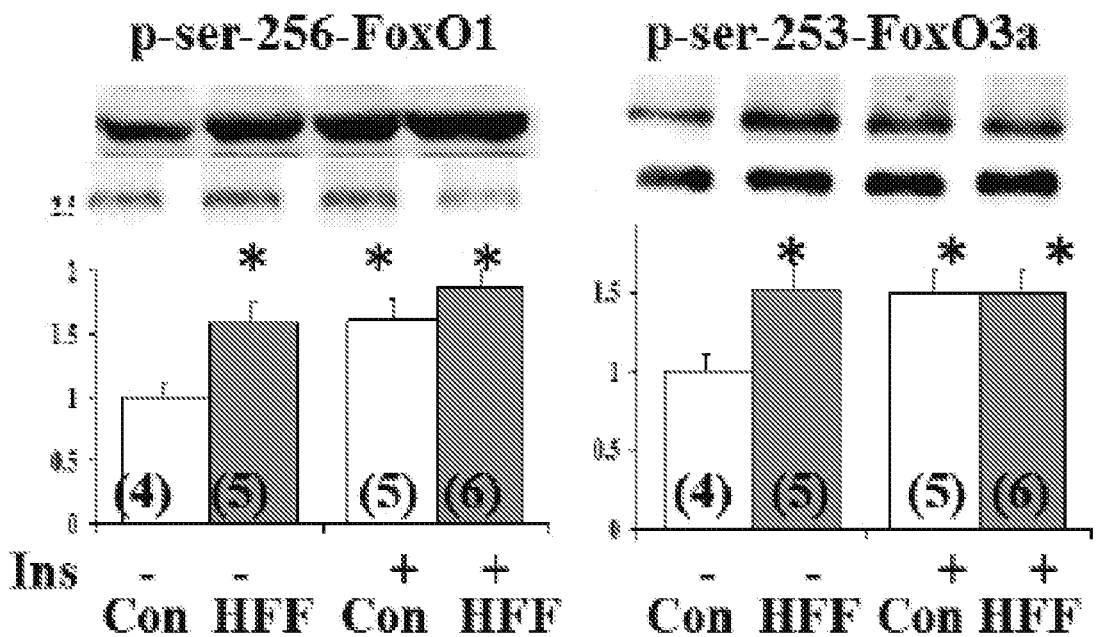
Figure 13D:
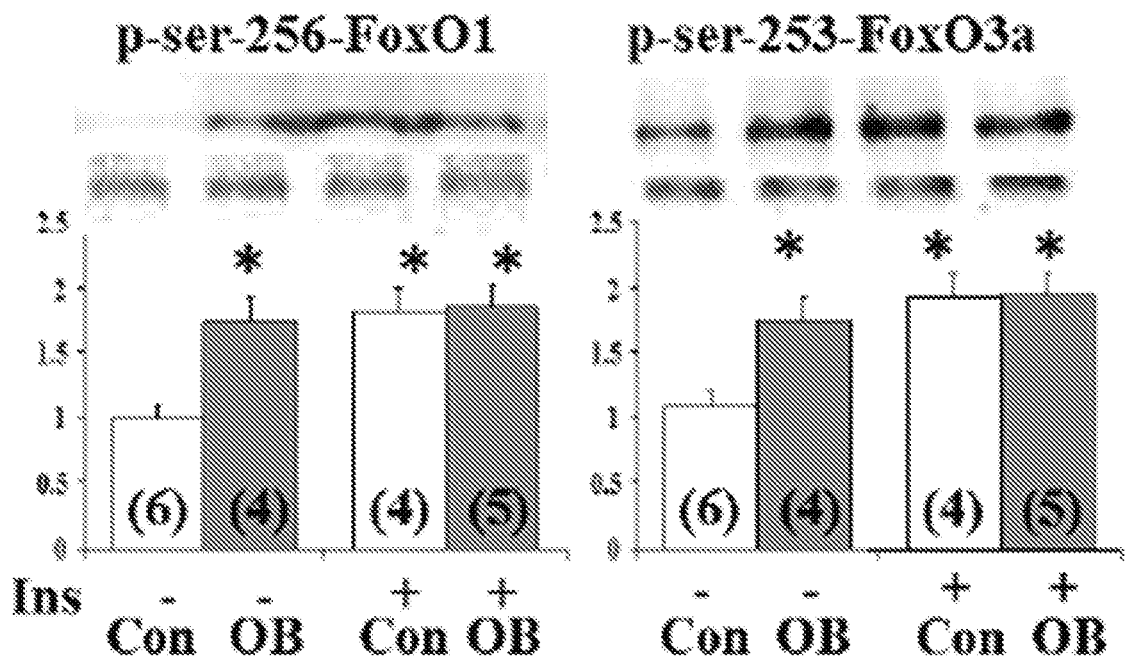
Figure 13E:
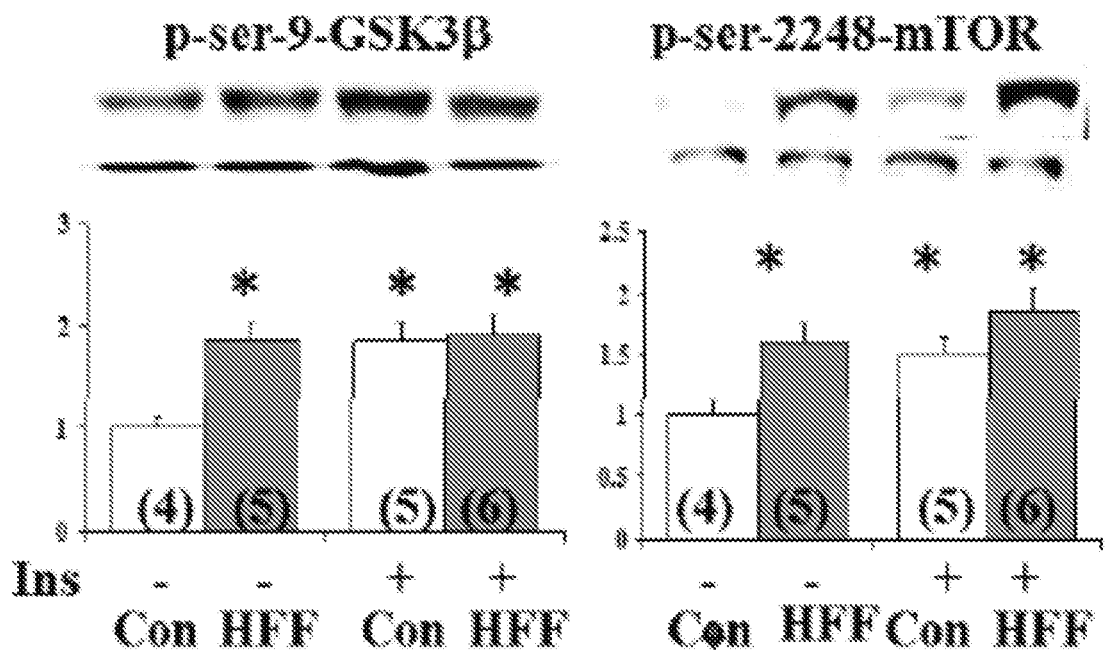
Figure 13F:
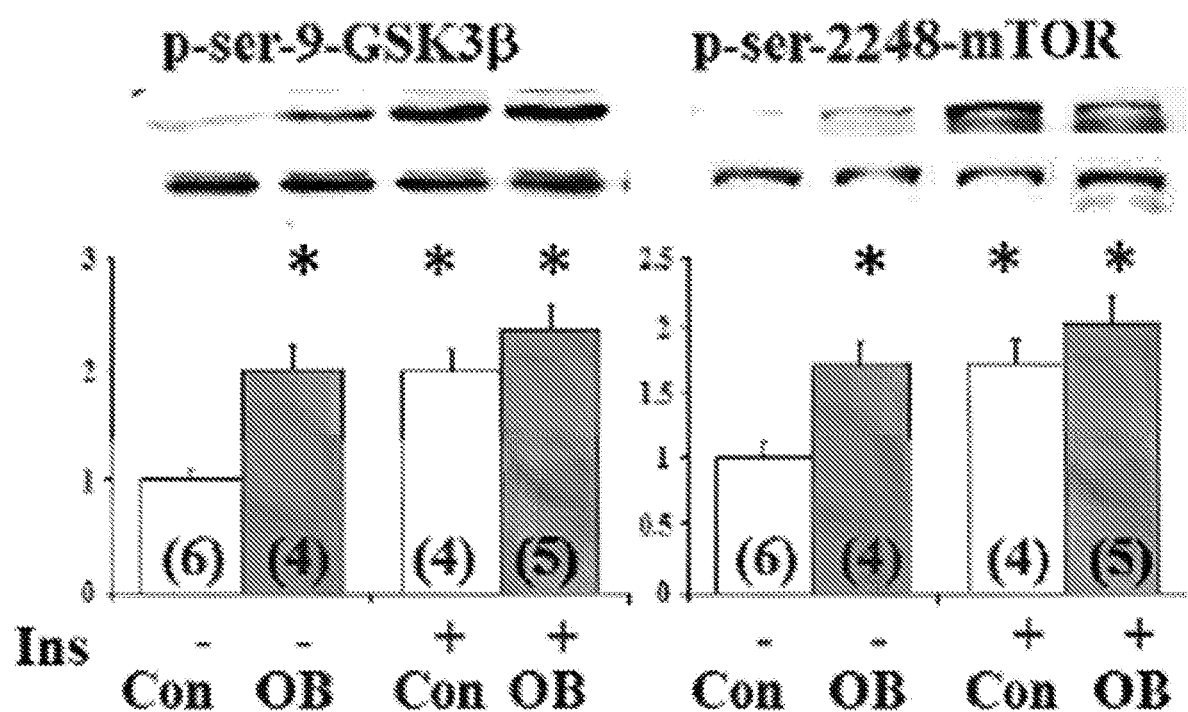
Figure 14A:
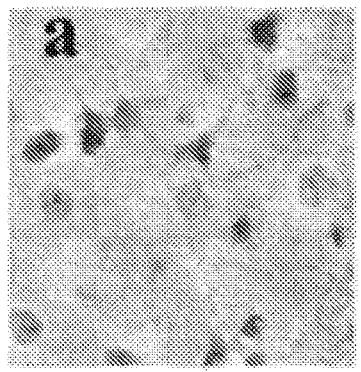
FIGS. 14A-14K showing representative microscopic images and graphs that can demonstrate phosphorylation/activation of Akt in anterior cortical and hippocampal regions of brains of control (Con) (FIGS. 14A, 14D, and 14G), HFF (FIGS. 14B, 14E, and 14H), and ob/ob (OB) (FIGS. 14C, 14F, and 14I) mice. Microscopic images (FIGS. 14A-14I) show representative examples of (brown) immunostaining of p-Ser-473-Akt.
Figure 14B:
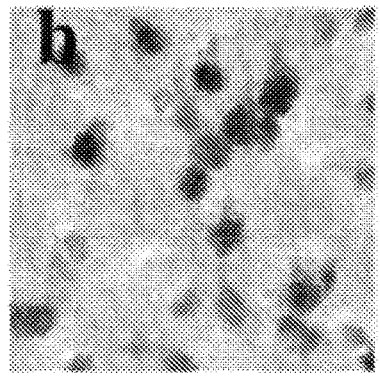
Figure 14C:
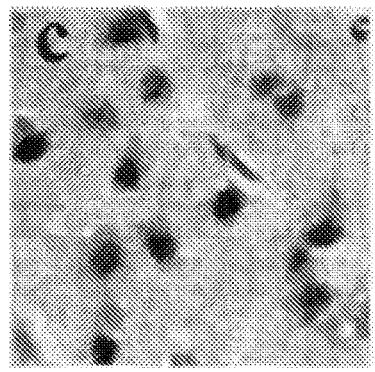
Figure 14D:
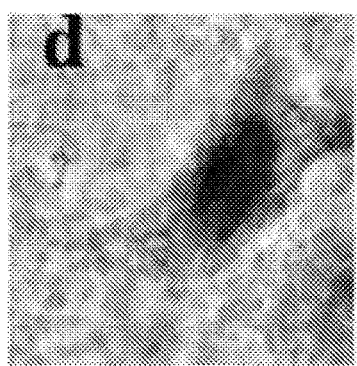
Figure 14E:
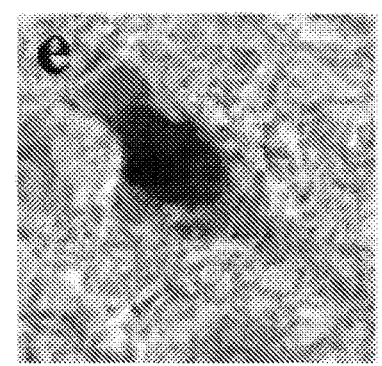
Figure 14F:
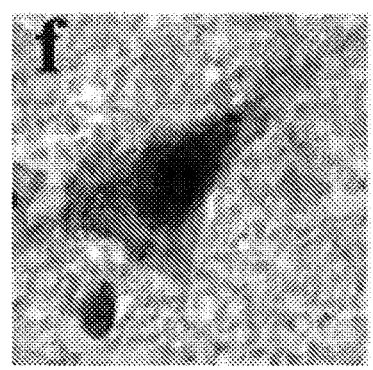
Figure 14G:
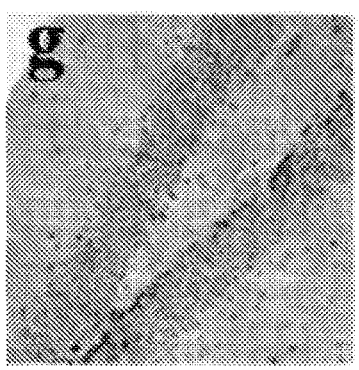
Figure 14H:
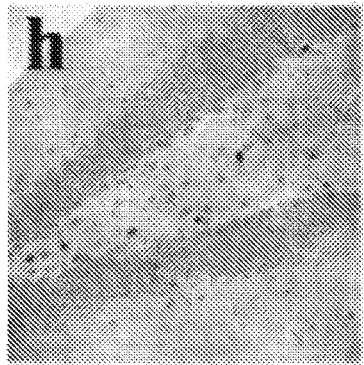
Figure 14I:
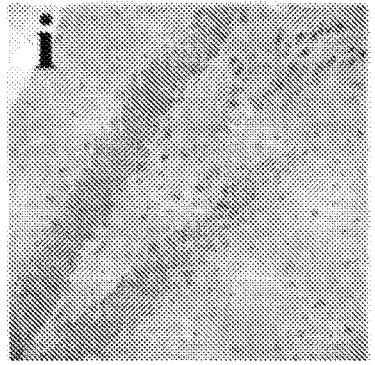
Figure 14J:
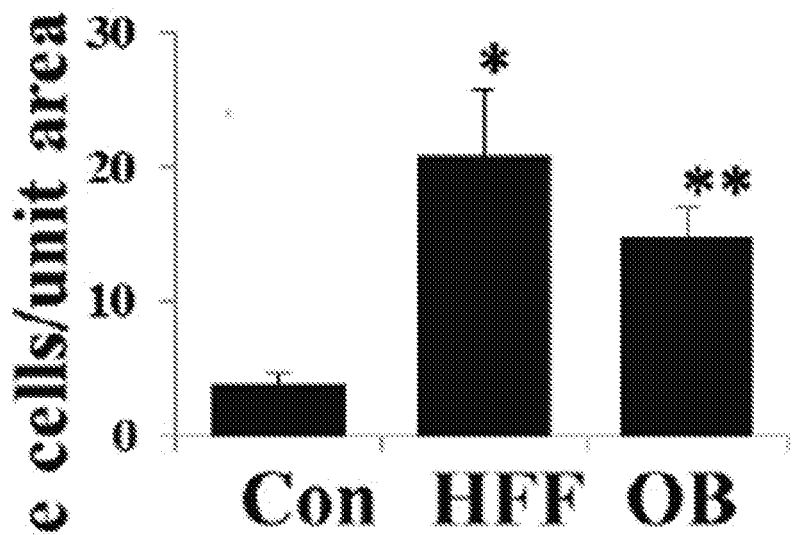
Figure 14K:
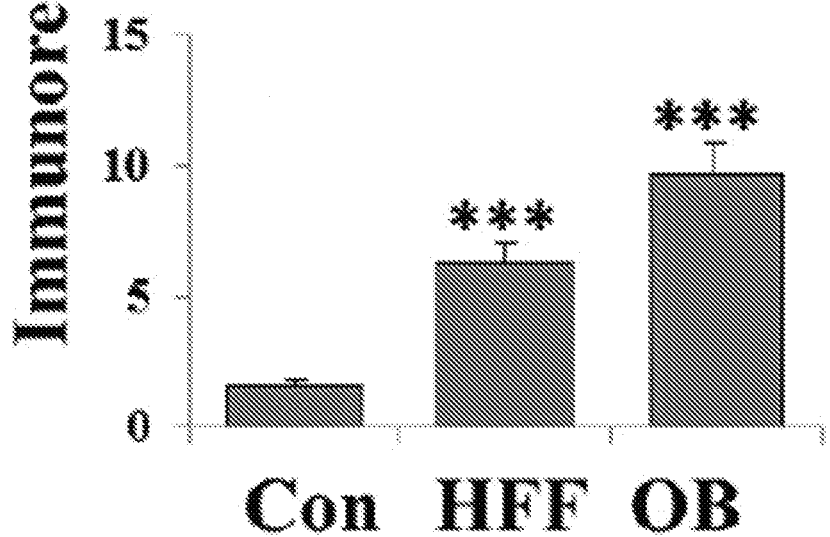
Figure 22A:
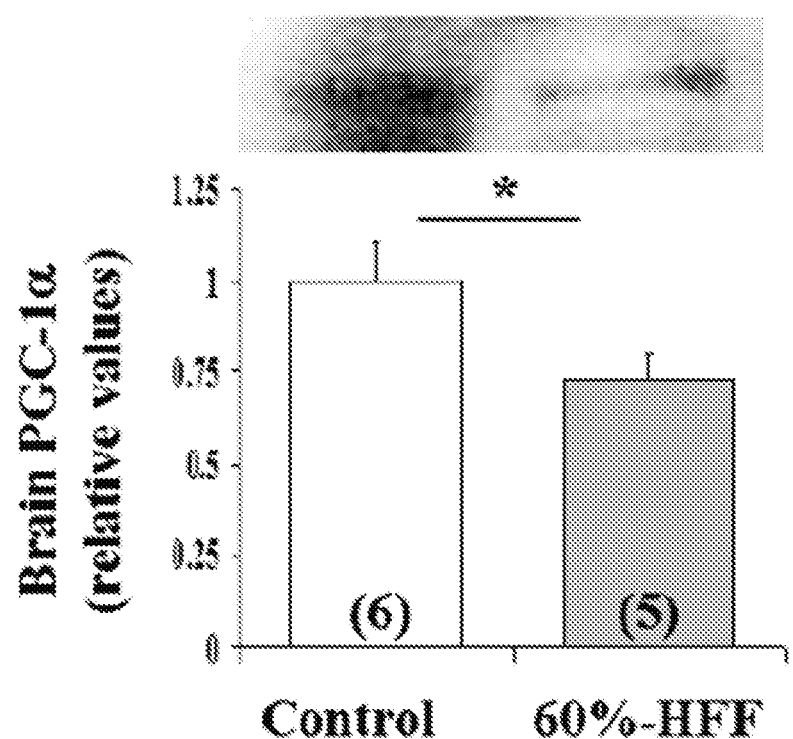
FIGS. 22A-22B show graphs and images of representative blots that can demonstrate brain PGC1-α in control and 60%-HFF mice (FIG. 22A) or 40%-HFF mice (FIG. 22B).
Figure 22B:
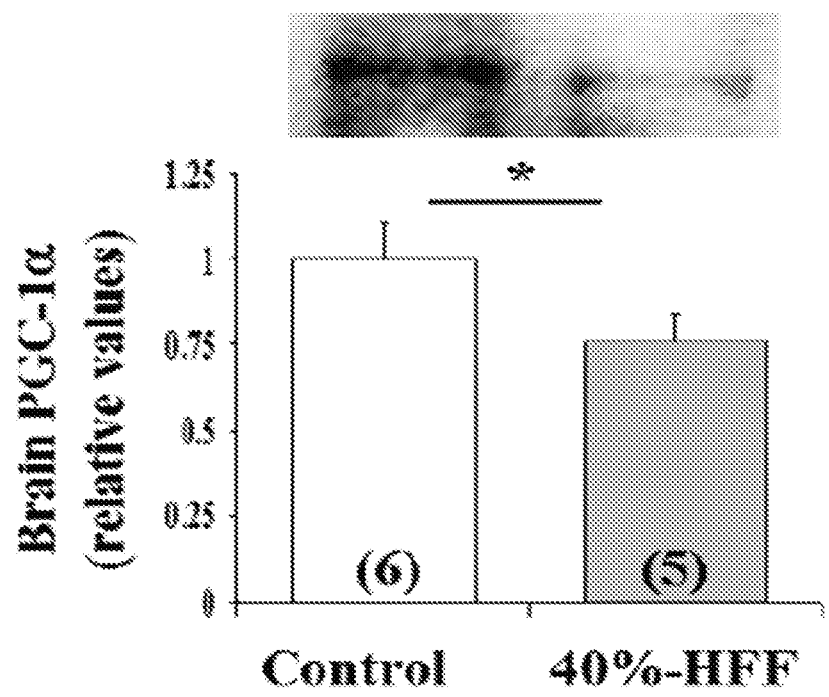

The effect of insulin stimulation on p-Thr-aPKC, p-Ser-473-Akt, p-ser-256-FoxO1, p-ser-253-FoxO3a, p-Ser-9GSK3β, and p-ser-2248-mTOR in control and HFF mice. Results are shown in FIGS. 21A-21F. Brain PGC-1α was also evaluated in 60% and 40%-HFF mice and OB/OB mice. Results are shown in FIGS. 10 and 22A-22B.

Discussion

The data presented in this Example can demonstrate that insulin signaling to the two major protein kinases that elicit many/most insulin effects, Akt and aPKC, is increased in brain, both at early stages of insulin resistance in HFF, ob/ob, and Het-MλKO mice and at later stages in obese/T2DM monkeys. The findings of increased insulin signaling in brains of insulin-resistant mice and monkeys are important because this hyperinsulinization leads to or is accompanied by not only the downregulation of factors needed for maintaining neuronal function and longevity, FOXOs and PGC-1α, but also by the upregulation of factors that may contribute directly to AD pathology, Aβ$_{1-40/42}$ peptides and p-tau. Accordingly, excessive activation of insulin signaling in brain can explain, in part, the linkage between obesity/T2DM and AD.

The data presented in this Example can demonstrate, contrary to previous speculations (9-12), insulin resistance in brain and the resultant increases in the activity of GSK3β are unlikely to serve as long-standing predisposing factors for AD development, and impairments in insulin-signaling factors that are seen in brains of human AD patients (5,6, 9-12) are either later-appearing predisposing abnormalities or consequences, rather than predisposing causes, of AD pathology.

Unlike muscle, where insulin signaling to Akt and aPKC is downregulated in insulin-resistant DIO mice (16,17) and humans with T2DM (28), and unlike liver, where insulin signaling to Akt (but not aPKC, which is hyperactivated by lipids plus hyperinsulinemia) is downregulated in obese and humans with T2DM (18,19), insulin signaling to both Akt and aPKC is hyperactive in brain. This paradoxical retention of central nervous system (CNS) insulin signaling in insulin-resistant states may reflect that insulin controls Akt and aPKC by different IRSs in different tissues. Thus, in muscle IRS-1 controls both Akt and aPKC, and IRS-1 is commonly downregulated in insulin-resistant conditions; however, in liver, whereas IRS-1 mainly controls Akt and is commonly downregulated, IRS-2 controls aPKC and is well conserved in T2DM (18,19). That total brain and anterior cortical and hippocampal areas were resistant to downregulation in presently studied insulin resistance models may reflect that IRS-2 preferentially mediates certain CNS functions (29); however, the role of IRS-1 in relation to IRS-2 throughout the CNS remains uncertain.

The observed increases in brain FOXO phosphorylation are the opposite of decreases in hepatic FOXO1 that are seen in insulin-resistant states (FIG. 1). In this regard, during insulin action in normal liver, Akt-dependent phosphorylation of FOXO1 occurs in a subcellular compartment defined by the 40-kDa scaffolding protein, WD (tryp-asp-x-x) repeat, propeller-like, FYVE-containing protein (WD40/ProF), and, similar to Akt, aPKC is recruited to the WD40/ProF platform and may restrain Akt but still allows sufficient FOXO1 phosphorylation to inhibit PGC-1α and gluconeogenic enzyme expression (16,17). However, in livers of HFF (16), ob/ob (17), and Het-MλKO (M.S., R.I., R.V.F., unpublished observations) mice and obese human and humans with T2DM (18,19), aPKC accumulation on the WD40/ProF platform is excessive owing to increases in ceramide (16,17,19), a potent noninsulin activator of hepatic aPKC (16) (FIG. 1). Moreover, these excessive increases in hepatic aPKC activity in insulin-resistant states markedly reduce Akt2 levels on the WD40/ProF platform (16-19), thus specifically and substantially impairing FOXO1 phosphorylation, thereby increasing PGC-1α level and the expression of gluconeogenic enzymes (FIGS. 19A-19D). The ensuing hyperinsulinemia, at least initially, hyperactivates hepatic Akt and further activates ceramide-activated hepatic aPKC, thus increasing hepatic lipogenesis (16-19). Most importantly, in vivo treatment of HFF (16), ob/ob (17), and Het-MλKO (21) mice and in vitro treatment of hepatocytes of humans with T2DM (18,19) with liver-selective aPKC inhibitors diminishes hepatic aPKC association with WD40/ProF, restores hepatic Akt association with WD40/ProF, increases hepatic FOXO1 phosphorylation, decreases the level of PGC-1α, and decreases the expression of hepatic gluconeogenic and lipogenic enzymes. These hepatic improvements are followed by reductions in serum insulin levels (21), which, as presently seen in Het-MλKO mice, were sufficient to largely normalize brain insulin signaling.

Increases in Akt-dependent phosphorylation of FOXO proteins in brains of presently studied insulin-resistant models are noteworthy because considerable evidence suggests that phosphorylation-induced inhibition of FOXO1, FOXO3a, FOXO4, and FOXO6 can diminish transcriptional functions of FOXOs and FOXO1-dependent PGC-1α, which, over long periods, may be detrimental. Thus, the brain contains FOXO1, FOXO3a, FOXO4, FOXO6, and insulin via Akt phosphorylates and inhibits all brain FOXOs (30-32) and FOXO1-regulated PGC-1α. Moreover, FOXOs have important functions in brain, as revealed by the fact that neuronal-specific knockout of either FOXO3a (33) or FOXO1/FOXO3a/FOXO4 (34) provokes initial increases in neuronal proliferation (perhaps reflecting initially decreased apoptosis), followed later, by impairments in neuronal differentiation, proliferation, survival, self-renewal, and atrophy as these knockout mice aged. Accordingly, it was proposed that, with diminished FOXO action, there were reduced responses to oxidative stress and hypoxia, upregulation of Wnt signaling, increased expression of the abnormal spindle-like microcephaly-associated gene (Aspm), and a failure to promote reparative quiescence that, in time, led to cellular exhaustion (33,34). And, more recently, it was found (35) that knockout of FOXO6, found almost exclusively in brain, or specific inhibition of FOXO6 in hippocampal centers by viral-mediated expression of inactive FOXO6 leads to defects in recent memory consolidation and neuronal dendrite structure.

As to presently observed insulin/Akt-dependent decreases in FOXO and PGC-1 activities in brains of insulin-resistant animals, also note the following: 1) FOXOs promote DNA repair, resistance to oxidative stress, and cellular and whole-organism longevity (33,34); 2) selective neuronal knockout of the insulin receptor or IGF-I receptor and expected activation of FOXOs and PGC-1α diminish $A\beta_{1-40/42}$ peptides in transgenic Tg2576/AD mice (36); 3) in Caenorhabditis elegans, knockdown of the insulin/IGF-I-like receptor DAF-2, and subsequent activation of nematode FOXO DAF-16, diminishes $A_{\beta 1-40/42}$ peptide expression and toxicity (37); 4) increases in Akt activity and phosphorylation of Akt substrates are seen in temporal cortical neurons of AD patients, and there are eventual losses of Akt-phosphorylated neurons in the hippocampus in end stages of AD (38,39); 5) increases in Akt activity are seen in enterorhinal, hippocampal, and temporal lobe neurons of AD patients and may contribute to neurofibrillary tangles (40); 6) FOXO3a and FOXO6 expression is decreased in all brain cortical regions in HFF mice (41); 7) resveratrol-induced activation of sirtuin-1 (which, by deacetylation, activates both FOXOs and PGC-1α) protects against neuronal degeneration (42, 43); and 8) sirtuin-1, by deacetylation, activates FOXO and its salutary effects on longevity (30,31,43,44).

In concert with the data demonstrated at least in this Example, increased Akt and GSK3β phosphorylation has recently been observed in brains of mice consuming a 60% kcal diet (45). Some findings, however, seemed to suggest that brain insulin signaling is diminished with caloric excess and high-fat feeding and furthermore seem to be at odds with the idea that FOXO has long-term salutary effects on neurons. Thus, caloric restriction over 6 months in transgenic Tg2576/AD mice expressing a mutated human APP gene led to seemingly increased phosphorylation of cortical Akt and FOXO3a and attenuated cortical AD pathology (46). Also, 5-6 months of high-fat feeding of Tg2576/AD mice (8) and normal mice (47) led to seemingly diminished phosphorylation of brain Akt and GSK3α/β and increased $A\beta_{1-40/42}$ peptide generation and AD pathology. In both Tg2576/AD studies (8,46), signaling in normal mice and signaling responses to administered insulin were not determined, and the circulating levels of insulin when brains were taken are unclear. In any case, it was surmised that brain insulin resistance was increased by high-fat feeding and diminished by caloric restriction, and findings were interpreted as suggesting that insulin levels, via Akt, improved AD development and FOXO abetted AD development.

The reason for differences in alterations in brain insulin signaling after dietary alterations can reflect the following: differences in mouse age and strain; duration of dietary alterations; and absence of preexisting AD pathology in presently studied mice, as opposed to brains with more advanced AD pathology, especially in Tg2576/AD mice, in which brain insulin resistance may have occurred secondarily. Further, Tg2576 mice develop spontaneous hyperphagia, obesity, and insulin resistance (48,49) and may therefore have increased sensitivity to a high-fat diet with inhibitory effects of fats on brain Akt signaling that are similar to those seen in liver (16,17,19). As to alterations in Aβ1-40/42 peptides seen in previous dietary studies (8,46,47), HFF-induced increases and caloric restriction-induced decreases in plasma insulin levels, rather than reported alterations in Akt signaling (which may not be relevant to insulin effects on Aβ1-40/42 peptide generation), may have contributed to respective increases and decreases in Aβ1-40/42 peptide production. Finally, although long-term loss of brain FOXO activity may be detrimental by impairing FOXO/PGC-1α-dependent neuronal stem cell function (as suggested from neuronal-specific FOXO knockout studies [33-35]), short-term loss of brain FOXO activity may be beneficial by diminishing neuronal apoptosis in established AD.

It was observed that with increased phosphorylation/inhibition of FOXO1, the levels of PGC-1α, and presumably its FOXO-dependent activity, were diminished in HFF and ob/ob mice because PGC-1α is important for maintaining mitochondrial biogenesis, oxidative processes, and antioxidant protection; moreover, PGC-1α levels are diminished in human and experimental AD and correlate inversely with $A\beta_{1-40/42}$ peptide accumulation and mitochondrial dysfunction (50-52).

As to increases in tau phosphorylation in brains of ob/ob mice and T2DM monkeys, Ser-202 is phosphorylated by extracellular signal-related kinase and increased by hyperinsulinemia (27). However, the kinase responsible for increased Thr-231-tau hyperphosphorylation in ob/ob mice and T2DM monkeys is uncertain, as GSK38 was hyperphosphorylated (i.e., reduced in Akt-dependent activity). On the other hand, this increase in p-Thr-231-tau can be reflective of a more advanced stage of glucose intolerance, because increased Thr-231-tau phosphorylation is seen in diabetic db/db and streptozotocin-induced diabetic mice (53) and may reflect activation of extracellular signal-related kinase 2, c-Jun N-terminal kinase, p38 kinase, PKC, or aPKC. Irrespective of the mechanism, increases in p-tau may contribute to intraneuronal fibrillary tangles.

Because β-amyloid plaques in AD are composed of insoluble highly polymerized Aβ1-40/42 peptides, it was particularly important to find that Aβ1-40/42 peptide levels were increased not only basally as seen here and by others (45) in hyperinsulinemic HFF mice but also in ob/ob mice and obese/T2DM monkeys and, perhaps most intriguingly, after short-term insulin treatment in normal mice. Moreover, in monkeys with long-standing insulin resistance, but not in HFF and ob/ob mice with short-lived insulin resistance, the levels of APP were diminished. Taken together, these can demonstrate that, in the short term, insulin increases the proteolytic release of $A\beta_{1-40/42}$ from APP and that this conversion is incremental at first but, over time, leads to measureable decreases in APP levels; further, the released $A\beta_{1-40/42}$ may be cleared, ironically, by insulin-degrading enzyme but, over time, may also accumulate to produce characteristic AD β-amyloid plaques that impair cognition/memory and promote neuronal atrophy. In this scenario, the underlying mechanism for plaque formation may involve altered activities of α/β/γ-secretases that regulate $A\beta_{1-40/42}$ peptide release from APP or altered insulin-degrading enzyme activity.

Although the data presented in this Example can demonstrate that the brain is initially hyperinsulinized in insulin-resistant states of obesity, the metabolic syndrome, and T2DM, it should be emphasized that with the development and progression of AD pathology, the brain may secondarily become insulin resistant.

To summarize, the data presented in at least in this Example can demonstrate that hyperinsulinemia provokes excessive increases in activities of Akt and aPKC in brains of insulin-resistant mice and monkeys, and this hyperinsulinization leads to decreases in FOXOs and PGC-1α levels and increases in levels of Aβ$_{1-40/42}$ peptides and p-tau (i.e., changes that may reasonably link insulin-resistant states to AD development). The correction of systemic insulin resistance and hyperinsulinemia can restore normal CNS insulin signaling and abolish this linkage.

REFERENCES FOR EXAMPLE 2

King H, Aubert R E, Herman W H. Global burden of diabetes, 1995-2025: prevalence, numerical estimates, and projections. Diabetes Care 1998; 21:1414-1431.

Reaven G M. Pathophysiology of insulin resistance in human disease. Physiol Rev 1995; 75:473

Petersen K F, Befroy D, Dufour S, et al. Mitochondrial dysfunction in the elderly: possible role in insulin resistance. Science 2003; 300:1140-1142

Slawik and Vidal-Puig. Lipotoxicity, overnutrition and energy metabolism in aging. Ageing Res Rev 2006; 5:144-164

Ussher and Lopaschuk. The malonyl CoA axis as a potential target for treating ischaemic heart disease. Cardiovasc Res 2008; 79:259-268

Dyck et al. Malonyl coenzyme a decarboxylase inhibition protects the ischemic heart by inhibiting fatty acid oxidation and stimulating glucose oxidation. Circ Res 2004; 94:e78-e84

Dyck et al. Absence of malonyl coenzyme A decarboxylase in mice increases cardiac glucose oxidation and protects the heart from ischemic injury. Circulation 2006; 114:1721-1728

Ussher et al. Insulin-stimulated cardiac glucose oxidation is increased in high-fat diet-induced obese mice lacking malonyl CoA decarboxylase. Diabetes 2009; 58:1766-1775

Koves et al. Mitochondrial overload and incomplete fatty acid oxidation contribute to skeletal muscle insulin resistance. Cell Metab 2008; 7:45-56

Ussher et al. Stimulation of glucose oxidation protects against acute myocardial infarction and reperfusion injury. Cardiovasc Res 2012; 94:359-369

Ussher et al. Inactivation of the cardiomyocyte glucagon-like peptide-1 receptor (GLP-1R) unmasks cardiomyocyte-independent GLP-1R-mediated cardioprotection. Mol Metab 2014; 3:507-517

Ussher et al. Inhibition of de novo ceramide synthesis reverses diet-induced insulin resistance and enhances whole-body oxygen consumption. Diabetes 2010; 59:2453-2464

Constantin-Teodosiu et al. A sensitive radioisotopic assay of pyruvate dehydrogenase complex in human muscle tissue. Anal Biochem 1991; 198:347-351

Alrob et al. Obesity-induced lysine acetylation increases cardiac fatty acid oxidation and impairs insulin signalling. Cardiovasc Res 2014; 103:485-497

Lopaschuk et al. Targeting intermediary metabolism in the hypothalamus as a mechanism to regulate appetite. Pharmacol Rev 2010; 62:237-264

Robbel et al. Consecutive enzymatic modification of ornithine generates the hydroxamate moieties of the siderophore erythrochelin. Biochemistry 2011; 50:6073-6080

Samokhvalov et al. Inhibition of malonyl-CoA decarboxylase reduces the inflammatory response associated with insulin resistance. Am J Physiol Endocrinol Metab 2012; 303:E1459-E1468

Reznick et al. Aging-associated reductions in AMP-activated protein kinase activity and mitochondrial biogenesis. Cell Metab 2007; 5:151-156

Baur et al. Resveratrol improves health and survival of mice on a high-calorie diet. Nature 2006; 444:337-342

Savage et al. Disordered lipid metabolism and the pathogenesis of insulin resistance. Physiol Rev 2007; 87:507-520

Coen et al. Insulin resistance is associated with higher intramyocellular triglycerides in type I but not type II myocytes concomitant with higher ceramide content. Diabetes 2010; 59:80-88

Chavez et al. A ceramide-centric view of insulin resistance. Cell Metab 2012; 15:585-594

Muoio and Neufer. Lipid-induced mitochondrial stress and insulin action in muscle. Cell Metab 2012; 15:595-605

Samuel and Shulman. Mechanisms for insulin resistance: common threads and missing links. Cell 2012; 148:852-87

Bouzakri et al. Malonyl coenzyme A decarboxylase regulates lipid and glucose metabolism in human skeletal muscle. Diabetes 2008; 57:1508-1516

Muoio and Newgard. Mechanisms of disease: molecular and metabolic mechanisms of insulin resistance and beta-cell failure in type 2 diabetes. Nat Rev Mol Cell Biol 2008; 9:193-205

Karnati et al. Mammalian SOD2 is exclusively located in mitochondria and not present in peroxisomes. Histochem Cell Biol 2013; 140:105-117

Idell-Wenger et al. Coenzyme A and carnitine distribution in normal and ischemic hearts. J Biol Chem 1978; 253:4310-4318

Canto et al. NAD(+) metabolism and the control of energy homeostasis: a balancing act between mitochondria and the nucleus. Cell Metab 2015; 22:31-53

Example 3

The ability to treat systemic insulin-resistant disorders and potentially related CNS cognitive disorders, in particular AD, is limited. Presently available insulin-sensitizers, thiazolidinediones (usage of which has waned), metformin, and certain incretins have only modest indirect effects on insulin resistance, and their effects on the brain and AD need to be re-assessed in light of new findings. Metformin, the most widely used oral agent for treating T2DM, has been proposed to be useful in AD, which we now believe may reflect beneficial effects of meformin owing to (a) limiting hepatic glucose production and thereby improving insulin resistance and hyperinsulinemia, and (b) direct stimulatory effects on neurogenesis and memory formation. Indeed, metformin increases aPKC activity in muscle and liver (FIGS. 2A-2F and 3A-3D), and, since aPKCs appear to be important in memory functions, metformin can improve memory function in AD by activating brain aPKCs. Metformin use, however, needs to reassessed in view of our findings suggesting that CNS aPKC activation may also have detrimental effects on a variety of CNS parameters, in particular, aPKC-dependent increases in Aβ$_{1-40/42}$ peptides. In this regard, although metformin may improve CNS abnormalities, perhaps by decreasing hyperinsulinemia and/or activating CNS PKC-λ/ι or PKMζ, metformin has also been reported to increase Aβ$_{1-40/42}$ peptides and perhaps other aPKC-dependent processes that can be detrimental when excessive and persistent.

As to therapeutic effects of metformin in liver, it now appears that metformin diminishes hepatic gluconeogenesis by directly inhibiting components of mitochondrial respiratory chain and/or mitochondrial glyceraldehyde dehydrogenase, rather than by activating AMPK and diminishing gluconeogenic (PEPCK/G6Pase) enzyme expression. Moreover, metformin action in liver is unfortunately accompanied by undesirable increases in hepatic aPKC activity (FIGS. 3A-3D), which in turn provoke increases in activity of SREBP-1c and SREBP-1c-dependent expression of lipogenic enzymes (FIGS. 2A-2F) [clinically, however, increases in lipogenic enzymes may be masked by decreases in appetite, weight loss and AMPK-dependent increases in lipid oxidation]. In addition, like the obesity/T2D-dependent increases in hepatic aPKC activity seen in mouse livers and human hepatocytes, metformin-induced increases in aPKC activity [seen here in preliminary studies of normal human hepatocytes using a relevant 100 μM metformin concentration] were attended by impairments in Akt activation and action, and by increases in gluconeogenic enzyme expression in normal hepatocytes (FIGS. 2A-3D). In short, these untoward effects of metformin were provoked by hyperactivation of aPKC and would be expected to diminish insulin action. The latter seems likely, as decreases in activity or levels of hepatic aPKC [elicited byadenovirus (Adv)-mediated expression of kinase-inactive aPKC, chemical inhibitors of aPKC, and knockout-induced deficiencies of hepatic aPKC] diminish aPKC-dependent abnormalities in HFF mice, ob/ob mice, Het-MλKO mice, and hepatocytes of T2D humans (FIGS. 2A-3D).

Stated differently, decreases in hepatic aPKC activity: (a) restore insulin effects on hepatic Akt and Akt-dependent effects on hepatic FoxO1 and PGC-1 a phosphorylation, and thereby diminish gluconeogenesis; (b) diminish excessive expression of hepatic lipogenic enzymes and proinflammatory cytokines; and (c) improve hyperinsulinemia and clinical abnormalities (FIGS. 1-3D). And, most importantly, effective inhibition of hepatic aPKC markedly improves hyperinsulinemia in Het-MλKO mice, such that CNS insulin signaling and $A\beta_{1-40/42}$ peptide production return to normal (FIGS. 4A-4F). Also note that inhibitors of hepatic aPKC block the undesirable hepatic effects of metformin that arise from hepatic aPKC activation (FIGS. 2A-3D), but do not appear to diminish aPKC-independent salutary effects of metformin on mitochondrial factors that control gluconeogenesis, and AMPK-dependent inhibition of acetyl-CoA carboxylase (ACC), which increases hepatic lipid oxidation. Metformin may also increase $A\beta_{1-40/42}$ peptide production by activating CNS aPKC, which can explain why metformin has been reported to be variously detrimental and, on the other hand, useful for controlling $A\beta_{1-40/42}$ peptide production and cognitive memory functions in AD.

Example 4

To understand how the brain is spared from developing insulin resistance when such resistance is present in certain other organs, it is important to recall that insulin resistance is "selective" and develops specifically in response to an alteration in glucose homeostasis, e.g. in liver or muscle, that leads to hyperinsulinemia, which in turn can activate or hyperactivate "open" (non-downregulated) insulin signaling pathways. In this regard, the earliest defect in obese adolescents involves excessive hepatic gluconeogenesis. This corresponds with the observation that increased hepatic gluconeogenic enzyme expression is an early event in the development of systemic insulin resistance in HFF mice and ob/ob mice. However, an initial abnormality in glucose homeostasis in muscle, as in Het-MλKO mice [in which glucose transport is impaired by partial deficiency of muscle aPKC] can provoke compensatory increases in insulin secretion, and the resulting hyperinsulinemia hyperactivates hepatic aPKC, thereby increasing expression of lipogenic and gluconeogenic enzymes. This increase in gluconeogenic enzymes in Het-MλKO mice can stem from the fact that excessive activation of hepatic aPKC selectively diminishes the ability of Akt to phosphorylate FoxO1 and PGC-1α on the WD40/ProF platform, e.g., the same as that found in HFF and ob/ob mice. Increases in insulin-stimulated lipogenic enzyme expression in Het-MλKO mice reflects aPKC/Akt-dependent increases in SREBP-1c activity As portrayed in FIG. 1, in early stages of insulin resistance in HFF and ob/ob mice, insulin activation of hepatic IRS-1-dependent PI3K, IRS-2-dependent PI3K, and subsequent activation of both Akt and aPKC are intact or increased, despite the fact that Akt-dependent regulation of hepatic FoxO1, PGC-1 a and gluconeogenesis is impaired. This initial selective impairment in hepatic Akt-dependent phosphorylation of FoxO1 (but not of Akt-dependent GSK3β or mTOR) and the subsequent upregulation of hepatic gluconeogenesis in HFF and ob/ob mice is explained by the fact that the action of Akt on FoxO1 and PGC-1α is compartmentalized in liver on, and facilitated by, a 40 kDa, WD (tryp/asp-x-x)-repeat, seven-bladded, propeller-like, FYVE-containing, scaffolding protein, "WD40/ProF". Moreover, in liver, this action of Akt on FoxO1 and PGC-1α can be inhibited by co-localized aPKC, which is hyperactivated by diet-dependent increases in lipids, e.g., ceramide and phosphatidic acid (PA), that directly activate aPKC [note that aPKC binds, phosphorylates, inhibits Akt, and, in liver, displaces Akt2 from the hepatic WD40/ProF platform]. With specific impairments of hepatic Akt-dependent FoxO1 and PGC-1 a phosphorylation, and subsequent increases in FoxO1, PGC-1α and gluconeogenesis, hyperinsulinemia ensues and hyperactivates hepatic Akt, which, along with aPKC, increases signaling to: (a) mTORC1, SREBP-1c, and lipogenic enzymes; and (b) NFκB and proinflammatory cytokines.

In addition to FoxO1 [which was reported earlier], we recently found that Akt-dependent phosphorylation, and thus inhibition, of hepatic PGC-1α, like FoxO1, takes place on the WD40/ProF platform, and this action of Akt is impaired in HFF mice and livers of obese and T2D humans. Accordingly, PGC-1α can be directly involved, along with FoxO1 and HNF4, in increases in gluconeogenic enzyme expression in all insulin-resistant states we have examined, including humans, and is indirectly involved in SREBP-1 c-dependent increases in lipogenic enzyme expression. This sequence, amongst others, helps to explain the paradox that hepatic output of both glucose and lipids is increased in insulin-resistant states).

An increase in lipid release from expanded fat depots in obesity has similarly been shown to secondarily involve the liver, apparently via released lipids that activate hepatic aPKC and cause hepatic insulin resistance. Thus, regardless of the initiating process, outcomes in liver and brain would probably be comparable to those seen in HFF, ob/ob and Het-MλKO mice.

In later stages of insulin resistance (FIG. 1), note that insulin signaling to insulin receptor substrate (IRS)-1-dependent phosphatidylinositol 3-kinase (PI3K) is impaired in liver, as well as muscle. And, in muscle, both Akt and aPKC are controlled by IRS-1/PI3K, rather than IRS-2/PI3K, during insulin action, and activities of both kinases are therefore reduced in insulin-resistant states. In liver, a defect in IRS-1/PI3K similarly occurs and indeed impairs hepatic Akt activity; in contrast, however, insulin signaling to hepatic IRS-2/PI3K is well conserved even in advanced T2DM; and, since IRS-2/PI3K, rather than IRS-1, is the major activator of hepatic aPKC, aPKC activation is well preserved, and, in fact, excessively activated in livers of HFF mice, and obese and T2D rodents and humans.

Example 5

Hyperinsulinemia hyperactivates Akt and aPKC in brains of insulin-resistant mice and monkeys. It was observed in experimental models that excessive insulin signaling in the CNS in multiple insulin-resistant experimental models is actually deleterious and can lead to AD. Nevertheless, there is considerable evidence that AD is more prevalent in insulin-resistant conditions, and each of the insulin-resistant experimental states that was examined are characterized by excessive activation of both major insulin-dependent protein kinases, viz., Akt and aPKC, and their hyperactivation certainly has the potential to alter multiple factors that may be involved in AD pathogenesis. In addition to aberrations in FoxOs, PGC-1α, phospho-tau and $A\beta_{1-40/42}$ peptides, we are also concerned that hyperinsulinemia-induced increases in diacylglycerol (DAG) via the de novo pathway, or increases in DAG induced by increases in lipids and/or glucose through the de novo pathway, may also be activating some or all conventional/novel (c/n) PKCs in the CNS in insulin-resistant states. Indeed, in HFF mice, we found that all examined c/nPKCs ($\alpha,\beta,\delta,\epsilon,\theta$) were activated in muscle, whereas, in liver, only PKC-λ was activated (unpublished). Also note that, in liver and possibly in other tissues, insulin itself, via aPKC, and possibly via Akt, increases NFκB activity and expression of proinflammatory cytokines that may be detrimental, particularly if prolonged and excessive. We therefore believe that it is important to see if excessive insulin signaling in the brain might adversely affect AD development through these and other mechanisms, and whether agents that reverse hyperinsulinemia, e.g., liver-selective aPKC inhibitors and metformin, can reverse alterations in c/nPKCs and NFκB-dependent proinflammatory cytokines.

The idea that insulin signaling in the CNS is excessive in hyperinsulinemic phases of insulin-resistant states, and that this CNS hyperactivity may contribute to AD development, is distinctly different from the more prevalent notion that the brain itself is insulin-resistant, and this predisposes to AD development. However, it can be that the initial period of CNS hyperinsulinization may be followed by insulin resistance and hypoinsulinization, particularly in damage areas where β-amyloid plaques and/or neurofibrillary phospho-tau tangles develop.

Hyperinsulinemia and hyperactivation of Akt and aPKC do in fact persist throughout the first year of life in insulin-resistant Het-MλXO mice that have a full-blown metabolic syndrome with abdominal obesity, hyperlipidemia, hepatosteatosis and modest T2DM. Also note that insulin signaling to Akt, FoxO1/3a/4/6, GSK3β, mTOR and aPKC is increased in monkeys in which insulin-resistant states of obesity and T2D have been present for many years, suggesting that insulin signaling in the brain can remain excessive over long periods. The failure to develop CNS insulin resistance in these models may reflect that IRS-2/PI3K can be more important than IRS-1/PI3K in mediating insulin effects in the CNS, and IRS-2 is less susceptible to down-regulation than IRS-1 in insulin-resistant conditions.

There is evidence that both CNS aPKCs, 70 kDa-PKC-ι/λ [which is activated by insulin and other agents that activate aPKCs, e.g., metformin] and 50 kDa PKC-ζ [aka, "PKMζ"; which, lacking a regulatory domain with its auto-inhibitory pseudosubstrate, is constitutively-active] can function in long-term potentiation (LTP) and long-term spatial memory. Moreover, with knockout of PKMζ, long considered to be required for LTP and long-term memory, PKC-λ/ι can compensate to maintain LTP. However, PKC-ι/λ, may also play a role in short-term memory and LTP, distinct from PKMζ.

Example 6

Figure 6:
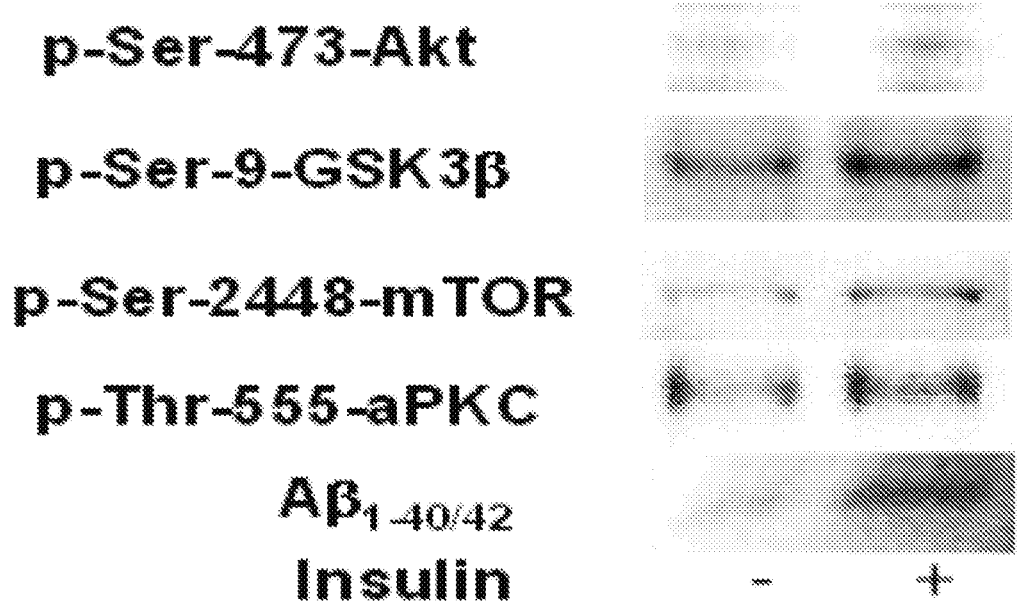
FIG. 6 depicts effects of 200 nM insulin in LA1-5s human neuroblastoma cells during a 60-min incubation.

To investigate the effect of insulin on CNS signaling, LA1-55 neuroblastoma cells were treated for 1 hour with 200 nM of insulin. The results are shown in FIG. 6. The results can demonstrate that insulin treatment can increase Akt activity, Akt-dependent GSK3β and mTOR phosphorylation, aPKC activity and $A\beta_{1-40/42}$ peptide levels in neuronal cells.

Additionally, activation of CNS p-Ser-473-Akt, p-Thr-55/560-aPKC, BACE1, aPKC activity and $A\beta_{1-40/42}$ levels, by insulin in various mouse models was evaluated. Results are shown in FIGS. 5A-5B, FIGS. 7-8C.

Example 7

In initial studies, it was observed that the doses of aPKC inhibitors, ACPD and ICAP, that were effective in partially diminishing activity of hepatic aPKC to an extent that largely improved hepatic and clinical signaling abnormalities did not improve hyperinsulinemia sufficiently to significantly diminish the hyperactivation of CNS Akt and aPKC in insulin-resistant HFF and ob/ob mice (3). In doses employed in these studies, ACPD and ICAP were similarly unable to diminish acute effects of insulin on CNS aPKC activity in normal mice. In studies with Het-MλKO mice, however, aPKC inhibitor, aurothiomalate (ATM), by inhibiting hepatic aPKC and thereby improving hepatic abnormalities, markedly improved hyperinsulinemia, and this corrected the aberrant increases in CNS insulin signaling to Akt and aPKC, thereby reducing phosphorylation of Akt substrates, and, most importantly, reducing $A\beta_{1-40/42}$ peptide levels to normal. With these improvements and return of all CNS parameters to normal basal levels, ATM also restored the ability of insulin to acutely increase all insulin-dependent CNS factors to maximal, including Akt, aPKC and $A\beta_{1-40/42}$ peptide levels. Similarly, using aPKC inhibitor, ICAPP, to treat Het-MλKO mice, hyperinsulinemia was corrected, and, in preliminary studies, we found that all aberrations in CNS insulin signaling, including $A\beta_{1-40/42}$ peptide production, returned to normal (FIGS. 4A-4F). However, in contrast to ATM, the ability of insulin to acutely and specifically activate CNS aPKC and increase $A\beta_{1-40/42}$ peptide levels was abrogated by ICAPP treatment of Het-MλKO mice; on the other hand, insulin was fully able to fully activate Akt and increase Akt-dependent phosphorylations despite ICAPP treatment (FIGS. 4A-4F, 5A-5B, and 7). Moreover, in preliminary studies of normal WT mice, ICAPP pre-treatment blocked acute effects of insulin on aPKC, β-secretase (BACE1) and $A\beta_{1-40/42}$ peptide levels, again, without inhibiting insulin effects on Akt in the CNS (FIGS. 4A-4F, 5A-5B, and 7). From these findings, it was observed that ICAPP, in relatively low doses, can cross the BBB, and can specifically block insulin effects on aPKC and aPKC-dependent processes, most notably, $A\beta_{1-40/42}$ peptide production.

Moreover, since long-standing β-APP protein levels are decreased in obese/T2D monkeys at the same time that Aβ$_{1-40/42}$ peptide levels are increased, it can be that Aβ$_{1-40/42}$ peptides are produced at the expense of β-APP, most likely by activation of β/γ-secretase (see FIGS. 5A-5B, 7, and 8).

As aPKCs are "promiscuously" activated by a variety of lipids [PIP3, ceramide, phosphatidylserine, PA, lipids and glucose that can be converted to PA, activation of PLD by many agents to yield PA, and by DAG which is readily phosphorylated to produce PA], there obviously are many factors that have the potential to adversely increase production of CNS Aβ$_{1-40/42}$ peptide levels, and, thus, increase β-amyloid plaque formation. And, with a specific aPKC inhibitor that can pass the BBB, it can be possible to effectively treat abnormalities in Aβ$_{1-40/42}$ peptide production in AD.

Example 8

Figure 9:
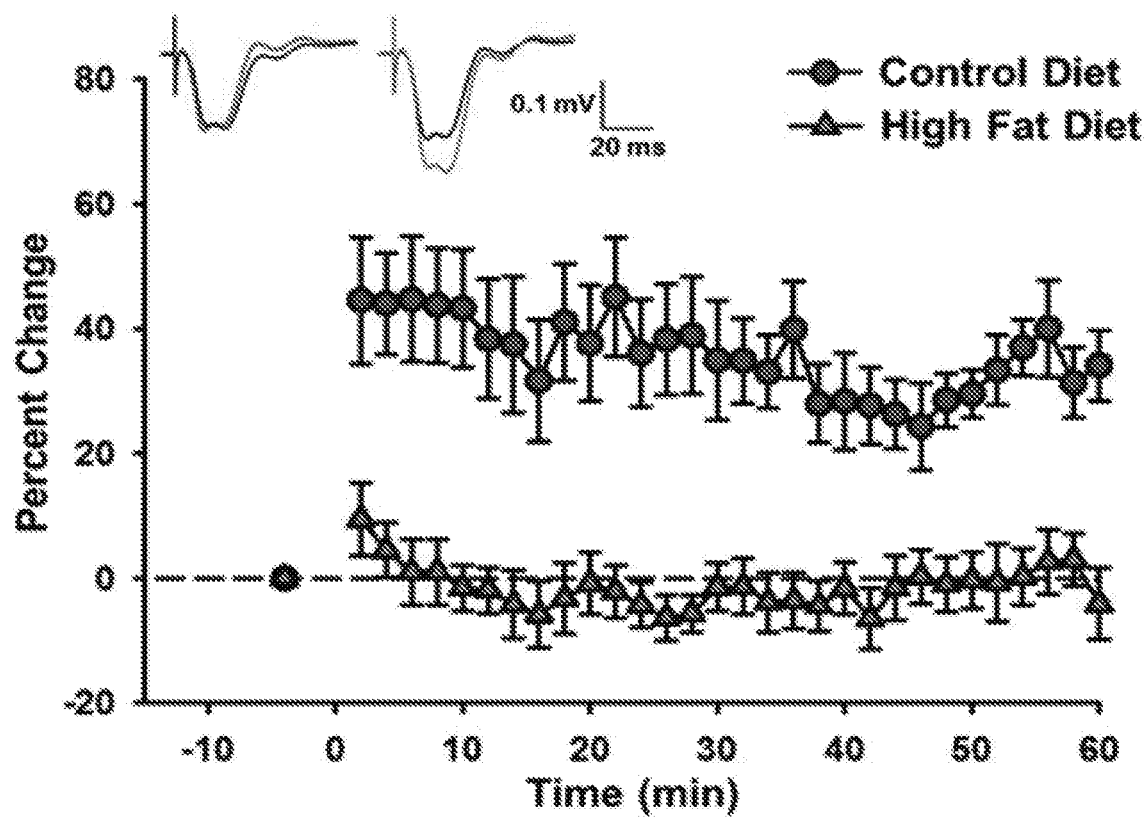
FIG. 9 depicts effects of 3 weeks of high fat feeding on primed burst potentiation in the hippocampus. Data from single pulse responses are represented relative to the 10 min mean before tetanizing stimulation at time 0. Slices from the control group, but not the high fat group, show a significant increase in EPSP, inset illustrates stratum radiatum EPSP baselines (in black) and mean responses 51-60 min post-PBP stimulation from high fat (red) and control (blue) groups.

It has been observed that hepatic insulin resistance in HFF mice leads to hyperinsulinemia and thus to hyperactivation of insulin signaling pathways in the CNS. Although, hepatic and clinical abnormalities are largely prevented by administration of liver-selective aPKC inhibitors in HFF mice in doses that do not enter the CNS, hyperinsulinemia was not reduced sufficiently to reverse CNS abnormalities in HFF mice. Nevertheless, HFF mice were observed to have increased BACE1 activity and Aβ$_{1-40/42}$ peptide increases (FIG. 8) and CNS cognitive deficits (FIG. 9), and this model is therefore well-suited for longitudinal studies to follow progression of: (a) cognitive and memory abnormalities, and their correlation with alterations in CNS BACE1, Aβ$_{1-40/42}$ peptide levels, FoxO activities, etc; and (b) effects of interventions with agents that inhibit liver aPKC alone (ACPD±ICAP±Adv-Cre), or metformin, or metformin±ACPD, or agents that inhibit liver and brain aPKC (ICAPP).

The heterozygous muscle-specific PKC-λ knockout (Het-MλKO) mouse model. The Het-MλKO mouse has also been extensively studied in our laboratory. In this model, insulin resistance starts in muscle and secondarily involves the liver, where hyperactivation of aPKC leads to increases in gluconeogenic and lipogenic enzymes, and development of a full-blown metabolic syndrome with abdominal obesity, hyperlipid-emia and hepatosteatosis, and, in later stages, T2DM. These mice are easy to breed and invariably insulin-resistant. Their insulin resistance and clinical abnormalities are progressive, but can be fully and rapidly [within 5-8 days] reversed by treatment with a variety of inhibitors of hepatic aPKC, including: Adv-mediated expression of kinase-inactive (KI) aPKC; and aPKC inhibitors, ATM and ICAPP, and ACPD and ICAPP. Having PKC-λ-floxed genes, PKC-λ levels in Het-MλKO mice can be reduced at will by IV Adv-Cre treatment. Indeed, hyperinsulinemia in these mice is fully reversed by ATM and ICAPP, and this [and perhaps, with improvements in glucose and fatty acids (37)] corrects insulin-dependent CNS aberrations. Accordingly, Het-MλKO mice are well-suited for long-term longitudinal and intervention studies.

We claim:

1. A method of treating Alzheimer's disease (AD) or symptoms thereof in a subject in need thereof, the method comprising administering to the subject an effective amount of aurothiomalate (ATM).

2. The method of claim 1, wherein the amount of the ATM is an amount effective to decrease phosphorylation of Akt.

3. The method of claim 1, wherein the amount of the ATM is an amount effective to decrease activity of aPKC.

4. The method of claim 1, wherein the amount of the ATM is an amount effective decrease activity of β-secretase.

5. The method of claim 1, wherein the amount of the ATM is an amount effective decrease the amount of Aβ$_{1-40/42}$.

6. The method of claim 1, wherein the amount of the ATM is an amount effective decrease the amount of thr-231-phospho-tau.

7. The method of claim 1, wherein the amount of the ATM is an amount effective decrease the activity of 70 kDa PKC-λ/ι.

8. The method of claim 1, wherein the amount of the ATM is an amount effective to increase the activity of FoxOI, FoxO3a, or FoxOI and FoxO3a.

9. The method of claim 1, wherein the amount of the ATM is an amount effective to increase activity, levels, or activity and levels of PGC-1α.

10. The method of claim 1, wherein the subject in need thereof is hyperinsulinemic.

11. The method of claim 1, wherein the subject in need thereof is hyperinsulinemic in the central nervous system.

12. The method of claim 1, wherein the subject in need thereof is diabetic.

13. The method of claim 1, wherein the subject has metabolic syndrome.

14. The method of claim 1, wherein in the subject is obese.

15. The method of claim 1, wherein the amount of the ATM is administered to the subject in need thereof once daily.

16. The method of claim 1, wherein the amount of the ATM is administered to the subject in need thereof once every other day.

17. The method of claim 1, wherein the amount of the ATM administered ranges from about 50 mg/kg to about 70 mg/kg.

18. The method of claim 1, wherein the amount of the ATM 1s administered intravenously or subcutaneously.

* * * * *